(12) United States Patent
Dirat et al.

(10) Patent No.: US 7,393,858 B2
(45) Date of Patent: Jul. 1, 2008

(54) TETRAHYDROPYRAN COMPOUNDS AS TACHYKININ ANTAGONISTS

(75) Inventors: Olivier Dirat, Bishops Stortford (GB); Jason Matthew Elliott, Felsted (GB); Ian Thomas Huscroft, Bishops Stortford (GB); Richard Alexander Jelley, Bishops Stortford (GB); Janusz Jozef Kulagowski, Sawbridgeworth (GB); Piotr Antoni Raubo, Bishops Stortford (GB); Duncan Edward Shaw, Bishops Strotford (GB); Francine Sternfeld, London (GB); Christopher John Swain, Duxford (GB)

(73) Assignee: Merck Sharp & Dohme Ltd., Hertfordshire (GB)

( * ) Notice: Subject to any disclaimer, the term of this patent is extended or adjusted under 35 U.S.C. 154(b) by 249 days.

(21) Appl. No.: 10/548,678

(22) PCT Filed: Mar. 4, 2004

(86) PCT No.: PCT/GB2004/000918

§ 371 (c)(1),
(2), (4) Date: Sep. 8, 2005

(87) PCT Pub. No.: WO2004/078750

PCT Pub. Date: Sep. 16, 2004

(65) Prior Publication Data

US 2006/0172999 A1 Aug. 3, 2006

(30) Foreign Application Priority Data

| Mar. 7, 2003 | (GB) | ................................. | 0305279.2 |
| Mar. 7, 2003 | (GB) | ................................. | 0305280.0 |
| Mar. 7, 2003 | (GB) | ................................. | 0305281.8 |
| Mar. 7, 2003 | (GB) | ................................. | 0305282.6 |
| Mar. 7, 2003 | (GB) | ................................. | 0305283.4 |
| Mar. 13, 2003 | (GB) | ................................. | 0305822.9 |
| Mar. 13, 2003 | (GB) | ................................. | 0305823.7 |

(51) Int. Cl.
*A61K 31/438* (2006.01)
*C07D 491/10* (2006.01)

(52) U.S. Cl. ..................... 514/278; 546/16; 548/409; 548/950; 514/409

(58) Field of Classification Search ............... 514/278, 514/227.8, 326, 460, 409; 546/16, 207; 544/60; 548/950, 409; 549/419
See application file for complete search history.

(56) References Cited

FOREIGN PATENT DOCUMENTS

| WO | WO 00/56727 | | 9/2000 |
| WO | WO 00/56728 | | 9/2000 |
| WO | WO 02/16343 | | 2/2002 |
| WO | WO 02/16344 | | 2/2002 |
| WO | WO 03/022839 | * | 3/2003 |
| WO | WO 2004/009573 | * | 1/2004 |
| WO | WO 2004/078750 | | 9/2004 |

OTHER PUBLICATIONS

Physicians' Desk Reference, 2007, pp. 1963-1969, 61st Edition, Montvale, New Jersey.

* cited by examiner

*Primary Examiner*—Charanjit S. Aulakh
(74) *Attorney, Agent, or Firm*—Curtis C. Panzer; Valerie J. Camara

(57) ABSTRACT

The present invention relates to compounds of formula (Ia)

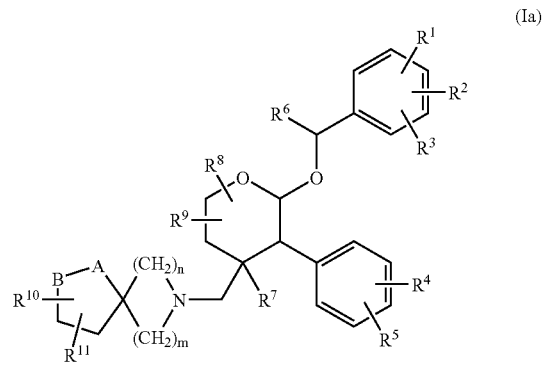

(Ia)

wherein A, B, n, m, $R^1$, $R^2$, $R^3$, $R^4$, $R^5$, $R^6$, $R^7$, $R^8$, $R^9$, $R^{10}$ and $R^{11}$ are defined herein, and pharmaceutically acceptable salts thereof; the compounds are of particular use in the treatment or prevention of depression, anxiety, pain, inflammation, migraine, emesis or postherpetic neuralgia.

9 Claims, No Drawings

TETRAHYDROPYRAN COMPOUNDS AS TACHYKININ ANTAGONISTS

CROSS REFERENCE TO RELATED APPLICATIONS

This application is a U.S. National Phase application under 35 U.S.C. § 371 of PCT Application No. PCT/GB2004/000918, filed Mar. 4, 2004, which claims priority under 35 U.S.C. § 119 from GB Application No. 0305279.2, filed Mar. 7, 2003, GB Application No. 0305280.0, filed Mar. 7, 2003, GB Application No. 0305281.8, filed Mar. 7, 2003, GB Application No. 0305282.6, Filed Mar. 7, 2003, GB Application No. 0305283.4, Filed Mar. 7, 2003, GB Application No. 0305822.9, filed Mar. 13, 2003, and GB Application No. 0305823.7, filed Mar. 13, 2003.

This invention relates to a class of tetrahydropyran compounds which are useful as tachykinin antagonists. More particularly, the compounds of the invention are useful as neurokinin 1 (NK-1) receptor antagonists.

The present invention provides compounds of the formula (I):

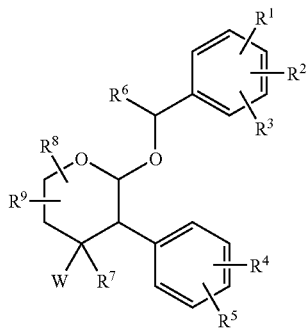

(I)

and pharmaceutically acceptable salts thereof
wherein
W represents:

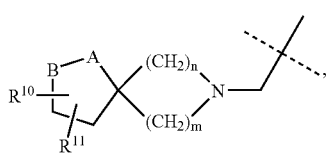

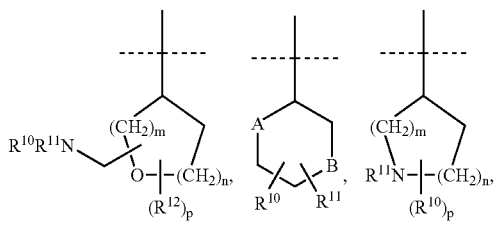

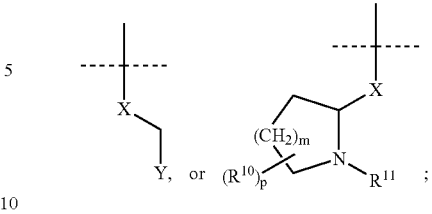

$R^1$ is hydrogen, halogen, $C_{1-6}$alkyl, $C_{1-6}$alkoxy, fluoro$C_{1-6}$alkyl, fluoro$C_{1-6}$alkoxy, $C_{3-7}$cycloalkyl, $C_{3-7}$cycloalkyl$C_{1-4}$alkyl, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, fluoro$C_{1-6}$alkyl or $C_{1-6}$alkoxy substituted by $C_{1-4}$alkoxy;

$R^3$ is hydrogen, halogen or fluoro$C_{1-6}$alkyl;

$R^4$ is hydrogen, halogen, $C_{1-6}$alkyl, $C_{1-6}$alkoxy, fluoro$C_{1-6}$alkyl, fluoro$C_{1-6}$alkoxy, hydroxy, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, fluoro$C_{1-6}$alkyl or $C_{1-6}$alkoxy substituted by $C_{1-4}$alkoxy;

$R^6$ represents hydrogen or a $C_{1-4}$-alkyl group optionally substituted by a hydroxy group;

$R^7$ represents hydrogen, $C_{1-6}$alkyl, fluoro$C_{1-6}$alkyl, hydroxy, $C_{1-6}$alkoxy or hydroxy$C_{1-6}$alkyl;

$R^8$ and $R^9$ each independently represent hydrogen, halogen, $C_{1-6}$alkyl, $CH_2OR^c$, oxo, $CO_2R^a$ or $CONR^aR^b$ where $R^a$ and $R^b$ are as previously defined and $R^c$ represents hydrogen, $C_{1-6}$alkyl or phenyl;

and pharmaceutically acceptable salts thereof;
wherein when W is

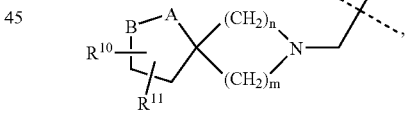

A represents an oxygen atom or a $CH_2$ group;

B represents an oxygen atom or a $CH_2$ group, with the proviso that when A is an oxygen atom, B is a $CH_2$ group, and when A is a $CH_2$ group, B is an oxygen atom;

n is 1 or 2;

m is 1, 2 or 3, with the proviso that the sum total of m+n is 2, 3 or 4;

$R^{10}$ is hydrogen, halogen, hydroxy, $C_{1-4}$alkyl, $C_{3-7}$cycloalkyl, $C_{3-7}$cycloalkyl$C_{1-4}$alkyl, hydroxy$C_{1-4}$alkyl, $C_{1-4}$alkoxy$C_{1-4}$alkyl, $C_{2-6}$alkenyl or $C_{2-6}$alkynyl;

$R^{11}$ is hydrogen, halogen, hydroxy or $C_{1-4}$alkyl;

or $R^{10}$ and $R^{11}$ may together represent an oxo (=O) group, with the proviso that the oxo group is not adjacent to the oxygen atom represented by either A or B;

wherein one or both of $R^{10}$ and $R^{11}$ may replace one or both hydrogen atoms in the $CH_2$ group represented by A or B;
wherein when W is

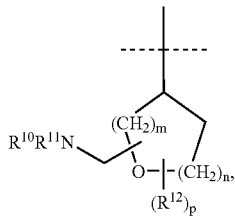

$R^{10}$ is hydrogen, $C_{1-4}$alkyl, $C_{3-7}$cycloalkyl, $C_{3-7}$cycloalkyl$C_{1-4}$alkyl, $C_{2-4}$alkyl substituted by a $C_{1-4}$alkoxy or hydroxyl group;
$R^{11}$ is hydrogen or $C_{1-4}$alkyl, $C_{3-7}$cycloalkyl, $C_{3-7}$cycloalkyl$C_{1-4}$alkyl, or $C_{1-4}$alkyl substituted by $C_{1-4}$alkoxy, hydroxyl or phenyl, wherein said phenyl group is optionally substituted by one, two or three substituents selected from $C_{1-6}$alkyl, $C_{1-6}$alkoxy, halogen and trifluoromethyl;
or $R^{10}$, $R^{11}$ and the nitrogen atom to which they are attached form a heteroaliphatic ring of 4 to 7 ring atoms, optionally substituted by one or two groups selected from hydroxy, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group, which heteroaliphatic ring may optionally contain an oxygen or sulphur ring atom, a group $S(O)$ or $S(O)_2$ or a second nitrogen atom which will be part of a NH or $NR^d$ moiety, where $R^d$ is $C_{1-4}$alkyl optionally substituted by hydroxy or $C_{1-4}$alkoxy, and where $R^e$ is hydrogen, $C_{1-4}$alkyl or benzyl;
$R^{12}$ represents halogen, hydroxy, $C_{1-4}$alkoxy or fluoro$C_{1-4}$alkoxy, or where p is 2, then two $R^9$ groups may together represent an oxo (=O) group;
m is zero, 1 or 2;
n is 1, 2 or 3, with the proviso that the sum total of m+n is 2 or 3; and
p is zero, 1 or 2;
wherein when W is

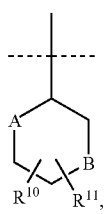

A represents $NR^{12}$ or $S(O)_q$;
B represents $NR^{12}$ or $S(O)_q$, with the proviso that when A is $S(O)_q$, then B is $NR^{12}$, and when A is $NR^{12}$, then B is $S(O)_q$;
$R^{10}$ and $R^{11}$ each independently represent hydrogen, fluorine, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group, where $R^e$ is hydrogen, methyl ethyl or benzyl;
or, when they are attached to the same carbon atom, $R^{10}$ and $R^{11}$ may together represent =O, =CHCO$_2$R$^a$, —O(CH$_2$)$_m$O—, —CH$_2$O(CH$_2$)$_p$—, —CH$_2$OCH$_2$C(O)—, —CH$_2$OCH$_2$CH(OH)—, —CH$_2$OCH$_2$C(CH$_3$)$_2$—, —CH$_2$OC(CH$_3$)$_2$CH$_2$—, —C(CH$_3$)$_2$OCH$_2$CH$_2$—, —CH$_2$C(O)OCH$_2$—, —OC(O)CH$_2$CH$_2$—, —C(O)OCH$_2$CH$_2$—, —C(O)OC(CH$_3$)$_2$CH$_2$—, —C(O)OCH$_2$C(CH$_3$)$_2$—, —OCH$_2$(CH$_2$)$_p$—, —OC(CH$_3$)$_2$CH$_2$CH$_2$—, —OCH$_2$C(CH$_3$)$_2$CH$_2$—, —OCH$_2$CH$_2$C(CH$_3$)$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, —OCH$_2$CH$_2$C(O)CH$_2$—, or a group of the formula

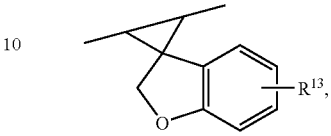

where $R^a$ is as previously defined,
or, where they are attached to adjacent carbon atoms, $R^{10}$ and $R^{11}$ may together represent —OCH$_2$CH$_2$— or —OCH$_2$CH(OH)—, or $R^{10}$ and $R^{11}$ may together form a fused benzene ring;
or, $R^{10}$ and $R^{11}$ together form a $C_{1-2}$alkylene bridge across the pyrrolidine, piperidine, morpholine or piperazine ring to which they are attached;
$R^{12}$ represents hydrogen, benzyl, $C_{1-6}$alkyl, $C_{3-7}$cycloalkyl, $C_{3-7}$cycloalkyl$C_{1-4}$alkyl, $COC_{1-6}$alkyl, $CO_2C_{1-6}$alkyl or $C_{2-4}$alkyl substituted by a $C_{1-4}$alkoxy or hydroxyl group;
$R^{13}$ represents hydrogen, halogen, hydroxy, $C_{1-4}$alkyl, hydroxy$C_{1-4}$alkyl or fluoro$C_{1-4}$alkyl;
m is 1 or 2;
p is 1, 2 or 3; and
q is zero, 1 or 2;
wherein when W is

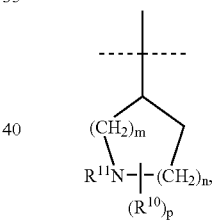

$R^{10}$ represents halogen, hydroxy, $C_{1-4}$alkoxy or fluoro$C_{1-4}$alkoxy, or where p is 2, then two $R^{10}$ groups may together represent an oxo (=O) group;
$R^{11}$ represents hydrogen, benzyl, $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;
m is zero, 1 or 2;
n is zero or 1, with the proviso that the sum total of m+n is 1, 2 or 3, and with the further proviso that when m is 2 then n is 1; and
p is zero, 1 or 2;
wherein when W is

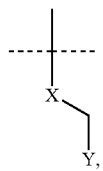

X represents —CHF—, —CF$_2$—, —CH(OH)— or —CH(OC$_{1-4}$alkyl)-;

Y represents —NR$^{13}$R$^{14}$ or a group selected from:

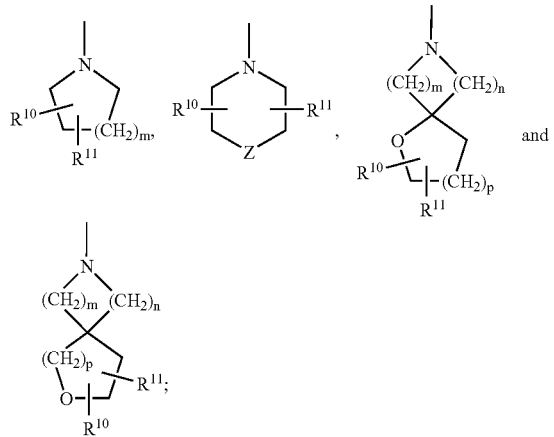

Z represents O, S, SO, SO$_2$ or NR$^{12}$;
R$^{10}$ represents hydrogen, halogen, hydroxy, C$_{1-4}$alkoxy or fluoroC$_{1-4}$alkoxy;
R$^{11}$ represents hydrogen, halogen, hydroxy, C$_{1-4}$alkoxy or fluoroC$_{1-4}$alkoxy;
or R$^{10}$ and R$^{11}$ together represent an oxo (=O) group;
R$^{12}$ represents C$_{1-6}$alkyl, COC$_{1-6}$alkyl, CO$_2$C$_{1-6}$alkyl;
R$^{13}$ and R$^{14}$ each independently represent hydrogen, C$_{1-6}$alkyl, C$_{3-7}$cycloalkyl or fluoroC$_{1-6}$alkyl, wherein said alkyl or cycloalkyl groups are optionally substituted with a group selected from hydroxy, C$_{1-4}$alkoxy, —NHCOC$_{1-4}$alkyl or —NHCO$_2$C$_{1-4}$alkyl;
m is 1 or 2;
n is 1 or 2; and
p is 1 or 2;
wherein when W is

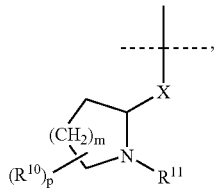

X represents —CHR$^{13}$—, CF$_2$— or —C(=O)—;
R$^{10}$ represents halogen, hydroxy, C$_{1-4}$alkoxy or fluoroC$_{1-4}$alkoxy, or where p is 2, then two R$^{10}$ groups may together represent an oxo (=O) group;
R$^{11}$ represents hydrogen, benzyl, C$_{1-6}$alkyl, C$_{3-7}$cycloalkyl, C$_{3-7}$cycloalkylC$_{1-4}$alkyl, COC$_{1-6}$alkyl, CO$_2$C$_{1-6}$alkyl or C$_{2-4}$alkyl substituted by a C$_{1-4}$alkoxy or hydroxyl group;
R$^{12}$ represents hydrogen, fluorine, hydroxy, C$_{1-4}$alkoxy, or R$^{12}$ is linked to R$^{11}$ such that there is formed a ring, the linkage —R$^{12}$—R$^{11}$— being selected from:
(a) —OC(O)—,
(b) —OS(O)$_2$—,
(c) -ZCH$_2$CH$_2$—,
(d) -ZCH$_2$CH$_2$CH$_2$—,
(e) -ZCH$_2$C(O)—,
(f) -ZCH$_2$CH$_2$C(O)—,
(g) -ZC(O)CH$_2$—,
(h) -ZC(O)CH$_2$CH$_2$—, and
(i) -ZCH$_2$C(O)CH$_2$—;
wherein Z represents O, NH or N(C$_{1-6}$alkyl);
m is 1 or 2; and
p is zero, 1 or 2.

One favoured group of compounds of the present invention are those of the formula (Ia) and pharmaceutically acceptable salts thereof:

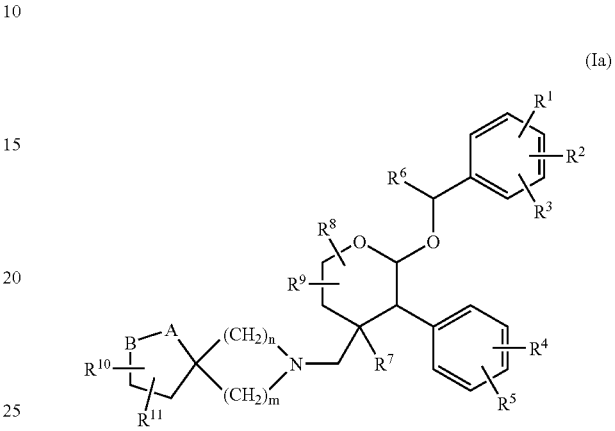

(Ia)

wherein R$^1$, R$^2$, R$^3$, R$^4$, R$^5$, R$^6$, R$^7$, R$^8$ and R$^9$ as hereinbefore defined, and A, B, R$^{10}$, R$^{11}$, m and n are as hereinbefore defined as for when W is

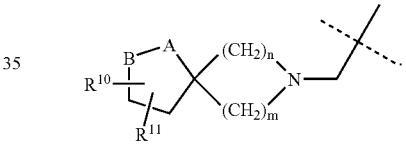

A preferred class of compounds of formula (Ia) is that wherein R$^1$ is hydrogen, C$_{1-4}$alkyl, C$_{1-4}$alkoxy, halogen or CF$_3$.

Another preferred class of compounds of formula (Ia) is that wherein R$^2$ is hydrogen, C$_{1-4}$alkyl, C$_{1-4}$alkoxy, halogen or CF$_3$.

A particularly preferred class of compounds of formula (Ia) is that wherein R$^1$ is fluorine, chlorine, methyl or CF$_3$.

Another particularly preferred class of compounds of formula (Ia) is that wherein R$^2$ is hydrogen, fluorine, chlorine, methyl or CF$_3$.

Also particularly preferred is the class of compounds of formula (Ia) wherein R$^3$ is hydrogen, fluorine, chlorine, methyl or CF$_3$.

Preferably R$^1$ and R$^2$ are in the 3 and 5 positions of the phenyl ring.

More preferably R$^1$ is 3-fluoro, 3-chloro, 3-methyl or 3-CF$_3$.

More preferably R$^2$ is 5-fluoro, 5-chloro, 5-methyl or 5-CF$_3$.

More preferably R$^3$ is hydrogen.

Most preferably R$^1$ is 3-F or 3-CF$_3$, R$^2$ is 5-CF$_3$ and R$^3$ is hydrogen.

A further preferred class of compound of formula (Ia) is that wherein R$^4$ is fluorine or hydrogen.

Another preferred class of compounds of formula (Ia) is that wherein R$^5$ is hydrogen, fluorine, chlorine, bromine or CF$_3$.

Preferably $R^4$ is hydrogen or 3-fluoro and $R^5$ is hydrogen or 4-fluoro.

$R^6$ is preferably $C_{1-4}$alkyl optionally substituted by hydroxy. In particular, $R^6$ is preferably a methyl or hydroxymethyl group.

Another preferred class of compound of formula (Ia) is that wherein $R^7$ is hydrogen or methyl, and especially hydrogen.

A further preferred class of compound of formula (Ia) is that wherein one of $R^8$ and $R^9$ is hydrogen, and especially wherein $R^8$ and $R^9$ are both hydrogen atoms.

Another preferred class of compound of formula (Ia) is that wherein $R^{10}$ represents hydroxy, $C_{1-4}$alkyl or $C_{1-4}$alkoxy.

A further preferred class of compound of formula (Ia) is that wherein $R^{11}$ represents hydrogen or methyl.

A particularly preferred class of compound of formula (Ia) is that wherein $R^{10}$ represents hydroxy and $R^{11}$ represents hydrogen or methyl (especially hydrogen), where both $R^{10}$ and $R^{11}$ are attached to the same carbon atom, or alternatively $R^{10}$ and $R^{11}$ together represent an oxo group.

A further preferred class of compound of formula (Ia) is that wherein A is $CH_2$ and B is an oxygen atom. When A is $CH_2$ and B is an oxygen atom it is preferred that the groups $R^{10}$ and $R^{11}$ are not adjacent to B.

Another preferred class of compound of formula (Ia) is that wherein n is 2 and m is 2.

Also preferred are the classes of compound of formula (Ia) wherein n is 1 and m is 3; or n is 1 and m is 2; or n is 1 and m is 1.

One favoured group of compounds of the formula (Ia) are those of the formula (Iaa) and pharmaceutically acceptable salts thereof:

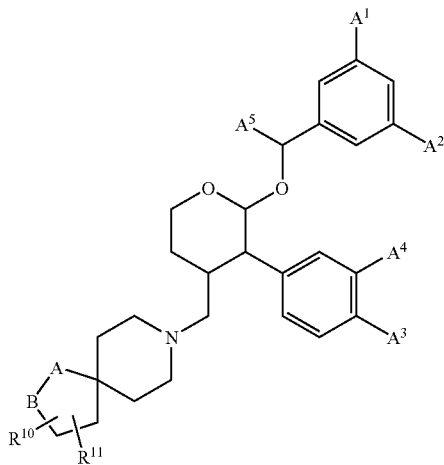

(Iaa)

wherein
$A^1$ is fluorine or $CF_3$;
$A^2$ is fluorine or $CF_3$;
$A^3$ is hydrogen or fluorine;
$A^4$ is hydrogen, fluorine or bromine;
$A^5$ is methyl or hydroxymethyl; and
A, B, $R^{10}$ and $R^{11}$ are as defined in relation to formula (Ia).

Another favoured group of compounds of the formula (Ia) are those of the formula (Iab) and pharmaceutically acceptable salts thereof:

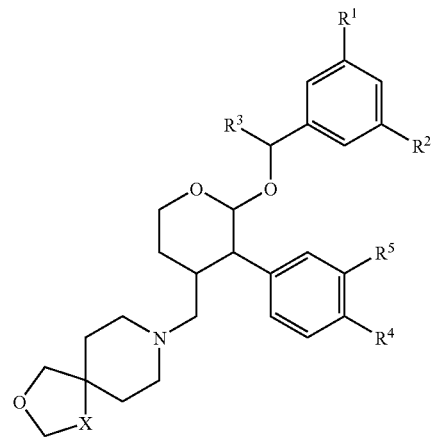

(Iab)

wherein
X represents CHOH or C=O;
$R^1$ is fluorine or trifluoromethyl;
$R^2$ is fluorine or trifluoromethyl;
$R^3$ is methyl or hydroxymethyl;
$R^4$ is hydrogen or fluorine; and
$R^5$ is hydrogen or fluorine;
and pharmaceutically acceptable salts thereof.

A preferred class of compounds of formula (Iab) is that wherein $R^1$ is trifluoromethyl.

Another preferred class of compounds of formula (Iab) is that wherein $R^2$ is trifluoromethyl.

Also particularly preferred is the class of compounds of formula (Iab) wherein $R^3$ is methyl.

A further preferred class of compounds of formula (Iab) is that wherein $R^4$ is fluorine.

Another preferred class of compounds of formula (Iab) is that wherein $R^5$ is hydrogen.

Another preferred class of compound of formula (Iab) is that wherein X is CHOH.

One favoured group of compounds of the formula (Iab) are those of the formula (Iaba) and pharmaceutically acceptable salts thereof:

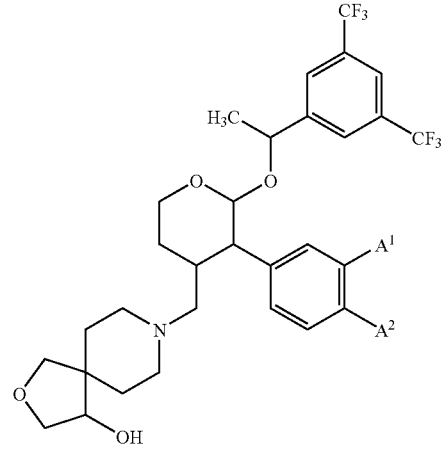

(Iaba)

wherein
A¹ is hydrogen or fluorine, especially hydrogen; and
A² is hydrogen or fluorine, especially fluorine.

Another favoured group of the compounds of the present invention are those of the formula (Ib) and pharmaceutically acceptable salts thereof:

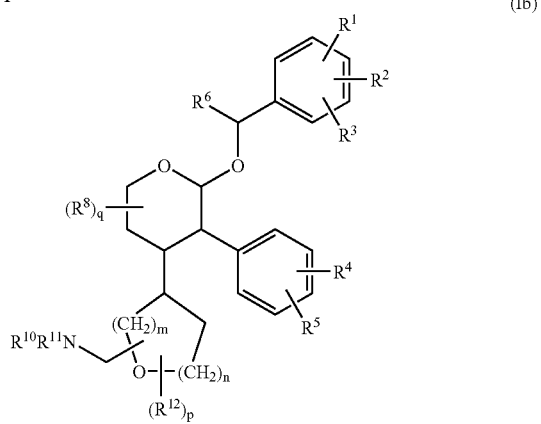

(Ib)

wherein R¹, R², R³, R⁴, R⁵ and R⁶ are hereinbefore defined; R¹⁰, R¹¹, R¹², m, n and p are as hereinbefore defined as for when W is

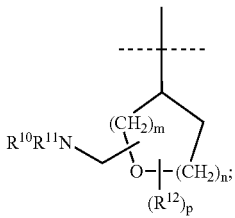

R⁸ represents halogen, $C_{1-6}$alkyl, $CH_2OR^c$, $CO_2R^a$ or $CONR^aR^b$, or where q is 2, then two R⁸ groups may together represent an oxo (=O) group, where $R^a$ and $R^b$ are as previously defined and $R^c$ represents hydrogen, $C_{1-6}$alkyl or phenyl; and q is zero, 1 or 2.

A preferred class of compounds of formula (Ib) is that wherein R¹ is hydrogen, $C_{1-4}$alkyl, $C_{1-4}$alkoxy, halogen or $CF_3$.

Another preferred class of compounds of formula (Ib) is that wherein R² is hydrogen, $C_{1-4}$alkyl, $C_{1-4}$alkoxy, halogen or $CF_3$.

A particularly preferred class of compounds of formula (Ib) is that wherein R¹ is fluorine, chlorine, methyl or $CF_3$.

Another particularly preferred class of compounds of formula (Ib) is that wherein R² is hydrogen, fluorine, chlorine, methyl or $CF_3$.

Also particularly preferred is the class of compounds of formula (Ib) wherein R³ is hydrogen, fluorine, chlorine, methyl or $CF_3$.

Preferably R¹ and R² are in the 3 and 5 positions of the phenyl ring.

More preferably R¹ is 3-fluoro, 3-chloro, 3-methyl or 3-$CF_3$.

More preferably R² is 5-fluoro, 5-chloro, 5-methyl or 5-$CF_3$.

More preferably R³ is hydrogen.

Most preferably R¹ is 3-F or 3-$CF_3$, R² is 5-$CF_3$ and R³ is hydrogen.

A further preferred class of compound of formula (Ib) is that wherein R⁴ is hydrogen or fluorine.

Another preferred class of compounds of formula (Ib) is that wherein R⁵ is hydrogen, fluorine, chlorine or $CF_3$.

Preferably R⁴ is hydrogen or 3-fluoro and R⁵ is hydrogen or 4-fluoro.

R⁶ is preferably $C_{1-4}$alkyl optionally substituted by hydroxy. In particular, R⁶ is preferably a methyl or hydroxymethyl group. Most especially, R⁶ is a methyl group.

A further preferred class of compounds of formula (Ib) is that wherein R¹⁰ is hydrogen, $C_{1-4}$alkyl or a $C_{2-4}$alkyl group substituted by a hydroxyl or $C_{1-2}$alkoxy group.

Another preferred class of compounds of formula (Ib) is that wherein R¹¹ is hydrogen, $C_{1-4}$alkyl, or a benzyl group.

Where R¹⁰ and R¹¹ are linked so that, together with the nitrogen atom to which they are attached, they form a heteroaliphatic ring, suitable rings include azetidinyl, pyrrolidinyl, piperidinyl, morpholino, thiomorpholino, piperazino or a piperazino group substituted on the nitrogen atom by a $C_{1-4}$alkyl group or a $C_{2-4}$alkyl group substituted by a hydroxy or $C_{1-2}$alkoxy group. Particularly preferred heteroaliphatic rings formed by —NR¹⁰R¹¹ are azetidine, pyrrolidine, piperidine, morpholine, piperazine and N-methylpiperazine.

Another preferred class of compounds of formula (Ib) is that wherein R¹² is fluorine, hydroxy, methoxy or ethoxy or, where p is 2, then the two R¹² groups together represent an oxo (=O) group.

Another preferred class of compounds of formula (Ib) is that wherein R⁸ is methyl.

Another preferred class of compounds of formula (Ib) is that wherein m is zero or 1 and n is 1 or 2. Most preferably, m is zero and n is 2.

Yet another preferred class of compounds of formula (Ib) is that wherein p is zero.

A further preferred class of compounds of formula (Ib) is that wherein q is zero.

It will be appreciated that where one or two R¹² groups are present, each group may replace any of the hydrogen atoms in the $(CH_2)_m$ and $(CH_2)_n$ groups. Similarly, the —CH²—NR¹⁰R¹¹ moiety may replace a hydrogen atom in either of the $(CH_2)_m$ and $(CH_2)_n$ groups.

One favoured group of compounds of the formula (Ib) are those of the formula (Iba) and pharmaceutically acceptable salts thereof:

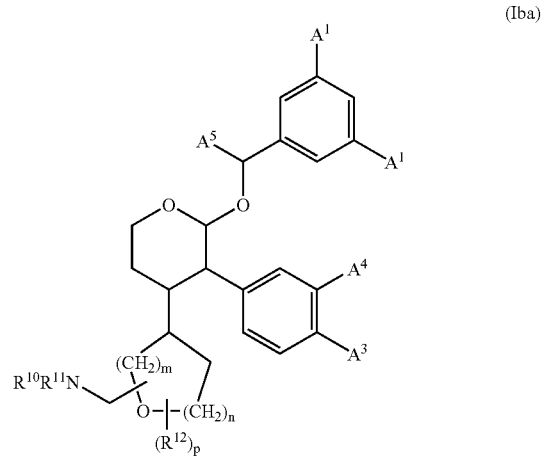

(Iba)

wherein
A¹ is fluorine or $CF_3$;
A² is fluorine or $CF_3$;
A³ is fluorine or hydrogen;
A⁴ is fluorine or hydrogen;
A⁵ is methyl; and
$R^{10}$, $R^{11}$, $R^{12}$, m, n and p are as defined in relation to formula (Ib).

Another favoured group of the compounds of the present invention are those of the formula (Ic) and pharmaceutically acceptable salts thereof:

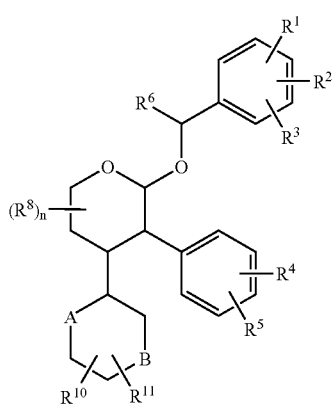

(Ic)

wherein $R^1$, $R^2$, $R^3$, $R^4$, $R^5$ and $R^6$ are as hereinbefore defined; A, B, $R^{10}$, $R^{11}$, $R^{12}$, $R^{13}$, m, p and q are as hereinbefore defined as for when W is

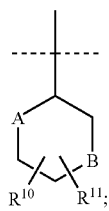

;

$R^8$ represents halogen, $C_{1-6}$alkyl, $CH_2OR^c$, $CO_2R^a$ or $CONR^aR^b$, or where n is 2, then two $R^8$ groups may together represent an oxo (=O) group, where $R^a$ and $R^b$ are as previously defined and $R^c$ represents hydrogen, $C_{1-6}$alkyl or phenyl; and n is zero, 1 or 2.

A preferred class of compounds of formula (Ic) is that wherein $R^1$ is hydrogen, $C_{1-4}$alkyl, $C_{1-4}$alkoxy, halogen or $CF_3$.

Another preferred class of compounds of formula (Ic) is that wherein $R^2$ is hydrogen, $C_{1-4}$alkyl, $C_{1-4}$alkoxy, halogen or $CF_3$.

A particularly preferred class of compounds of formula (Ic) is that wherein $R^1$ is fluorine, chlorine, methyl or $CF_3$.

Another particularly preferred class of compounds of formula (Ic) is that wherein $R^2$ is hydrogen, fluorine, chlorine, methyl or $CF_3$.

Also particularly preferred is the class of compounds of formula (Ic) wherein $R^3$ is hydrogen, fluorine, chlorine, methyl or $CF_3$.

Preferably $R^1$ and $R^2$ are in the 3 and 5 positions of the phenyl ring.

More preferably $R^1$ is 3-fluoro, 3-chloro, 3-methyl or 3-$CF_3$.

More preferably $R^2$ is 5-fluoro, 5-chloro, 5-methyl or 5-$CF_3$.

More preferably $R^3$ is hydrogen.

Most preferably $R^1$ is 3-F or 3-$CF_3$, $R^2$ is 5-$CF_3$ and $R^3$ is hydrogen.

A further preferred class of compound of formula (Ic) is that wherein $R^4$ is hydrogen or fluorine.

Another preferred class of compounds of formula (Ic) is that wherein $R^5$ is hydrogen, fluorine, chlorine or $CF_3$.

Preferably $R^4$ is hydrogen or 3-fluoro and $R^5$ is hydrogen or 4-fluoro.

$R^6$ is preferably $C_{1-4}$alkyl optionally substituted by hydroxy. In particular, $R^6$ is preferably a methyl or hydroxymethyl group. Most especially, $R^6$ is a methyl group.

Another preferred class of compounds of formula (Ic) is that wherein $R^{10}$ is hydrogen, hydroxy, $C_{1-2}$alkyl substituted by hydroxy, $C_{1-4}$alkoxy (especially methoxy) or $CO_2R^e$ (where $R^e$ is hydrogen, methyl ethyl or benzyl). Particularly preferred are compounds of formula (Ic) where $R^{10}$ is hydrogen.

A further preferred class of compounds of formula (Ic) is that wherein $R^{11}$ is hydrogen or $C_{1-4}$alkyl (especially methyl). Particularly preferred are compounds of formula (I) where $R^{11}$ is hydrogen.

$R^{10}$ and $R^{11}$ are preferably attached to the same carbon atom thus forming a moiety of the formula $CR^{10}R^{11}$. Where $R^{10}$ and $R^{11}$ are attached to the same carbon atom they may, in particular, together represent —$C(O)OCH_2CH_2$—.

In a further preferred class of compounds of formula (Ic), $R^{12}$ preferably represents hydrogen, methyl or ethyl.

Another preferred class of compounds of formula (Ic) is that wherein $R^8$ is methyl.

A further preferred class of compounds of formula (Ic) is that wherein n is zero.

A further preferred class of compounds of formula (Ic) is that wherein A is $NR^{12}$ and B is $S(O)_q$.

Preferably, q is zero.

One favoured group of compounds of the formula (Ic) are those of the formula (Ica) and pharmaceutically acceptable salts thereof:

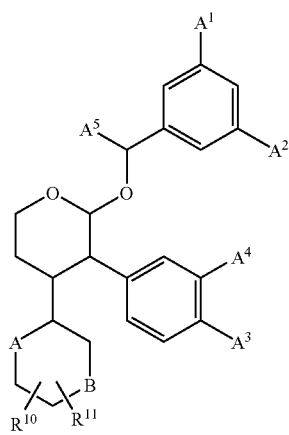

(Ica)

wherein
A$^1$ is fluorine or CF$_3$;
A$^2$ is fluorine or CF$_3$;
A$^3$ is fluorine or hydrogen;
A$^4$ is fluorine or hydrogen;
A$^5$ is methyl; and
A, B, R$^{10}$ and R$^{11}$ are as defined in relation to formula (Ic).

Another favoured group of the compounds of the present invention are those of the formula (Id) and pharmaceutically acceptable salts thereof:

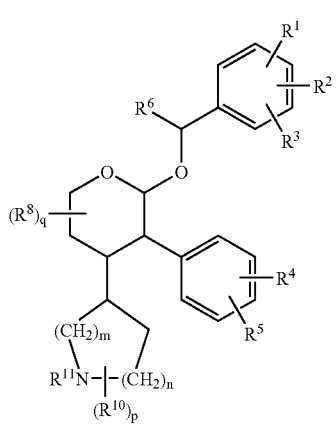

(Id)

wherein R$^1$, R$^2$, R$^3$, R$^4$, R$^5$ and R$^6$ are as hereinbefore defined; R$^{10}$, R$^{11}$, m, n and p are as hereinbefore defined as for when W is

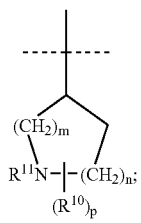

R$^8$ represents halogen, C$_{1-6}$alkyl, CH$_2$OR$^c$, CO$_2$R$^a$ or CONR$^a$R$^b$, or where q is 2, then two R$^8$ groups may together represent an oxo (=O) group, where R$^a$ and R$^b$ are as previously defined and R$^c$ represents hydrogen, C$_{1-6}$alkyl or phenyl; and q is zero, 1 or 2.

A preferred class of compounds of formula (Id) is that wherein R$^1$ is hydrogen, C$_{1-4}$alkyl, C$_{1-4}$alkoxy, halogen or CF$_3$.

Another preferred class of compounds of formula (Id) is that wherein R$^2$ is hydrogen, C$_{1-4}$alkyl, C$_{1-4}$alkoxy, halogen or CF$_3$.

A particularly preferred class of compounds of formula (Id) is that wherein R$^1$ is fluorine, chlorine, methyl or CF$_3$.

Another particularly preferred class of compounds of formula (Id) is that wherein R$^2$ is hydrogen, fluorine, chlorine, methyl or CF$_3$.

Also particularly preferred is the class of compounds of formula (Id) wherein R$^3$ is hydrogen, fluorine, chlorine, methyl or CF$_3$.

Preferably R$^1$ and R$^2$ are in the 3 and 5 positions of the phenyl ring.

More preferably R$^1$ is 3-fluoro, 3-chloro, 3-methyl or 3-CF$_3$.

More preferably R$^2$ is 5-fluoro, 5-chloro, 5-methyl or 5-CF$_3$.

More preferably R$^3$ is hydrogen.

Most preferably R$^1$ is 3-F or 3-CF$_3$, R$^2$ is 5-CF$_3$ and R$^3$ is hydrogen.

A further preferred class of compound of formula (Id) is that wherein R$^4$ is hydrogen or fluorine.

Another preferred class of compounds of formula (Id) is that wherein R$^5$ is hydrogen, fluorine, chlorine or CF$_3$.

Preferably R$^4$ is hydrogen or 3-fluoro and R$^5$ is hydrogen or 4-fluoro.

R$^6$ is preferably C$_{1-4}$alkyl optionally substituted by hydroxy. In particular, R$^6$ is preferably a methyl or hydroxymethyl group. Most especially, R$^6$ is a methyl group.

Another preferred class of compounds of formula (Id) is that wherein R$^{10}$ is fluorine, hydroxy, methoxy or ethoxy or, where p is 2, then the two R$^{10}$ groups together represent an oxo (=O) group.

In a further preferred class of compounds of formula (Id), R$^{11}$ preferably represents hydrogen, methyl or ethyl.

Another preferred class of compounds of formula (Id) is that wherein R$^8$ is methyl.

Another preferred class of compounds of formula (Id) is that wherein m is zero or 1 and n is zero or 1, and the sum total of m+n is 1. Most preferably, m is zero and n is 1.

A further preferred class of compound of formula (Id) is that wherein m is 2 and n is 1.

Yet another preferred class of compounds of formula (Id) is that wherein p is zero.

A further preferred class of compounds of formula (Id) is that wherein q is zero.

It will be appreciated that where one or two R$^{10}$ groups are present, each group may replace any of the hydrogen atoms in the (CH$_2$)$_m$ and (CH$_2$)$_n$ groups.

One favoured group of compounds of the formula (Id) are those of the formula (Ida) and pharmaceutically acceptable salts thereof:

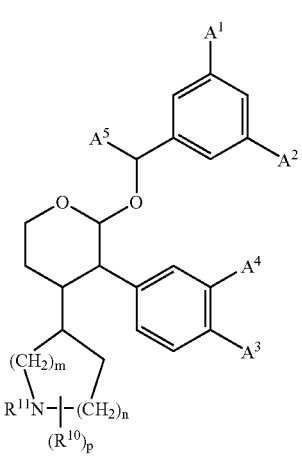

(Ida)

wherein
A$^1$ is fluorine or CF$_3$;
A$^2$ is fluorine or CF$_3$;
A$^3$ is fluorine or hydrogen;
A$^4$ is fluorine or hydrogen;
A$^5$ is methyl; and $R^{10}$, $R^{11}$, m, n and p are as defined in relation to formula (Id).

Another favoured group of the compounds of the present invention are those of formula (Ie) and pharmaceutically acceptable salts thereof:

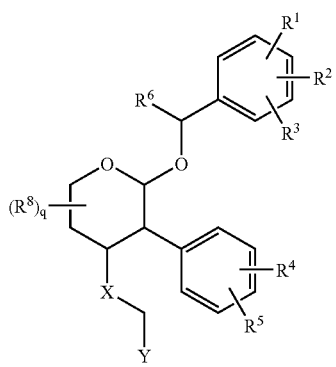

(Ie)

wherein $R^1$, $R^2$, $R^3$, $R^4$, $R^5$ and $R^6$ are as hereinbefore defined; X Y, Z, $R^{10}$, $R^{11}$, $R^{12}$, $R^{13}$, $R^{14}$, m, n and p are as hereinbefore defined as for when W is

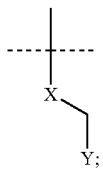

$R^8$ represents halogen, $C_{1-6}$alkyl, $CH_2OR^c$, $CO_2R^a$ or $CONR^aR^b$, or where q is 2, then two $R^8$ groups may together represent an oxo (=O) group, where $R^a$ and $R^b$ are as previously defined and $R^c$ represents hydrogen, $C_{1-6}$alkyl or phenyl; and q is zero, 1 and 2.

A preferred class of compounds of formula (Ie) is that wherein X is —CH(OH)—.

Another preferred class of compounds of formula (Ie) is that wherein Y is —$NR^{13}R^{14}$ (wherein $R^{13}$ and $R^{14}$ are preferably hydrogen or $C_{1-4}$alkyl) or the group

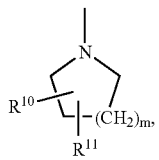

wherein $R^{10}$ and $R^{11}$ are preferably hydrogen and m is 1 or 2, and especially 2.

A further preferred class of compounds of formula (Ie) is that wherein Z is O, S or $NR^{12}$, especially where $R^{12}$ is a $C_{1-4}$alkyl group, such as methyl or ethyl.

A preferred class of compounds of formula (Ie) is that wherein $R^1$ is hydrogen, $C_{1-4}$alkyl, $C_{1-4}$alkoxy, halogen or $CF_3$.

Another preferred class of compounds of formula (Ie) is that wherein $R^2$ is hydrogen, $C_{1-4}$alkyl, $C_{1-4}$alkoxy, halogen or $CF_3$.

A particularly preferred class of compounds of formula (Ie) is that wherein $R^1$ is fluorine, chlorine, methyl or $CF_3$.

Another particularly preferred class of compounds of formula (Ie) is that wherein $R^2$ is hydrogen, fluorine, chlorine, methyl or $CF_3$.

Also particularly preferred is the class of compounds of formula (Ie) wherein $R^3$ is hydrogen, fluorine, chlorine, methyl or $CF_3$.

Preferably $R^1$ and $R^2$ are in the 3 and 5 positions of the phenyl ring.

More preferably $R^1$ is 3-fluoro, 3-chloro, 3-methyl or 3-$CF_3$.

More preferably $R^2$ is 5-fluoro, 5-chloro, 5-methyl or 5-$CF_3$.

More preferably $R^3$ is hydrogen.

Most preferably $R^1$ is 3-F or 3-$CF_3$, $R^2$ is 5-$CF_3$ and $R^3$ is hydrogen.

A further preferred class of compound of formula (Ie) is that wherein $R^4$ is hydrogen or fluorine.

Another preferred class of compounds of formula (Ie) is that wherein $R^5$ is hydrogen, fluorine, chlorine or $CF_3$.

Preferably $R^4$ is hydrogen or 3-fluoro and $R^5$ is hydrogen or 4-fluoro.

$R^6$ is preferably $C_{1-4}$alkyl optionally substituted by hydroxy. In particular, $R^6$ is preferably a methyl or hydroxymethyl group. Most especially, $R^6$ is a methyl group.

Another preferred class of compounds of formula (Ie) is that wherein $R^{10}$ is hydrogen, fluorine, hydroxy, methoxy or ethoxy and $R^{11}$ is hydrogen, or $R^{10}$ and $R^{11}$ are both fluorine or $R^{10}$ and $R^{11}$ together represent an oxo (=O) group.

Another preferred class of compounds of formula (Ie) is that wherein $R^8$ is methyl.

A further preferred class of compounds of formula (Ie) is that wherein $R^{12}$ is methyl, ethyl, acetyl, methoxycarbonyl or ethoxycarbonyl.

Another preferred class of compounds of formula (Ie) is that wherein $R^{13}$ and $R^{15}$ each independently represent hydrogen or $C_{1-4}$alkyl, and especially, methyl.

Another preferred class of compounds of formula (Ie) is that wherein m is 2.

A further preferred class is that wherein m is 2 and n is 2.

Yet another preferred class of compounds of formula (Ie) is that wherein p is 1.

A further preferred class of compounds of formula (Ie) is that wherein q is zero.

It will be appreciated that $R^{10}$ and $R^{11}$ may replace any of the hydrogen atoms in the $(CH_2)_m$ and $(CH_2)_p$ groups in the rings to which they are attached.

One favoured group of compounds of the formula (Ie) are those of the formula (Iea) and pharmaceutically acceptable salts thereof:

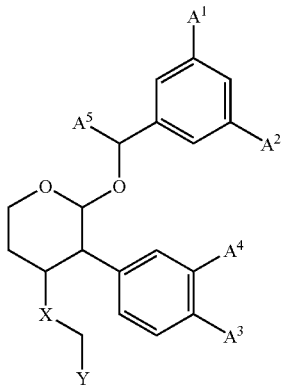

wherein
$A^1$ is fluorine or $CF_3$;
$A^2$ is fluorine or $CF_3$;
$A^3$ is fluorine or hydrogen;
$A^4$ is fluorine or hydrogen;
$A^5$ is methyl; and
X and Y are as defined in relation to formula (Ie).

Another favoured group of compounds of the present invention are those of formula (If) and pharmaceutically acceptable salts thereof:

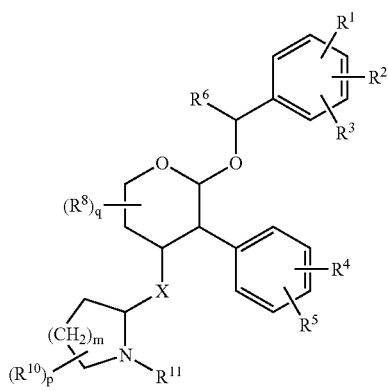

wherein $R^1$, $R^2$, $R^3$, $R^4$, $R^5$ and $R^6$ are as hereinbefore defined; X, $R^{10}$, $R^{11}$, $R^{12}$, m and p are as hereinbefore defined as for when W is

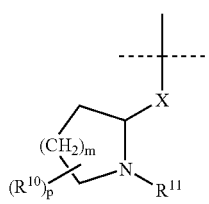

$R^8$ represents halogen, $C_{1-6}$alkyl, $CH_2OR^c$, $CO_2R^a$ or $CONR^aR^b$, or where q is 2, then two $R^8$ groups may together represent an oxo (=O) group, where $R^a$ and $R^b$ are as previously defined and $R^c$ represents hydrogen, $C_{1-6}$alkyl or phenyl; and q is zero, 1 or 2.

A preferred class of compounds of formula (If) is that wherein $R^1$ is hydrogen, $C_{1-4}$alkyl, $C_{1-4}$alkoxy, halogen or $CF_3$.

Another preferred class of compounds of formula (If) is that wherein $R^2$ is hydrogen, $C_{1-4}$alkyl, $C_{1-4}$alkoxy, halogen or $CF_3$.

A particularly preferred class of compounds of formula (If) is that wherein $R^1$ is fluorine, chlorine, methyl or $CF_3$.

Another particularly preferred class of compounds of formula (If) is that wherein $R^2$ is hydrogen, fluorine, chlorine, methyl or $CF_3$.

Also particularly preferred is the class of compounds of formula (If) wherein $R^3$ is hydrogen, fluorine, chlorine, methyl or $CF_3$.

Preferably $R^1$ and $R^2$ are in the 3 and 5 positions of the phenyl ring.

More preferably $R^1$ is 3-fluoro, 3-chloro, 3-methyl or 3-$CF_3$.

More preferably $R^2$ is 5-fluoro, 5-chloro, 5-methyl or 5-$CF_3$.

More preferably $R^3$ is hydrogen.

Most preferably $R^1$ is 3-F or 3-$CF_3$, $R^2$ is 5-$CF_3$ and $R^3$ is hydrogen.

A further preferred class of compound of formula (If) is that wherein $R^4$ is hydrogen or fluorine.

Another preferred class of compounds of formula (If) is that wherein $R^5$ is hydrogen, fluorine, chlorine or $CF_3$.

Preferably $R^4$ is hydrogen or 3-fluoro and $R^5$ is hydrogen or 4-fluoro.

$R^6$ is preferably $C_{1-4}$alkyl optionally substituted by hydroxy. In particular, $R^6$ is preferably a methyl or hydroxymethyl group. Most especially, $R^6$ is a methyl group.

Another preferred class of compounds of formula (If) is that wherein $R^{10}$ is fluorine, hydroxy, methoxy or ethoxy or, where p is 2, then the two $R^{10}$ groups together represent an oxo (=O) group.

In a further preferred class of compounds of formula (If), $R^{11}$ preferably represents hydrogen, methyl, ethyl or $CO_2$-tert-butyl.

Another preferred class of compounds of formula (If) is that wherein $R^8$ is methyl.

A further preferred class of compounds of formula (If) is that wherein X is —$CHR^{12}$—.

In particular, $R^{12}$ is preferably hydrogen or hydroxy.

Where $R^{12}$ is linked to $R^{11}$ such that there is formed a ring, the linkage —$R^{12}$—$R^{11}$— is preferably selected from:
(a) —OC(O)—,
(b) —OS(O)$_2$—,
(c) -ZCH$_2$CH$_2$—,
(d) -ZCH$_2$C(O)—,
(e) -ZC(O)CH$_2$—, wherein Z represents O, NH or N($C_{1-6}$alkyl). Most especially, where $R^{12}$ is linked to $R^{11}$ such that there is formed a ring, the linkage —$R^{12}$—$R^{11}$— is preferably —OC(O)—.

Another preferred class of compounds of formula (If) is that wherein m is 1.

Yet another preferred class of compounds of formula (If) is that wherein p is zero.

A further preferred class of compounds of formula (If) is that wherein q is zero.

It will be appreciated that where one or two $R^{10}$ groups are present, each group may replace any of the hydrogen atoms in the $(CH_2)_m$ groups.

One favoured group of compounds of the present invention are those of the formula (Ifa) and pharmaceutically acceptable salts thereof:

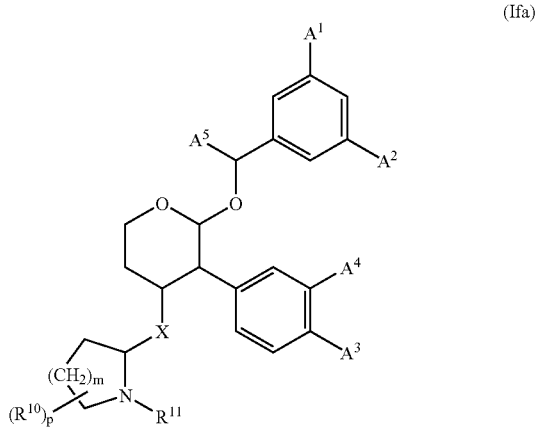

(Ifa)

wherein
$A^1$ is fluorine or $CF_3$;
$A^2$ is fluorine or $CF_3$;
$A^3$ is fluorine or hydrogen;
$A^4$ is fluorine or hydrogen;
$A^5$ is methyl; and
X, $R^{10}$, $R^{11}$, m and p are as defined in relation to formula (If).

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and "fluoro $C_{1-6}$ alkoxy" mean a $C_{1-6}$alkyl or $C_{1-6}$alkoxy group in which one or more (in particular, 1 to 3) hydrogen atoms have been replaced by fluorine atoms. Similarly, the term "fluoro$C_{1-4}$ alkyl" means a $C_{1-4}$alkyl group in which one or more (in particular 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group mean that the group is straight or branched. Examples of suitable alkenyl groups include vinyl and allyl. A suitable alkynyl group is propargyl.

When used herein the term "halogen" means fluorine, chlorine, bromine and iodine. The most apt halogens are fluorine and chlorine of which fluorine is preferred, unless otherwise stated.

Specific compounds within the scope of this invention include:
(4RS)-8-[(2R,3R,4R)-2-[(1R)-1-(3,5-bis(trifluoromethyl) phenyl)ethoxy]-3-phenyl-tetrahydropyran-4-yl]methyl-2-oxa-8-aza-spiro[4.5]decan-4-ol;
(4S)-8-[(2R,3R,4R)-2-[(1R)-1-(3,5-bis(trifluoromethyl) phenyl)ethoxy]-3-(4-fluorophenyl)tetrahydropyran-4-yl] methyl-2-oxa-8-aza-spiro[4.5]decan-4-ol;
(4R)-8-[(2R,3R,4R)-2-[(1R)-1-(3,5-bis(trifluoromethyl) phenyl)ethoxy]-3-(4-fluorophenyl)tetrahydropyran-4-yl] methyl-2-oxa-8-aza-spiro[4.5]decan-4-ol;
(4RS)-8-[(2R,3R,4R)-2-[(1R)-1-(3,5-bis(trifluoromethyl) phenyl)ethoxy]-3-(3,4-difluorophenyl)tetrahydropyran-4-yl]methyl-2-oxa-8-aza-spiro[4.5]decan-4-ol;
8-[(2R,3R,4R)-2-[(1R)-1-(3,5-bis(trifluoromethyl)phenyl) ethoxy]-3-(4-fluorophenyl)tetrahydropyran-4-yl]methyl-2-oxa-8-aza-spiro[4.5]decane;
8-[(2R,3S,4S)-2-[(1R)-1-(3,5-bis(trifluoromethyl)phenyl) ethoxy]-3-phenyl(tetrahydropyran-4-yl)]methyl-1,1-dimethyl-2-oxa-8-aza-spiro[4.5]decane;
8-[(2R,3S,4S)-2-[(1R)-1-(3,5-bis(trifluoromethyl)phenyl) ethoxy]-3-phenyl(tetrahydropyran-4-yl)]methyl-2,2-dimethyl-1-oxa-8-aza-spiro[4.5]decane;
8-[(2R,3S,4S)-2-[(1R)-1-(3,5-bis(trifluoromethyl)phenyl) ethoxy]-3-phenyl-tetrahydropyran-4-yl]methyl-1-oxa-8-aza-spiro[4.5]decane;
8-[(2R,3S,4S)-2-[(1R)-1-(3,5-bis(trifluoromethyl)phenyl) ethoxy]-3-phenyl-tetrahydropyran-4-yl]methyl-2-oxa-8-aza-spiro[4.5]decane;
8-[(2R,3R,4R)-2-[(1R)-1-(3,5-bis(trifluoromethyl)phenyl) ethoxy]-3-phenyl-tetrahydropyran-4-yl]methyl-2-oxa-8-aza-spiro[4.5]decane;
8-[(2R,3R,4R)-2-[(1R)-1-(3,5-bis(trifluoromethyl)phenyl) ethoxy]-3-phenyl-tetrahydropyran-4-yl]methyl-2,2-dimethyl-1-oxa-8-aza-spiro[4.5]decane;
8-[(2R,3R,4R)-2-[(1R)-1-(3,5-bis(trifluoromethyl)phenyl) ethoxy]-3-phenyl-tetrahydropyran-4-yl]methyl-1-oxa-8-aza-spiro[4.5]decane;
8-[(2R,3R,4R)-2-[(1R)-1-(3,5-bis(trifluoromethyl)phenyl) ethoxy]-3-phenyl-tetrahydropyran-4-yl]methyl-1,1-dimethyl-2-oxa-8-aza-spiro[4.5]decane;
8-[(2R,3R,4R)-2-[(1R)-1-(3,5-bis(trifluoromethyl)phenyl) ethoxy]-3-(4-fluorophenyl)tetrahydropyran-4-yl]methyl-2-oxa-8-aza-spiro[4.5]decan-4-one;
(4RS)-8-[(2R,3R,4R)-2-[(1R)-1-(3,5-bis(trifluoromethyl) phenyl)ethoxy]-3-(4-fluorophenyl)tetrahydropyran-4-yl] methyl-2-oxa-4-methyl-8-aza-spiro[4.5]decan-4-ol;
and pharmaceutically acceptable salts thereof.

Specific compounds within the scope of this invention also include:
(4R)-8-[(2R,3R,4R)-2-[(1R)-1-(3,5-bis(trifluoromethyl) phenyl)ethoxy]-3-(3-bromo-4-fluorophenyl)tetrahydro-pyran-4-yl]methyl-2-oxa-8-aza-spiro[4.5]decan-4-ol;
(4RS)-8-[(2R,3R,4R)-2-[(1R)-1-(3,5-bis(trifluoromethyl) phenyl)ethoxy]-(4-fluorophenyl)tetrahydropyran-4-yl] methyl-2-oxa-4-ethynyl-8-aza-spiro[4.5]decan-4-ol;
(8S)-2-[((2R,3R,4R)-2-[(1R)-1-[3,5-bis(trifluoromethyl) phenyl]ethoxy]-3-phenyl)tetrahydro-2H-pyran-4-yl)methyl]-6-oxa-2-azaspiro[3.4]octan-8-ol;
(8R)-2-[(((2R,3R,4R)-2-[(1R)-1-[3,5-bis(trifluoromethyl) phenyl]ethoxy]-3-phenyltetrahydro-2H-pyran-4-yl)methyl]-6-oxa-2-azaspiro[3.4]octan-8-ol;
(4RS)-8-[(2R,3R,4R)-2-[(1R)-1-(3,5-bis(trifluoromethyl) phenyl)ethoxy]-3-phenyltetrahydropyran-4-yl]methyl-1-oxa-8-azaspiro[4.5]decan-4-ol;

(4RS)-8-[(2R,3R,4R)-2-[(1R)-1-(3,5-bis(trifluoromethyl)phenyl)ethoxy]-3-(4-fluorophenyl)tetrahydropyran-4-yl]methyl-3,3-dimethyl-2-oxa-8-azaspiro[4.5]decan-4-ol;

(4R*)-8-[(2R,3R,4R)-2-[(1R)-1-(3,5-bis(trifluoromethyl)phenyl)ethoxy]-3-(4-fluorophenyl)tetrahydropyran-4-yl]methyl-1-oxa-8-azaspiro[4.5]decan-4-ol;

(4S*)-8-[(2R,3R,4R)-2-[(1R)-1-(3,5-bis(trifluoromethyl)phenyl)ethoxy]-3-(4-fluorophenyl)tetrahydropyran-4-yl]methyl-1-oxa-8-azaspiro[4.5]decan-4-ol;

(4R)-8-[((2R,3R,4R)-2-{(1R)-1-[3,5-bis(trifluoromethyl)phenyl]ethoxy}-3-phenyltetrahydro-2H-pyran-4-yl)methyl]-4-methoxy-2-oxa-8-azaspiro[4.5]decane;

(4R)-8-[((2R,3R,4R)-2-{(1R)-1-[3,5-bis(trifluoromethyl)phenyl]ethoxy}-3-(4-fluorophenyl)tetrahydro-2H-pyran-4-yl)methyl]-4-methoxy-2-oxa-8-azaspiro[4.5]decane;

8-[((2R,3R,4R)-2-{(1R)-1-[3,5-bis(trifluoromethyl)phenyl]ethoxy}-3-phenyltetrahydro-2H-pyran-4-yl)methyl]-1-oxa-8-azaspiro[4.5]decan-3-ol;

8-[((2R,3R,4R)-2-{(1R)-1-[3,5-bis(trifluoromethyl)phenyl]ethoxy}-3-phenyltetrahydro-2H-pyran-4-yl)methyl]-1-oxa-8-azaspiro[4.5]decan-3-one;

and pharmaceutically acceptable salts thereof.

Further specific compounds within the scope of this invention include:

(2R or S,5R or S)-5-((2R,3R,4R)-{(1R)-1-[3,5-bis(trifluoromethyl)phenyl]ethoxy}-tetrahydro-3-phenyl-2H-pyran-4-yl)tetrahydro-N-(phenylmethyl)-2-furanmethanamine;

(2S or R,5R or S)-5-((2R,3R,4R)-{(1R)-1-[3,5-bis(trifluoromethyl)phenyl]ethoxy}-tetrahydro-3-phenyl-2H-pyran-4-yl)tetrahydro-N-(phenylmethyl)-2-furanmethanamine;

(2R or S,5R or S)-5-((2R,3R,4R)-{(1R)-1-[3,5-bis(trifluoromethyl)phenyl]ethoxy}-tetrahydro-3-phenyl-2H-pyran-4-yl)tetrahydro-2-furanmethanamine;

(2S or R,5R or S)-5-((2R,3R,4R)-{(1R)-1-[3,5-bis(trifluoromethyl)phenyl]ethoxy}-tetrahydro-3-phenyl-2H-pyran-4-yl)-N,N-diethyltetrahydro-2-furanmethanamine;

and pharmaceutically acceptable salts thereof.

Specific compounds within the scope of this invention also include:

(3R or S)-3-((2R,3R,4R)-{(1R)-1-[3,5-bis(trifluoromethyl)phenyl]ethoxy}tetrahydro-3-phenyl-2H-pyran-4-yl)thiomorpholine; and (3S or R)-3-((2R,3R,4R)-{(1R)-1-[3,5-bis(trifluoromethyl)phenyl]ethoxy}tetrahydro-3-phenyl-2H-pyran-4-yl)thiomorpholine;

and pharmaceutically acceptable salts thereof.

Further specific compounds within the scope of this invention include:

(2S)-2-((2R,3R,4R)-{(1R)-1-[3,5-bis(trifluoromethyl)phenyl]ethoxy}tetrahydro-3-phenyl-2H-pyran-4-yl)-1-methylazetidine;

(2R)-2-((2R,3R,4R)-{(1R)-1-[3,5-bis(trifluoromethyl)phenyl]ethoxy}tetrahydro-3-phenyl-2H-pyran-4-yl)-1-methylazetidine;

4-((2R,3R,4R)-{(1R)-1-[3,5-bis(trifluoromethyl)phenyl]ethoxy}tetrahydro-3-phenyl-2H-pyran-4-yl)piperidin-4-ol;

4-((2R,3R,4R)-{(1R)-1-[3,5-bis(trifluoromethyl)phenyl]ethoxy}tetrahydro-3-phenyl-2H-pyran-4-yl)-1-cyclopropylpiperidin-4-ol; and 4-((2R,3R,4R)-{(1R)-1-[3,5-bis(trifluoromethyl)phenyl]ethoxy}tetrahydro-3-phenyl-2H-pyran-4-yl)-1-(1-methylethyl)piperidin-4-ol;

and pharmaceutically acceptable salts thereof.

Specific compounds within the scope of this invention also include:

(αR or S)-α-((2R,3R,4R)-{(1R)-1-[3,5-bis(trifluoromethyl)phenyl]ethoxy}tetrahydro-3-phenyl-2H-pyran-4-yl)-1-piperidineethanol;

(αS or R)-α-((2R,3R,4R)-{(1R)-1-[3,5-bis(trifluoromethyl)phenyl]ethoxy}tetrahydro-3-phenyl-2H-pyran-4-yl)-1-piperidineethanol; and (αR or S,2R,3R,4R)-2-{(1R)-1-[3,5-bis(trifluoromethyl)phenyl]ethoxy}tetrahydro-α-[(dimethylamino)methyl]-3-phenyl-2H-pyran-4-methanol;

and pharmaceutically acceptable salts thereof.

Further specific compounds within the scope of this invention include:

1,1-dimethylethyl(2R or S)-2-[(R or S)-((2R,3R,4R)-{(1R)-1-[3,5-bis(trifluoromethyl)phenyl]ethoxy}tetrahydro-3-phenyl-2H-pyran-4-yl)hydroxymethyl]-1-pyrrolidinecarboxylate;

(1R or S, 7aR or S)-1-((2R,3R,4R)-{(1R)-1-[3,5-bis(trifluoromethyl)phenyl]-ethoxy}tetrahydro-3-phenyl-2H-pyran-4-yl)tetrahydro-1H,3H-pyrrolo[1,2-c]oxazol-3-one; and (2R,3R,4R,αR or S)-α-[(2R or S)-2-pyrrolidinyl]-2-{(1R)-1-[3,5-bis(trifluoromethyl)phenyl]ethoxy}tetrahydro-3-phenyl-2H-pyran-4-methanol;

and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formulae (Ia) and (Iaa) will have the stereochemistry of the 2-, 3-, 4- and 8-positions as shown in formulae (Iac) and (Iad)

The preferred compounds of the formulae (Iab) and (Iaba) will have the stereochemistry of the 2-, 3-, 4- and 8-positions as shown in formulae (Iabb) and (Iabc)

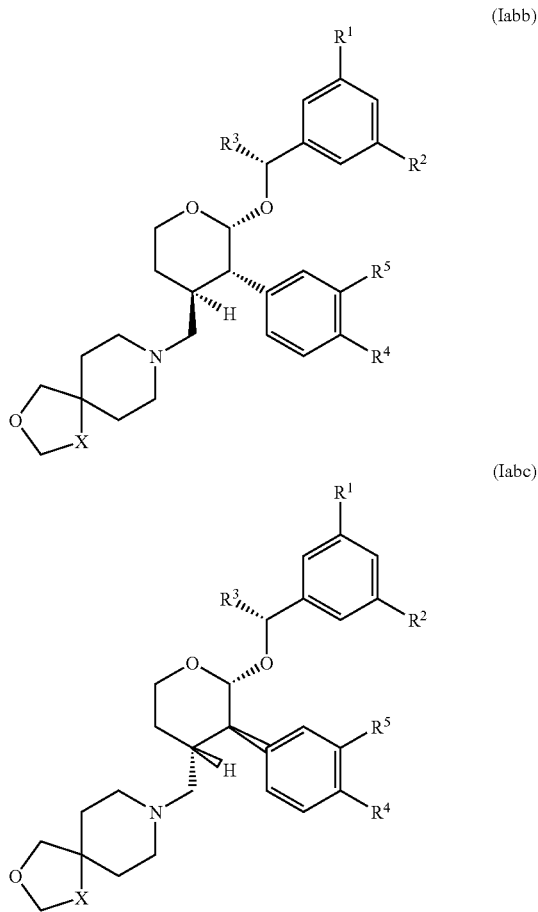

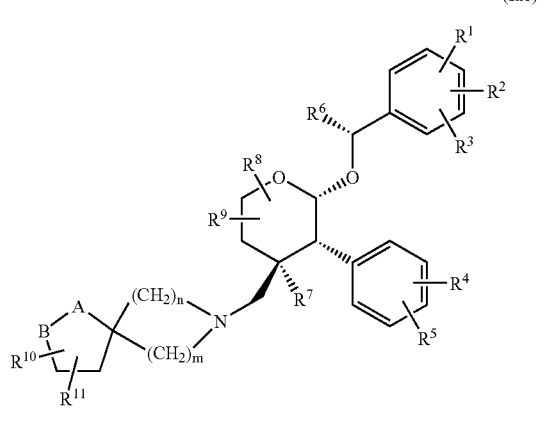

It will be appreciated that the preferred definitions of the various substituents recited herein may be taken alone or in combination and, unless otherwise stated, apply to the generic formula for compounds of the present invention as well as to the preferred classes of compound represented by formula (Iaba), formula (Iabb) and formula (Iabc).

The preferred compounds of the formulae (Ib), (Iba), (Id), (Ida), (Ie), (Iea), (If) and (Ifa) will have the stereochemistry of the 2-, 3-, 4- and 8-positions as shown in formula (Ig) and formula (Ih)

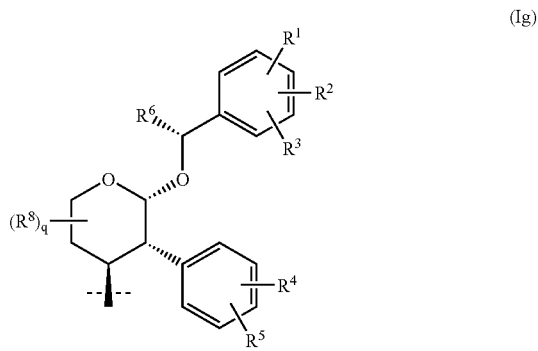

It will be appreciated that the preferred definitions of the various substituents recited herein may be taken alone or in combination and, unless otherwise stated, apply to the generic formula for compounds of the present invention as well as to the preferred classes of compound represented by formula (Iaa), formula (Iac) and formula (Iad).

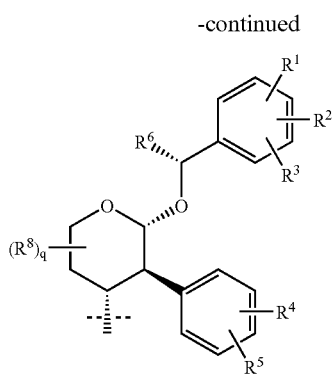

(Ih)

It will be appreciated that the preferred definitions of the various substituents recited herein may be taken alone or in combination and, unless otherwise stated, apply to the generic formula for compounds of formulae (Ib), (Id), (Ie) and (If) as well as to the preferred classes of compound represented by formulae (Iba), (Ida), (Iea), (Ifa), (Ig) and (Ih).

The preferred compounds of the formula (Ic) and (Ica) will have the stereochemistry of the 2-, 3-, 4- and 8-positions as shown in formula (Icb) and formula (Icc)

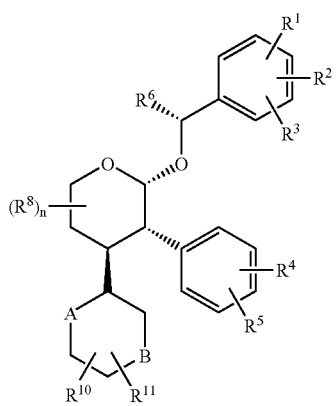

(Icb)

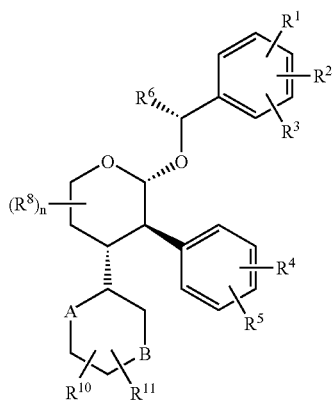

(Icc)

It will be appreciated that the preferred definitions of the various substituents recited herein may be taken alone or in combination and, unless otherwise stated, apply to the generic formula for compounds of formula (Ic) as well as to the preferred classes of compound represented by formula (Ica), formula (Icb) and formula (Icc).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

A more detailed description of pharmaceutical compositions that are suitable for the formulation of compounds of the present invention is disclosed in U.S. Pat. No. 6,071,927, the content of which is incorporated herein by reference (see in particular, column 8, line 50 to column 10, line 4).

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. A comprehensive listing of clinical conditions, uses and methods of treatment for which the compounds of the present invention will be useful is disclosed in U.S. Pat. No. 6,071,927, the content of which is incorporated herein by reference (see, in particular, column 10, line 14 to column 22, line 18).

In particular, the compounds of the present invention are useful in the treatment of a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, and anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

The compounds of the present invention are also particularly useful in the treatment of nociception and pain. Diseases and conditions in which pain predominates, include soft tissue and peripheral damage, such as acute trauma, osteoarthritis, rheumatoid arthritis, musculo-skeletal pain, particularly after trauma, spinal pain, myofascial pain syndromes, headache, migraine, episiotomy pain, and burns.

The compounds of the present invention are also particularly useful in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; in the treatment of inflammatory diseases such as inflammatory bowel disease, psoriasis, fibrositis, osteoarthritis, rheumatoid arthritis, pruritus and sunburn; and in the treatment of allergic disorders such as eczema and rhinitis.

The compounds of the present invention are also particularly useful in the treatment of gastrointestinal (GI) disorders, including inflammatory disorders and diseases of the GI tract such as ulcerative colitis, Crohn's disease and irritable bowel syndrome.

The compounds of the present invention are also particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy; by radiation including radiation therapy such as in the treatment of cancer; and in the treatment of post-operative nausea and vomiting.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

As used herein, the term "treatment" includes prophylactic use to prevent the occurrence or recurrence of any of the aforementioned conditions.

According to a general process (Aa), compounds of formula (Ia) may be prepared by the reaction of a compound of formula (IIa)

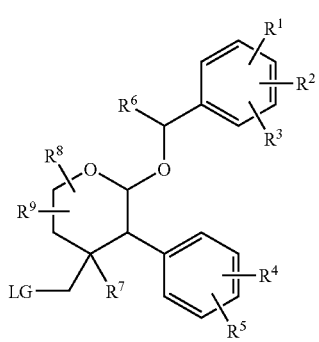

(IIa)

wherein LG is a suitable leaving group such as an alkyl- or arylsulfonyloxy group (e.g. mesylate or tosylate) or a halogen atom (e.g. bromine, chlorine or iodine); by reaction with an amine of formula (IIIa)

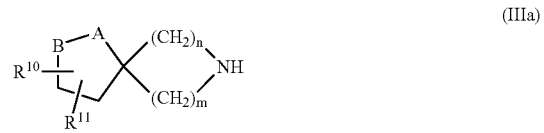

(IIIa)

The reaction is preferably effected in the presence of a base, for example, an alkali metal carbonate, such as potassium carbonate, in a suitable organic solvent such as acetonitrile. The reaction ideally is performed at an elevated temperature, for example, between 40° C. and 80° C., especially between 50° C. and 70° C.

A particularly preferred compound of formula (IIa) is that wherein the group LG is mesylate, i.e. the group —OSO$_2$CH$_3$, which compound is prepared by reaction of the corresponding methanol with methanesulfonyl chloride in the presence of a base, such as triethylamine, and optionally a catalyst such as 4-N,N-dimethylaminopyridine. The reaction is conveniently effected in a solvent such as a halogenated hydrocarbon, for example, dichloromethane.

Using general process (Aa), compounds of formula (Iab) may be prepared by the reaction of a compound of formula (IIab)

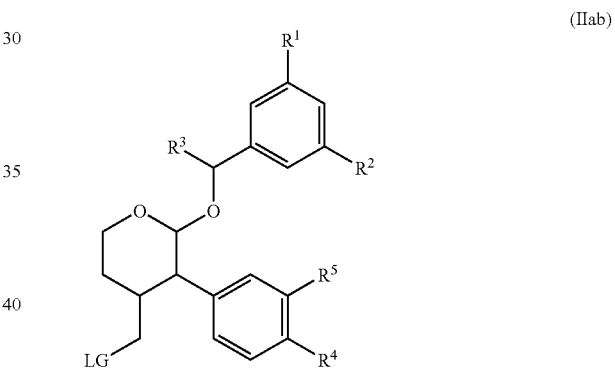

(IIab)

wherein LG is a suitable leaving group such as an alkyl- or arylsulfonyloxy group (e.g. mesylate or tosylate) or a halogen atom (e.g. bromine, chlorine or iodine); by reaction with an amine of formula (IIIab)

(IIIab)

A particularly preferred compound of formula (IIab) is that wherein the group LG is mesylate, i.e. the group —OSO$_2$CH$_3$, which compound is prepared by reaction of the corresponding methanol with methanesulfonyl chloride in the presence of a base, such as triethylamine, and optionally a catalyst such as 4-N,N-dimethylaminopyridine. The reaction is conveniently effected in a solvent such as a halogenated hydrocarbon, for example, dichloromethane.

According to another general process (Ba), compounds of formula (Ia) may be prepared by the reaction of an amine of formula (IIIa) with a compound of formula (IVa)

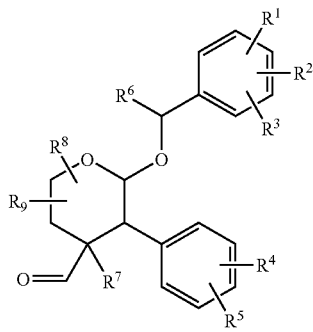

(IVa)

in the presence of a reducing agent, for example, sodium triacetoxyborohydride or sodium cyanoborohydride. The reaction is conveniently effected in a suitable solvent such as a halogenated hydrocarbon, for example, 1,2-dichloroethane, conveniently at about room temperature.

Further details of suitable procedures will be found in the accompanying Examples.

Using general process (Ba), compounds of formula (Iab) may be prepared by the reaction of an amine of formula (IIIab) with a compound of formula (IVab)

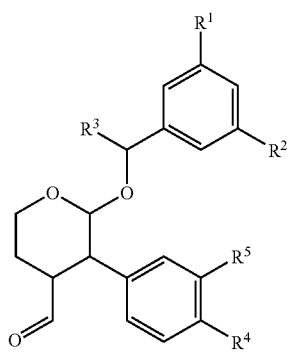

(IVab)

in the presence of a reducing agent, for example, sodium triacetoxyborohydride or sodium cyanoborohydride. The reaction is conveniently effected in a suitable solvent such as a halogenated hydrocarbon, for example, 1,2-dichloroethane, conveniently at about room temperature.

Further details of suitable procedures will be found in the accompanying Examples.

Compounds of formulae (IIa) and (IIab) may be prepared by conventional methods such as those described in International (PCT) Patent Publication No. WO 00/56727.

Compounds of formula (IIIa), and compounds of formula (IIIab) wherein X is CHOH, may be prepared from a suitably substituted precursor piperidine compound, for instance, as shown in Scheme 1 (in which R is, for example, a $C_{1-6}$alkyl group, such as an ethyl group, and P is an amino protecting group, such as a benzyloxycarbonyl group):

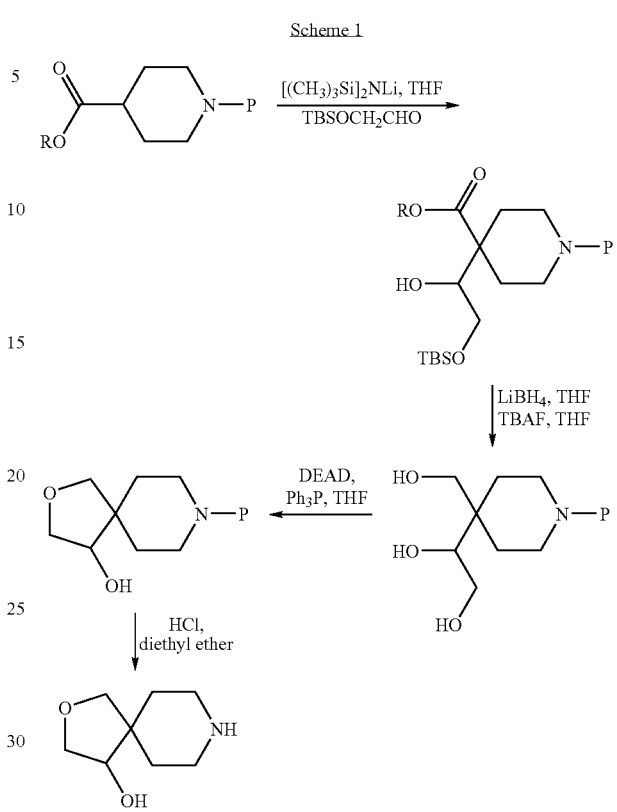

An alternative (asymmetric) synthesis of compounds of formula (IIIa), and compounds of formula (IIIab) wherein X is CHOH, is shown in Scheme 2:

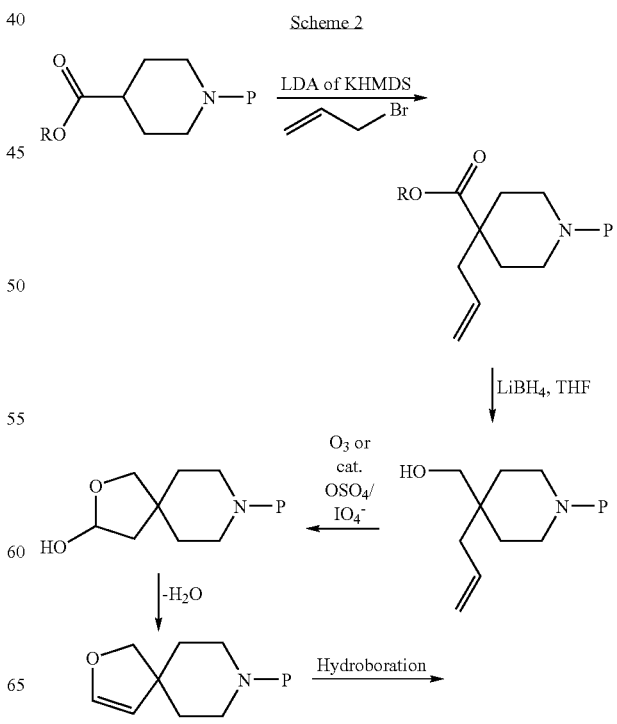

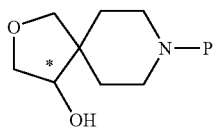

A further alternative (asymmetric) synthesis of compounds of formula (Ia), and compounds of formula (IIIab) wherein X is CHOH, is shown in Scheme 3:

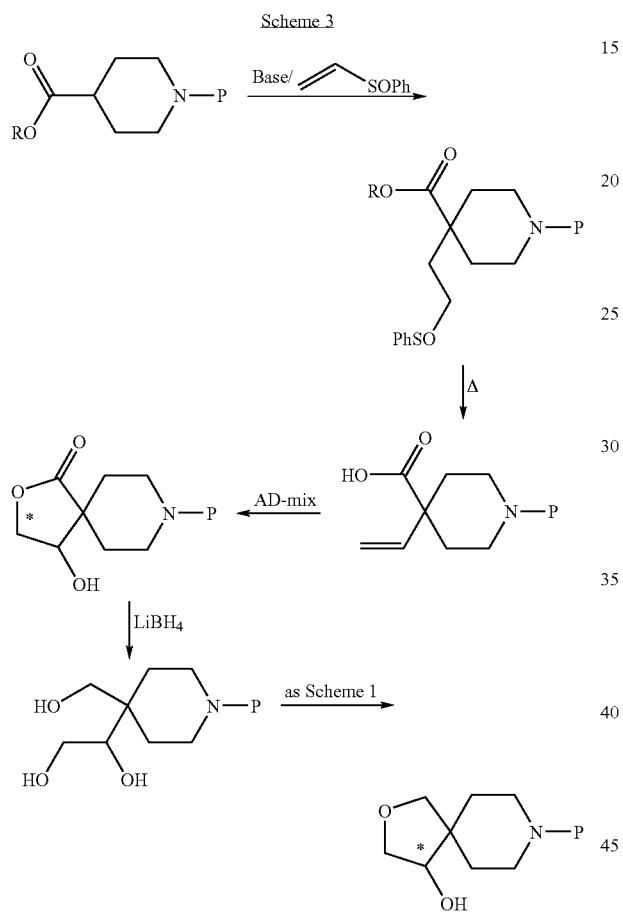

It will be appreciated that numerous other routes will be readily apparent to one of ordinary skill in the art, the route of choice depending upon the particular spiro-amine that is desired. The methodology described herein may be adapted accordingly. Thus, for instance, in addition to the processes outlined in Schemes 1, 2 and 3 above, amines of formula (IIIa) may be prepared by other methods that would be readily apparent to one of ordinary skill in the art. For example, methods for the preparation of the spirocyclic amines are provided in the literature—see for instance, *Bioorg. Med. Chem. Lett.,* 12 (2002) 1759-62 and International (PCT) Patent Publication No. WO 01/87838.

Compounds of formulae (IVa) and (IVab) may be prepared by conventional methods such as those described in International (PCT) Patent Publication No. WO 00/56727, for instance, by the oxidation of a corresponding vinyl compound using oxygen and ozone. The reaction is conveniently effected at a reduced temperature, such as at about −78° C., in the presence of an organic solvent such as an alcohol, for example, methanol, or a halogenated hydrocarbon, for example, dichloromethane, or a mixture thereof. Treatment with dimethylsulfide liberates the desired aldehyde.

According to a general process (Ab), compounds of formula (Ib) in which m is zero and n is 2 or 3 may be prepared by the cyclization of a compound of formula (IIb) in the presence of an amine of the formula $R^{10}R^{11}NH$:

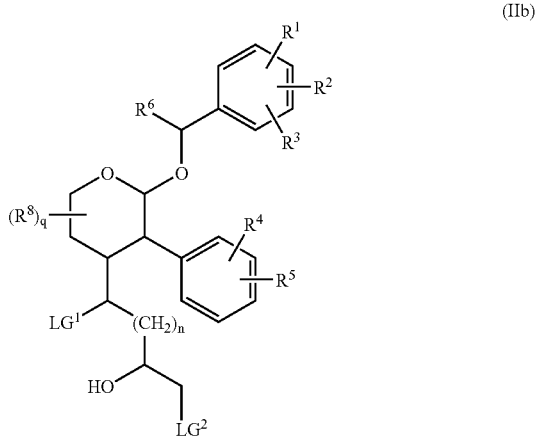

wherein $LG^1$ and $LG^2$ are independently leaving groups, such as mesylate, tosylate, brosylate, nosylate or triflate. Conveniently, $LG^1$ and $LG^2$ may be the same or different, for instance $LG^1$ may be mesylate whilst $LG^2$ may be tosylate.

The reaction is effected at an elevated temperature, for example, between 120° and 160° C., preferably at about 140° C., in a suitable solvent, such as an alcohol, for instance, methanol.

According to another general process (Bb), compounds of formula (Ib) in which m is 1 and n is 1 or 2 may be prepared by the cyclization of a compound of formula (IIIb) in the presence of an amine of the formula $R^{10}R^{11}NH$:

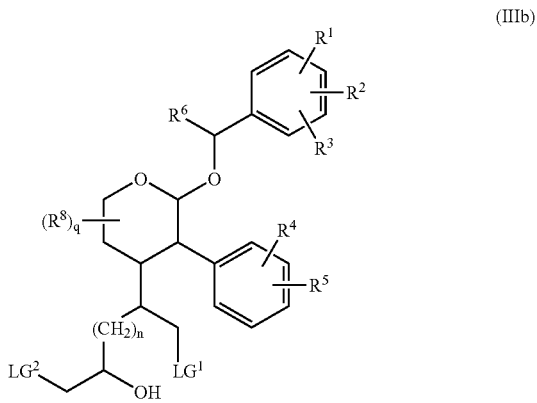

wherein $LG^1$ and $LG^2$ are as previously defined.

The reaction is effected at an elevated temperature, for example, between 120° and 160° C., preferably at about 140° C., in a suitable solvent, such as an alcohol, for instance, methanol.

According to another general process (Cb), compounds of formula (Ib) in which m is 2 and n is 2 may be prepared by the cyclization of a compound of formula (IVb) in the presence of an amine of the formula $R^{10}R^{11}NH$:

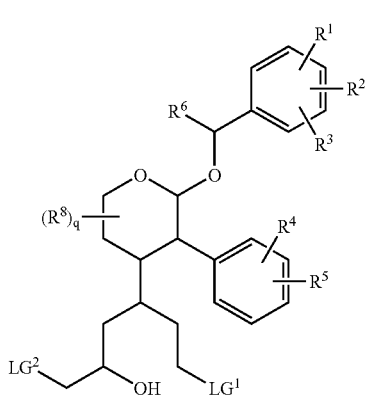

(IVb)

wherein $LG^1$ and $LG^2$ are as previously defined.

The reaction is effected at an elevated temperature, for example, between 120° and 160° C., preferably at about 140° C., in a suitable solvent, such as an alcohol, for instance, methanol.

Further details of suitable procedures will be found in the accompanying Examples.

Compounds of formula (IIb) may be prepared from a compound of formula (Vb)

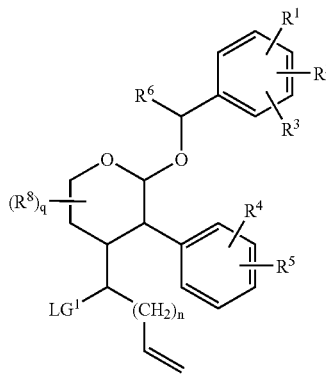

(Vb)

by reaction with a dihydroxylating agent such as AD-mix-α or AD-mix-β (see *Aldrichimica Acta* 1994, 27, 70), followed by conversion of the primary alcohol to the $LG^2$ group.

The dihydroxylation reaction is conveniently effected at room temperature in a solvent such as an alcohol, for instance, tert-butanol, or water, or more preferably a mixture thereof.

The conversion of the primary alcohol to the $LG^2$ group is effected in a conventional manner, for instance by reaction with the appropriate sulfonyl chloride in the presence of a base, such as triethylamine. The reaction is conveniently effected in a solvent such as a halogenated hydrocarbon, for example, dichloromethane, at a reduced temperature, such as below −20° C., and then at room temperature. Addition of dibutyltin oxide to the reaction conveniently promotes formation of the leaving group on the primary alcohol group.

Similarly, compounds of formula (IIIb) may be prepared from a compound of formula (VIb)

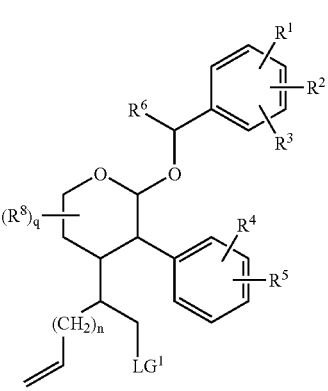

(VIb)

Likewise, compounds of formula (IVb) may be prepared from a compound of formula (VIIb)

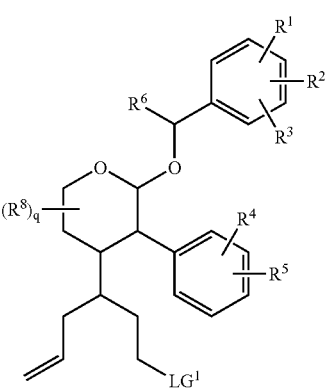

(VIIb)

Compounds of formula (Vb) may be prepared by reaction of an aldehyde of formula (VIIIb)

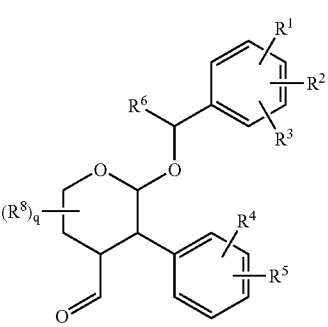

(VIIIb)

with a suitable Grignard reagent, such as $CH_2$=$CH(CH_2)_nCH_2MgBr$ or $CH_2$=$CH(CH_2)_nCH_2MgCl$, followed by conversion of the secondary alcohol to the $LG^1$ group.

The Grignard reaction is effected in the presence of a suitable solvent such as an ether, for instance, tetrahydrofuran, at a reduced temperature, for example, below −40° C., and preferably at about −78° C.

The conversion of the secondary alcohol to the $LG^1$ group is effected in a conventional manner, for instance by reaction with the appropriate sulfonyl chloride in the presence of a base, such as triethylamine. The reaction is conveniently effected in a solvent such as a halogenated hydrocarbon, for example, dichloromethane, at a reduced temperature, such as below −20° C., and then at room temperature.

Compounds of formula (VIIIb) may be prepared by conventional methods such as those described in International (PCT) Patent Publication No. WO 00/56727, for instance, by the oxidation of a corresponding vinyl compound using oxygen and ozone. The reaction is conveniently effected at a reduced temperature, such as at about −78° C., in the presence of an organic solvent such as an alcohol, for example, methanol, or a halogenated hydrocarbon, for example, dichloromethane, or a mixture thereof. Treatment with dimethylsulfide liberates the desired aldehyde.

Compounds of formula (VIb) may be prepared from a compound of formula (IXb)

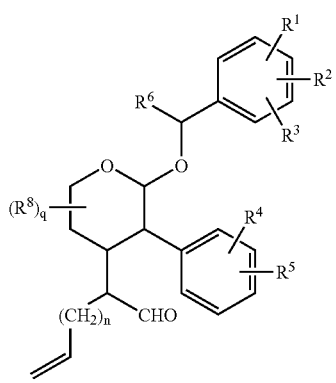

(IXb)

by reaction with a reducing agent such as a borohydride, for example, sodium borohydride, followed by conversion of the alcohol thus formed into the $LG^1$ group as previously described. The reduction is effected in a suitable solvent such as an alcohol, for example, ethanol, at a reduced temperature such as between −10° C. and +5° C., preferably at about 0° C.

Similarly, compounds of formula (VIIb) may be prepared from a compound of formula (Xb)

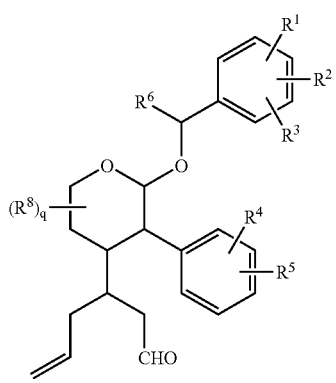

(Xb)

Compounds of formula (IXb) may be prepared from a compound of formula (XIb)

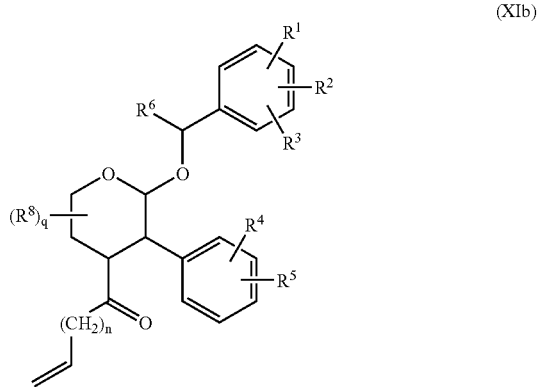

(XIb)

by reaction with, for example, an ylide such as that prepared from $Ph_3P^+CH_2OMeCl^-$ in the presence of a strong base such as lithium diisopropylamide and a suitable solvent such as an ether, for example, tetrahydrofuran, followed by treatment with an acid such as a mineral acid, for example, aqueous hydrochloric acid.

Compounds of formula (XIb) may be prepared from a compound of formula (XIIb)

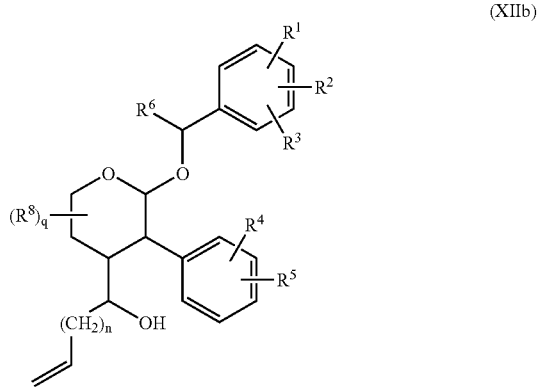

(XIIb)

by a suitable oxidation reaction, such as a Swern oxidation using dimethylsulfoxide and oxalyl chloride, and a base such as triethylamine. The reaction is conveniently effected in a solvent such as a halogenated hydrocarbon, for example, dichloromethane, at a reduced temperature, for example at about −78° C., and then warming to room temperature.

Compounds of formula (XIIb) may be prepared from a compound of formula (VIIIb) by reaction with a suitable Grignard reagent as previously described.

Compounds of formula (Xb) may be prepared from a compound of formula (IXb) under the conditions described above for the preparation of a compound of formula (IXb).

According to a general process (Ac), compounds of formula (Ic) in which A is $NR^{12}$ and B is $S(O)_q$ (where q is zero) may be prepared by the reaction of a compound of formula (IIc) in the presence of an amine of the formula $R^{12}NH_2$:

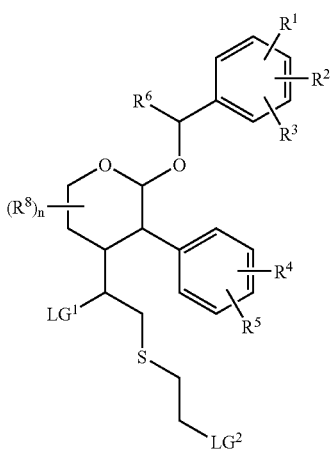

wherein LG$^1$ and LG$^2$ are independently leaving groups, such as mesylate, tosylate, brosylate, nosylate or triflate. Conveniently, LG$^1$ and LG$^2$ may be the same or different, for instance LG$^1$ is may be mesylate whilst LG$^2$ may be tosylate.

The reaction is effected at an elevated temperature, for example, between 120° and 160° C., preferably at about 140° C., in a suitable solvent, such as an alcohol, for instance, methanol.

According to another general process (Bc), compounds of formula (Ic) in which A is S(O)$_q$ (where q is zero) and B is NR$^{12}$ may be prepared from a compound of formula (IIIc)

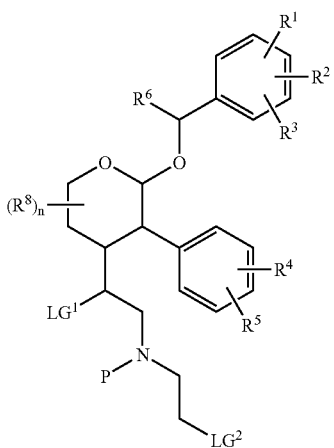

wherein LG$^1$ and LG$^2$ are as previously defined, and P is an amine protecting group, by reaction with sodium sulfide, followed, if desired, by deprotection of the amine and subsequent alkylation of the amine to vary the group R$^{12}$.

The cyclization reaction is effected in a suitable solvent such as acetone at an elevated temperature, for example, at the reflux temperature of the solvent.

A particularly suitable amine protecting group is an alkoxycarbonyl group such as tert-butoxycarbonyl, which is conveniently removed by treatment with trifluoroacetic acid in a solvent such as a halogenated hydrocarbon, for example, dichloromethane, at a reduced temperature, such as between −10° C. and +5° C., for example, at about 0° C.

Further details of suitable procedures will be found in the accompanying Examples.

Compounds of formula (IIc) may be prepared from a corresponding diol of formula (IVc)

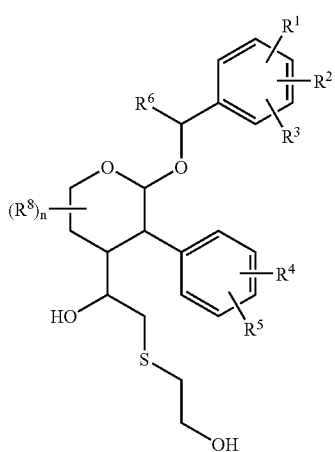

The conversion of the alcohols to the LG$^1$ and LG$^2$ groups is effected in a conventional manner, for instance by reaction with the appropriate sulfonyl chloride in the presence of a base, such as triethylamine. The reaction is conveniently effected in a solvent such as a halogenated hydrocarbon, for example, dichloromethane, at a reduced temperature, such as below −20° C., and then at room temperature.

Similarly, compounds of formula (IIIc) may be prepared from a corresponding diol of formula (Vc)

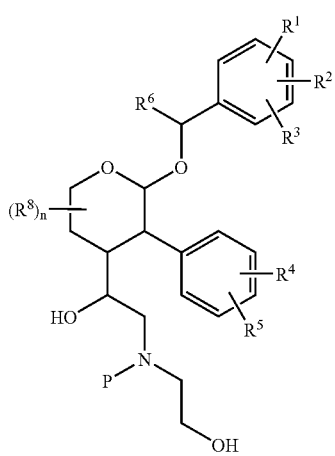

Compounds of formula (IVc) may be prepared from an epoxide of formula (VIc)

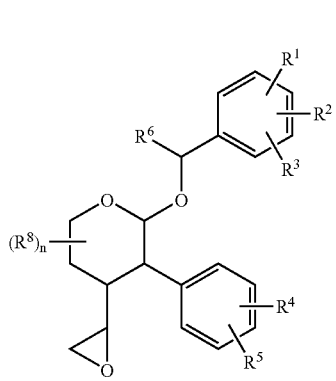

(VIc)

by reaction with $HOCH_2CH_2SH$ in the presence of a base such as a hydroxide, for instance, potassium hydroxide. The reaction is conveniently effected in a solvent such as an alcohol, for example isopropanol, at an elevated temperature, for example at the reflux temperature of the solvent.

Compounds of formula (Vc) may be prepared from an epoxide of formula (VIc) by reaction with $HOCH_2CH_2NH_2$ in a solvent such as an alcohol, for example methanol, at an elevated temperature, for example at the reflux temperature of the solvent, followed by protection of the secondary amine, for example with di-tert-butyl dicarbonate. This reaction is conveniently effected in a solvent such as a halogenated hydrocarbon, for example, dichloromethane, at room temperature.

Compounds of formula (VIc) may be prepared from a compound of formula (VIIc)

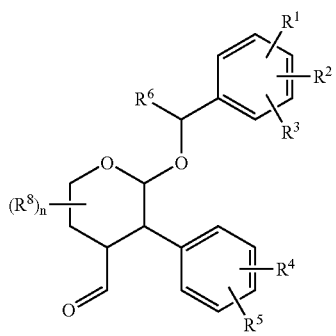

(VIIc)

by reaction with trimethylsulfonium iodide in the presence of a base such as sodium hydride. The reaction is conveniently effected in a suitable solvent such as dimethylsulfoxide or an ether, such as tetrahydrofuran, or a mixture thereof, at a reduced temperature between −10° C. and +5° C., for example, at about 0° C.

Compounds of formula (VIIc) may be prepared by conventional methods such as those described in International (PCT) Patent Publication No. WO 00/56727, for instance, by the oxidation of a corresponding vinyl compound of formula (VIIIc)

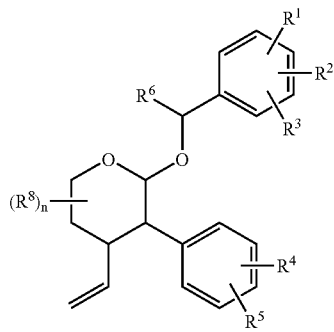

(VIIIc)

using oxygen and ozone. The reaction is conveniently effected at a reduced temperature, such as at about −78° C., in the presence of an organic solvent such as an alcohol, for example, methanol, or a halogenated hydrocarbon, for example, dichloromethane, or a mixture thereof. Treatment with dimethylsulfide liberates the desired aldehyde.

In an alternative method, compounds of formula (VIc) may be prepared directly from a compound of formula (VIIIc) by an epoxidization reaction using a peracid, for example, m-chloroperbenzoic acid. The reaction is effected in a solvent such as a halogenated hydrocarbon, for example, dichloromethane, conveniently at room temperature.

Compounds of formula (VIIIc) are known compounds or may be prepared by conventional methods such as those described in International (PCT) Patent Publication Nos. WO 00/56727 and WO 02/16344.

According to a general process (Ad), compounds of formula (Id) in which m is zero and n is 1 may be prepared by the cyclization of a compound of formula (IId) in the presence of an amine of the formula $R^{11}NH_2$:

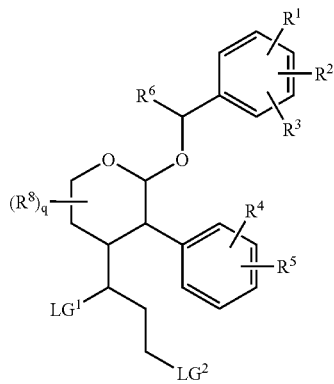

(IId)

wherein $LG^1$ and $LG^2$ are independently leaving groups, such as mesylate, tosylate, brosylate, nosylate or triflate. Conveniently, $LG^1$ and $LG^2$ may be the same or different, for instance $LG^1$ and $LG^2$ may both be mesylate.

The reaction is effected at an elevated temperature, for example, between 120° and 160° C., preferably at about 140° C., in a suitable solvent, such as an alcohol, for instance, methanol.

According to another general process (Bd), compounds of formula (Id) in which m is 1 or 2 and n is zero may be prepared by the cyclization of a compound of formula (IIId) in the presence of an amine of the formula $R^{11}NH_2$:

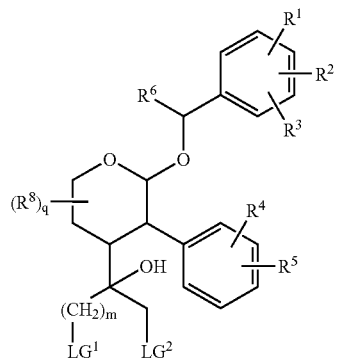
(IIId)

wherein $LG^1$ and $LG^2$ are as previously defined.

The reaction is effected at an elevated temperature, for example, between 120° and 160° C., preferably at about 140° C., in a suitable solvent, such as an alcohol, for instance, methanol.

According to another general process (Cd), compounds of formula (Id) in which m is 2 and n is 1 may be prepared by the cyclization of a compound of formula (IVd) in the presence of an amine of the formula $R^{11}NH_2$:

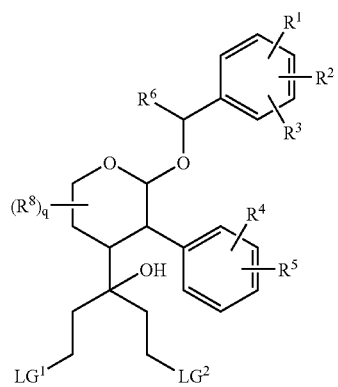
(IVd)

wherein $LG^1$ and $LG^2$ are as previously defined.

The reaction is effected at an elevated temperature, for example, between 120° and 160° C., preferably at about 130° C., in a suitable solvent, such as an alcohol, for instance, methanol.

With regard to general processes (Bd) and (Cd), it will be appreciated by one of ordinary skill in the art that the geminal hydroxyl group can be removed using conventional methodology.

Further details of suitable procedures will be found in the accompanying Examples.

Compounds of formula (IId) may be prepared from a compound of formula (Vd)

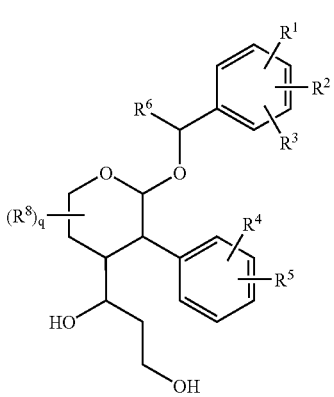
(Vd)

The conversion of the primary and secondary alcohols to the $LG^1$ and $LG^2$ groups is effected in a conventional manner, for instance by reaction with the appropriate sulfonyl chloride (e.g. methanesulfonyl chloride) in the presence of a base, such as triethylamine. The reaction is conveniently effected in a solvent such as a halogenated hydrocarbon, for example, dichloromethane, at a reduced temperature, such as below −20° C., and then at room temperature.

Similarly, compounds of formula (IIId) may be prepared from a compound of formula (VId)

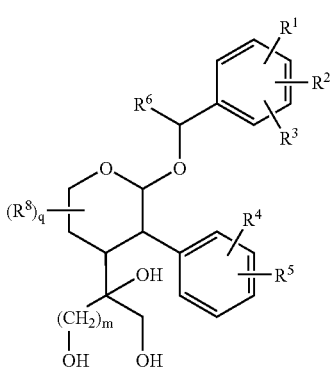
(VId)

Likewise, compounds of formula (IVd) may be prepared from a compound of formula (VIId)

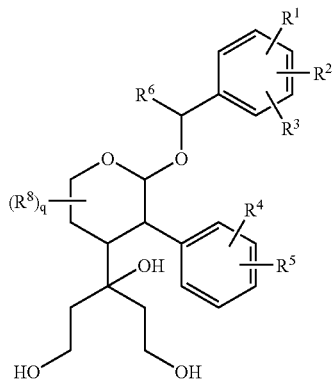
(VIId)

Compounds of formula (Vd) may be prepared from a compound of formula (VIIId)

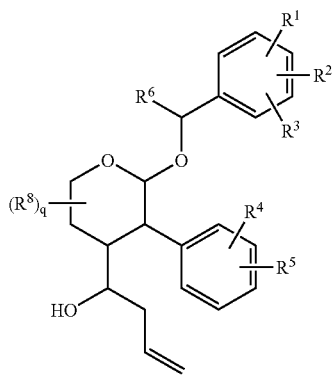
(VIIId)

by reaction with ozone, followed by treatment with sodium borohydride.

The ozonolysis reaction is effected at a reduced temperature, for example, below −40° C., and preferably at about −78° C., in a suitable solvent such as a halogenated hydrocarbon, for example, dichloromethane, or an alcohol, for example, methanol, or a mixture thereof.

Similarly, compounds of formula (VId) may be prepared from a compound of formula (IXd)

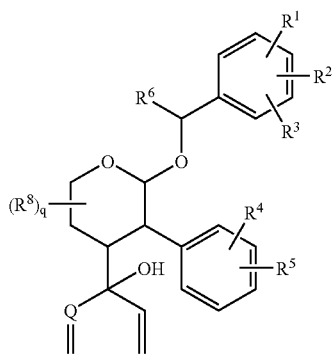
(IXd)

where Q is —CH= (for compounds where m is 1) or —CH$_2$CH= (for compounds where m is 2).

Likewise, compounds of formula (VIId) may be prepared from a compound of formula (Xd)

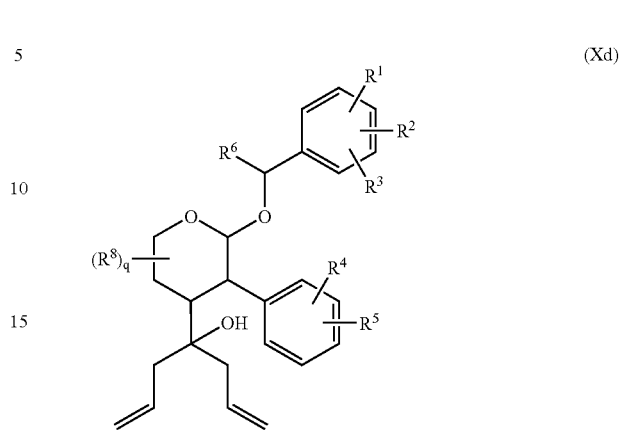
(Xd)

Compounds of formula (VIIId) may be prepared by reaction of a compound of formula (XId)

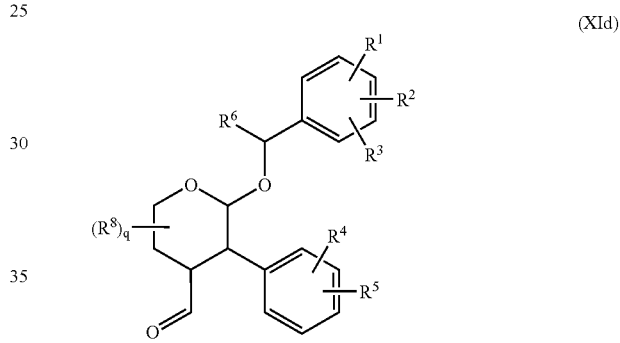
(XId)

with a suitable Grignard reagent, such as CH$_2$=CHCH$_2$MgBr or CH$_2$=CHCH$_2$MgCl. The reaction is effected in the presence of a suitable solvent such as an ether, for instance, diethyl ether or tetrahydrofuran, at a reduced temperature, for example, below −40° C., and preferably at about −78° C.

The stereochemistry of the intermediate of formula (VIIId) may be directed by the inclusion in the Grignard reaction of chlorobis[(1S,2R,3S,5S)-2,6,6-trimethylbicyclo[3.1.1]hept-3-yl]borane ((+)-DIP-Cl) or chlorobis[(1R,2S,3R,5R)-2,6,6-trimethylbicyclo[3.1.1]hept-3-yl]borane ((−)-DIP-Cl) which is conveniently pre-mixed with the allyl Grignard reagent at a reduced temperature, for instance, at about −40° C., and warmed to about room temperature, before cooling and addition to the aldehyde of formula (XId).

Compounds of formula (XId) may be prepared by conventional methods such as those described in International (PCT) Patent Publication No. WO 00/56727, for instance, by the oxidation of a corresponding vinyl compound using oxygen and ozone. The reaction is conveniently effected at a reduced temperature, such as at about −78° C., in the presence of an organic solvent such as an alcohol, for example, methanol, or a halogenated hydrocarbon, for example, dichloromethane, or a mixture thereof. Treatment with dimethylsulfide liberates the desired aldehyde.

Compounds of formulae (IXd) where Q is —CH= and (Xd) may be prepared from a compound of formula (XIId)

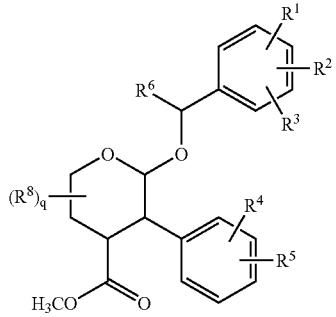
(XIId)

by reaction with a suitable Grignard reagent, for instance, of the formula CH$_2$=CHMgBr (for formula (IXd) where Q is —CH=) or CH$_2$=CHCH$_2$MgBr (for formula (Xd)). The reaction is effected in the presence of a suitable solvent such as an ether, for instance, diethyl ether or tetrahydrofuran, at a reduced temperature, for example, below −40° C., and preferably at about −78° C. Cerium(III) chloride may be added to avoid reduction and enolization side reactions.

Compounds of formula (XIId) may be prepared from the corresponding carboxylic acid by conventional procedures, for instance, by reaction of the carboxylic acid with (trimethylsilyl)diazomethane and methanol in a suitable solvent such as toluene, conveniently at room temperature.

Compounds of formula (IXd) where Q is —CH$_2$CH= may be prepared from a compound of formula (XIIId)

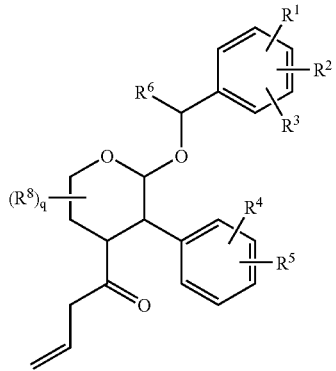
(XIIId)

by reaction with a suitable Grignard reagent, such as CH$_2$=CHMgBr or CH$_2$=CHMgCl, as previously described.

Compounds of formula (XIIId) may be prepared from a compound of formula (XIVd)

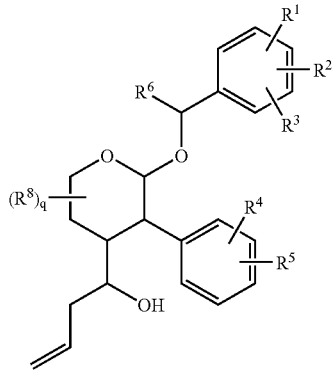
(XIVd)

by a suitable oxidation reaction, such as a Swern oxidation using dimethylsulfoxide and oxalyl chloride, and a base such as triethylamine. The reaction is conveniently effected in a solvent such as a halogenated hydrocarbon, for example, dichloromethane, at a reduced temperature, for example at about −78° C., and then warming to room temperature.

Compounds of formula (XIVd) may be prepared from a compound of formula (XId) by reaction with a suitable Grignard reagent, such as CH$_2$=CHCH$_2$MgBr or CH$_2$=CHCH$_2$MgCl, as previously described.

According to a general process (Ae), compounds of formula (Ie) may be prepared by the reaction of a compound of formula (IIe)

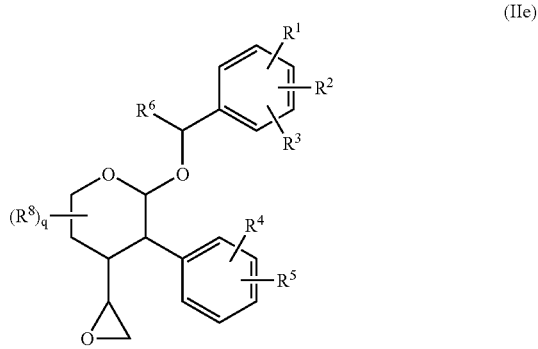
(IIe)

with an amine of the formula R$^{13}$R$^{14}$NH,

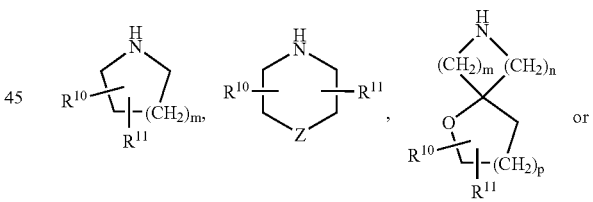

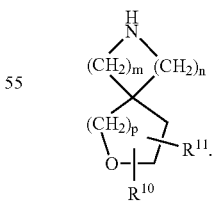.

The reaction is effected at an elevated temperature, for example, between 110° and 150° C., preferably at about 130° C., in a suitable solvent, such as an alcohol, for instance, methanol.

Further details of suitable procedures will be found in the accompanying Examples.

Compounds of formula (IIe) may be prepared from a compound of formula (IIIe)

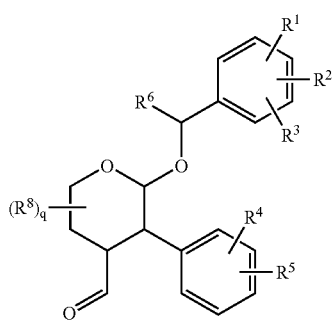
(IIIe)

by reaction with trimethylsulfonium iodide in the presence of a base such as sodium hydride. The reaction is conveniently effected in a suitable solvent such as dimethylsulfoxide or an ether, such as tetrahydrofuran, or a mixture thereof, at a reduced temperature between −10° C. and +5° C., for example, at about 0° C.

Compounds of formula (IIIe) may be prepared by conventional methods such as those described in International (PCT) Patent Publication No. WO 00/56727, for instance, by the oxidation of a corresponding vinyl compound using oxygen and ozone. The reaction is conveniently effected at a reduced temperature, such as at about −78° C., in the presence of an organic solvent such as an alcohol, for example, methanol, or a halogenated hydrocarbon, for example, dichloromethane, or a mixture thereof. Treatment with dimethylsulfide liberates the desired aldehyde.

Amines of use in the general process (Ae) are either known compounds, or may be prepared by methods well known to one of ordinary skill in the art. For example, methods for the preparation of the spirocyclic amines are provided in the literature—see for instance, *Bioorg. Med. Chem. Lett.*, 12 (2002) 1759-62 and International (PCT) Patent Publication No. WO 01/87838.

According to a general process (Af), compounds of formula (If) wherein $R^{11}$ represents $CO_2C_{1-6}$-alkyl and $R^{12}$ represents OH, may be prepared by the treatment of a compound of the formula (IIf)

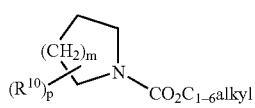
(IIf)

with a lithiating agent such as an alkyl lithium compound, for example, sec-butyllithium in the presence of an organic base such as N,N,N',N'-tetramethyl-1,2-ethanediamine, in a suitable solvent, such as an ether, for example, diethyl ether, at a reduced temperature, such as below −40°, and preferably at about −78° C.; which treatment is followed by reaction with a compound of formula (IIIf)

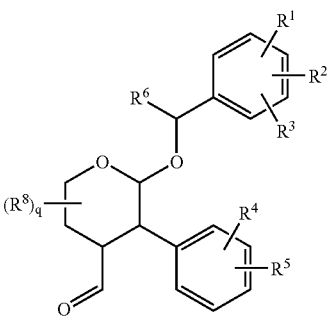
(IIIf)

The reaction is conveniently effected in a suitable solvent, such as an ether, for example, diethyl ether, at a reduced temperature, such as below −40°, and preferably at about −78° C.

According to another general process (Bf), compounds of formula (If) wherein $R^{12}$ is linked to $R^{11}$ such that there is formed a ring, the linkage —$R^{12}$—$R^{11}$— being —OC(O)—, may be prepared by the interconversion of a compound of formula (If) wherein $R^{11}$ represents $CO_2C_{1-6}$alkyl and $R^{12}$ represents OH by treatment with a reducing agent such as a hydride, for instance sodium hydride, the reaction being effected in a suitable solvent such as an ether, for example, tetrahydrofuran, conveniently at about room temperature.

According to another general process (Cf), compounds of formula (If) wherein $R^{11}$ represents hydrogen and $R^{12}$ represents OH (which compounds may themselves serve as precursors for further derivatization of the amino moiety, may be prepared by the interconversion of a compound of formula (If) wherein $R^{12}$ is linked to $R^{11}$ such that there is formed a ring, the linkage —$R^{12}$—$R^{11}$— being —OC(O)—, by treatment with lithium hydroxide, the reaction being effected in a suitable solvent such as an ether, for example, tetrahydrofuran, and alcohol, for example, methanol, or water, or a mixture thereof, at an elevated temperature, such as between 40° C. and 60° C., preferably at about 50° C.

Further details of suitable procedures will be found in the accompanying Examples.

Compounds of formula (IIf) are either known compounds or they may be prepared by methods readily apparent to one of ordinary skill in the art.

Compounds of formula (IIIf) may be prepared by conventional methods such as those described in International (PCT) Patent Publication No. WO 00/56727, for instance, by the oxidation of a corresponding vinyl compound using oxygen and ozone. The reaction is conveniently effected at a reduced temperature, such as at about −78° C., in the presence of an organic solvent such as an alcohol, for example, methanol, or a halogenated hydrocarbon, for example, dichloromethane, or a mixture thereof. Treatment with dimethylsulfide liberates the desired aldehyde.

It will be appreciated that the general methodology described above may be adapted, using methods that are readily apparent to one of ordinary skill in the art, in order to prepare further compounds of the present invention. In particular, compounds of formula (I) may be interconverted into further compounds of formula (I) using conventional synthetic techniques such as N-alkylation or O-alkylation, oxidation or reduction.

Thus, for instance, a compound of formula (Ia), (Iab) or (Ib) wherein X is CHOH may be converted into a corresponding compound of formula (Ia), (Iab) or (Ib) respectively wherein X is C=O by reaction with a strong oxidizing agent, such as Dess-Martin periodinane, to afford the desired ketone.

Also, for instance, for the compounds of formula (Ic), the $NR^{12}$ moiety where $R^{12}$ is hydrogen may be alkylated by reaction with a suitable alkyl halide, such as methyl iodide or ethyl iodide, conveniently at about room temperature, in the presence of an acid acceptor such as potassium carbonate or N,N-diisopropylethylamine.

In another example of such interconversion reactions, the sulfur atom of the thiomorpholine ring of the compounds of formula (Ic) may be oxidized using, for instance, sodium metaperiodate in acetic acid to afford the corresponding sulfoxide or sulfone.

Also, for instance, the compounds of formula (Id) having the $NR^{11}$ moiety where $R^{11}$ is hydrogen and NH moieties in the compounds of formulae (Ie) and (If) may be alkylated by reaction with a suitable alkyl halide, such as methyl iodide or ethyl iodide, conveniently at about room temperature, in the presence of an acid acceptor such as potassium carbonate or N,N-diisopropylethylamine.

In another example of such interconversion reactions, a compound of formula (Ie) or (If) wherein Z is S may be converted into a corresponding compound of formula (Ie) or (If) respectively wherein Z is SO or $S(O)_2$ by an oxidation reaction using, for instance, sodium metaperiodate in acetic acid to afford the desired sulfoxide or sulfone.

Other general methods that may be adapted to the synthesis of the pyran acetal derivatives of the present invention are described in International (PCI) Patent Publication Nos. WO 00/56727 and WO 02/16344.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 100 nM on said test method.

The following non-limiting Examples serve to illustrate the preparation of compounds of the present invention:

DESCRIPTION 1

Piperidine-1,4-dicarboxylic acid 1-benzyl ester 4-ethyl ester

A solution of benzyl chloroformate (95 g, 0.56 mol) in dichloromethane (200 ml) was added dropwise to an ice-bath-cooled, stirred mixture of ethyl isonipecotate (87 g, 0.55 mol), sodium carbonate (60 g, 0.57 mol) and dichloromethane (200 ml) over 70 minutes. The mixture was stirred at ambient temperature for 2.5 days and filtered though a pad of Celite™. The filtrate was concentrated in vacuo. The residue was partitioned between 2M aqueous hydrochloric acid and diethyl ether. Organic layer was separated, dried ($MgSO_4$), filtered and concentrated. The residue was chromatographed on silica gel (ethyl acetate/iso-hexane) to give the title product (152 g, 94%).

$^1$H NMR (360 MHz, $CDCl_3$): δ 7.41-7.27 (5H, m), 5.12 (2H, s), 4.22-3.99 (2H, m), 4.14 (2H, q, J 7.4 Hz), 2.93 (2H, br t, J 11.6 Hz), 2.45 (2H, m), 1.97-1.81 (2H, m), 1.74-1.56 (2H, m), 1.25 (3H, t, J 7.4 Hz).

DESCRIPTION 2

4-[2-(tert-Butyldimethylsilyloxy)-1-hydroxyethyl]-piperidine-1,4-dicarboxylic acid 1-benzyl ester 4-ethyl ester A solution of piperidine-1,4-dicarboxylic acid 1-benzyl ester 4-ethyl ester (Description 1; 10 g, 34.4 mmol) in tetrahydrofuran (100 ml) was cooled to −78° C. Lithium bis(trimethylsilyl)amide (1.0M in tetrahydrofuran, 50 ml, 50 mmol) was added dropwise and the mixture stirred, allowing to warm to room temperature over 1.5 hours. The orange solution was re-cooled to −78° C. and (tert-butyldimethylsilyloxy)acetaldehyde (10 g, 57.3 mmol) added. The mixture was allowed to warm to room temperature over 2.5 hours, then quenched with saturated aqueous ammonium chloride solution. The reaction mixture was partitioned between diethyl ether and water. The organic layer was dried ($MgSO_4$) and concentrated in vacuo. The residue was purified by flash column chromatography on silica, eluting with 5-15% diethyl ether/dichloromethane, to give the title compound (12.4 g, 78%).

$^1$H NMR (400 MHz, $CDCl_3$): δ 7.36-7.35 (5H, m), 5.30 (2H, s), 4.21 (2H, q, J 7.1 Hz), 4.15-4.04 (2H, m), 3.66-3.57 (3H, m), 2.83 (2H, d, J 4.3 Hz), 2.23-2.05 (2H, m), 1.63-1.56 (2H, m), 1.29 (3H, t, J 7.1 Hz), 0.88 (9H, s), 0.06 (6H, s).

DESCRIPTION 3

4-(1,2-Dihydroxyethyl)-4-hydroxymethyl-piperidine-1-carboxylic acid benzyl ester Lithium borohydride (1 g, 45 mmol) was added portionwise to a solution of 4-[2-(tert-butyldimethylsilyloxy)-1-hydroxyethyl]-piperidine-1,4-dicarboxylic acid 1-benzyl ester 4-ethyl ester (Description 2; 11.2 g, 24.1 mmol) in tetrahydrofuran (75 ml). The mixture was stirred at room temperature for 2 hours. The reaction was quenched by addition of saturated aqueous sodium hydrogencarbonate solution, then partitioned between ethyl acetate and water. The organic layer was dried ($MgSO_4$) and concentrated in vacuo to give the diol. This was dissolved in tetrahydrofuran (50 ml). Tetrabutylammonium fluoride (1.0M in tetrahydrofuran, 32 ml, 32 mmol) was added and the reaction stirred at room temperature for 1 hour. The mixture was partitioned between water and ethyl acetate. The organic layer was dried ($MgSO_4$) and concentrated in vacuo. The residue was purified by flash column chromatography on silica, eluting with 1, 2, 5 and 10% methanol/ethyl acetate, to give the title compound (5.4 g, 73%).

$^1$H NMR (360 MHz, $CDCl_3$): δ 7.39-7.29 (5H, m), 5.13 (2H, s), 3.82-3.70 (6H, m), 3.54 (1H, t, J 4.7 Hz), 3.26-2.74 (5H, m), 1.73-1.54 (3H, m), 1.39-1.31 (1H, m).

DESCRIPTION 4

4-Hydroxy-2-oxa-8-aza-spiro[4.5]decane-8-carboxylic acid benzyl ester

Diethyl azodicarboxylate (1.4 g, 8.1 mmol) was added to a solution of 4-(1,2-dihydroxyethyl)-4-hydroxymethyl-piperidine-1-carboxylic acid benzyl ester (Description 3; 2 g, 6.5 mmol) and triphenylphosphine (2.4 g, 9.1 mmol) in tetrahydrofuran (40 ml). The reaction was stirred at room temperature for 2 hours then the solvent was removed in vacuo. The residue was purified by flash column chromatography on silica, eluting with 1, 2 and 4% methanol/dichloromethane, to give the title compound (1.43 g, 76%).

$^1$H NMR (400 MHz, CDCl$_3$): δ 7.38-7.30 (5H, m), 5.13 (2H, s), 4.12-4.08 (1H, m), 4.02-3.99 (1H, m), 3.74-3.65 (5H, m), 3.39-3.33 (1H, m), 3.27-3.20 (1H, m), 1.89-1.87 (1H, m), 1.82-1.76 (1H, m), 1.59-1.54 (1H, m), 1.51-1.48 (2H, m).

DESCRIPTION 5

4-[2-(tert-Butyldimethylsilyloxy)-1-hydroxyethyl]-piperidine-4-dicarboxylic acid 1-(1,1-dimethylethyl) ester 4-ethyl ester The title compound was prepared as described in Description 2 from piperidine-1,4-dicarboxylic acid 1-tert-butyl ester 4-ethyl ester.

$^1$H NMR (360 MHz, CDCl$_3$): δ 4.21 (2H, q, J 7.0 Hz), 4.08-3.90 (2H, m), 3.75-3.50 (3H, m), 2.89-2.69 (2H, m), 2.19 (1H, m), 2.03 (1H, m), 1.57 (2H, dt, J 4.6, 13.0 Hz), 1.45 (9H, s), 1.29 (3H, t, J 7.4 Hz), 0.89 (9H, s), 0.06 (6H, s).

DESCRIPTION 6

4-(1,2-Dihydroxyethyl)-4-hydroxymethyl-piperidine-1-carboxylic acid 1,1-dimethylethyl ester The title compound was prepared as described in Description 3 from the product of Description 5.

$^1$H NMR (400 MHz, CDCl$_3$): δ 3.80-3.60 (6H, m), 3.55 (1H, m), 3.24-3.02 (3H, m), 1.73-1.48 (4H, m), 1.45 (9H, s), 1.33 (1H, m).

DESCRIPTION 7

4-Hydroxy-2-oxa-8-aza-spiro[4.5]decane-8-carboxylic acid 1,1-dimethylethyl ester The title compound was prepared as described in Description 4 from the product of Description 6.

$^1$H NMR (400 MHz, CDCl$_3$): δ 4.11 (1H, dd, J 4.7, 10.2 Hz), 4.01 (1H, dt, J 1.6, 4.7 Hz), 3.74 (1H, d, J 8.6 Hz), 3.73 (1H, dd, J 2.0, 10.7 Hz), 3.67 (1H, d, J 8.6 Hz), 3.63 (2H, m), 3.27 (1H, dt, J 6.3, 13.7 Hz), 3.14 (1H, ddd, J 3.5, 9.0, 12.9 Hz), 1.82 (1H, d, J 5.5 Hz), 1.77 (1H, ddd, J 3.9, 9.0, 13.3 Hz), 1.56 (1H, ddd, J 3.5, 6.3, 13.3 Hz), 1.50-1.45 (2H, m), 1.46 (9H, s).

DESCRIPTION 8

(RS)-2-Oxa-8-aza-spiro[4.5]decan-4-ol hydrochloride

4-Hydroxy-2-oxa-8-aza-spiro[4.5]decane-8-carboxylic acid 1,1-dimethylethyl ester (Description 7; 0.86 g, 3.3 mmol) was stirred overnight in 2M ethereal hydrogen chloride. The mixture was filtered and the solid dried to give the title compound (0.5 g, 77%).

$^1$H NMR (360 MHz, MeOH-d$_4$): δ 4.15-4.06 (2H, m), 3.71-3.61 (3H, m), 3.69-3.13 (4H, m), 2.08-2.03 (1H, m), 1.80-1.74 (3H, m).

DESCRIPTION 9

(4R)-4-[(1S,4R)-4,7,7-Trimethyl-3-oxo-2-oxa-bicyclo[2.2.1]heptane-1-carbonyloxy]-2-oxa-8-aza-spiro[4.5]decane-8-carboxylic acid benzyl ester and (4S)-4-[(1S,4R)-4,7,7-Trimethyl-3-oxo-2-oxa-bicyclo[2.2.1]heptane-1-carbonyloxy]-2-oxa-8-aza-spiro[4.5]decane-8-carboxylic acid benzyl ester (1S)-(−)-Camphanic chloride (335 mg, 1.54 mmol) was added to a stirred solution of 4-hydroxy-2-oxa-8-aza-spiro[4.5]decane-8-carboxylic acid benzyl ester (Description 4; 300 mg, 1.03 mmol), triethylamine (0.4 ml, 2.9 mmol) and 4-N,N-dimethylaminopyridine (15 mg, 0.12 mmol) in dichloromethane (5 ml). The mixture was stirred overnight and diluted with ethyl acetate and washed with saturated aqueous NaHCO$_3$, 2M HCl and water. The organic phase was dried (Na$_2$SO$_4$) and concentrated. The residue was purified on silica (i-hexane:ethyl acetate) to give the title ester as a mixture of diastereoisomers (460 mg). Diastereoisomers were separated on prep. HPLC (HIRPB, acetonitrile: 0.1% aq. trifluoroacetic acid) to give isomer A (190 mg) and isomer B (195 mg).

Isomer A: (4S)-Isomer of the Title Compound $^1$H NMR (400 MHz, CDCl$_3$): δ 7.41 (5H, m), 5.13 (2H, s), 5.11 (1H, dd, J 1.6, 4.7 Hz), 4.27 (1H, dd, J 4.7, 11.3 Hz), 3.87 (1H, d, J 8.6 Hz), 3.77 (1H, dd, J 2.0, 11.3 Hz), 3.77-3.67 (2H, m), 3.67-3.58 (1H, m), 3.40 (1H, dt, J 6.3, 14.1 Hz), 3.21 (1H, m), 2.38 (1H, ddd, J 4.3, 11.0, 13.7 Hz), 2.05 (1H, dt, J 4.7, 9.4, 13.7 Hz), 1.94 (1H, ddd, J 4.3, 10.6, 12.9 Hz), 1.77-1.67 (2H, m), 1.66-1.56 (3H, m), 1.12 (3H, s), 1.07 (3H, s), 0.96 (3H, s).

Isomer B: (4R)-Isomer of the Title Compound $^1$H NMR (400 MHz, CDCl$_3$): δ 7.40-7.29 (5H, m), 5.13 (2H, s), 5.11 (1H, dd, J 1.6, 4.7 Hz), 4.27 (1H, dd, J 5.1, 11.3 Hz), 3.87 (1H, d, J 8.6 Hz), 3.77-3.66 (3H, m), 3.40 (1H, dt, J 6.3, 14.4 Hz), 3.21 (1H, m), 2.43 (1H, ddd, J 4.3, 10.6, 13.3 Hz), 2.01 (1H, ddd, J 4.7, 9.0, 13.3 Hz), 1.93 (1H, ddd, J 4.3, 10.6, 12.9 Hz), 1.80-1.65 (3H, m), 1.64-1.56 (3H, m), 1.12 (3H, s), 1.04 (3H, s), 0.97 (3H, s).

DESCRIPTION 10

(1S,4R)-4,7,7-Trimethyl-3-oxo-2-oxa-bicyclo[2.2.1]heptane-1-carboxylic acid (4R)-2-oxa-8-aza-spiro[4.5]dec-4-yl ester trifluoroacetate A mixture of isomer B of the product of Description 9 (130 mg, 0.27 mmol), palladium on carbon (10%, 73 mg), trifluoroacetic acid (0.1 ml) and ethanol (20 ml) was stirred at room temperature under H$_2$ atmosphere (balloon) for 30 minutes, and then filtered through a pad of Celite™ and concentrated to give the title compound (130 mg).

$^1$H NMR (400 MHz, MeOH-d$_4$): δ 5.19 (1H, dd, J 2.0, 4.7 Hz), 4.29 (1H, dd, J 5.0, 10.8 Hz), 3.86 (1H, d, J 8.8 Hz), 3.76 (1H, dd, J 2.0, 11.1 Hz), 3.69 (1H, d, J 8.8 Hz), 3.26-3.11 (3H, m), 3.03 (1H, dd, J 3.5, 8.8, 12.6 Hz), 2.50 (1H, ddd, J 6.1, 12.6, 15.2 Hz), 2.09-1.90 (3H, m), 1.98-1.74 (3H, m), 1.63 (1H, m), 1.64-1.56 (3H, m), 1.10 (3H, s), 1.08 (3H, s), 0.97 (3H, s).

DESCRIPTION 11

2-[1-{(2R,3R,4R)-2-[(1R)-1-(3,5-Bis(trifluoromethyl)phenyl)ethoxy]-3-(4-fluorophenyl)-tetrahydropyran-4-carbaldehyde N-Methylmorpholine N-oxide (1 g, 8.6 mmol) and osmium tetroxide (2 ml, 2.5% solution in tert-butanol) were added to a solution of (2R,3R,4S)-2-[(1R)-1-(3,5-bis(trifluoromethyl)phenyl)ethoxy]-3-(4-fluorophenyl)-4-vinyl-tetrahydropyran (see Example 147 in WO 00/56727; 2 g, 4.3 mmol) in tetrahydrofuran (25 ml) and water (10 ml). The mixture was stirred at room temperature for one hour before sodium periodate (9 g, 43 mmol) was added. This mixture was stirred for 45 minutes and then filtered through Celite™. The filtrate was diluted with ethyl acetate (50 ml) and washed with brine. The organic extracts were dried and concentrated. The residue was chromatographed on silica gel eluting with ethyl acetate/iso-hexanes to give the title compound (1.6 g, 80%).

$^1$H NMR (400 MHz, CDCl$_3$): δ 9.47 (1H, s), 7.70 (1H, s), 7.27 (2H, s), 7.15-7.12 (2H, m), 6.99-6.95 (2H, m), 4.97 (1H, q, J 6.6 Hz), 4.28-4.16 (2H, m), 3.60-3.58 (1H, m), 3.00 (1H, dd, J 7.3, 10.6 Hz), 2.80-2.70 (1H, m), 1.85-1.81 (2H, m), 1.39 (3H, d, J 6.6 Hz).

DESCRIPTION 12

(1S,4R)-4,7,7-Trimethyl-3-oxo-2-oxa-bicyclo[2.2.1] heptane-1-carboxylic acid (4S)-8-{(2R,3R,4R)-2-[(1R)-1-(3,5-bis(trifluoromethyl)phenyl)ethoxy]-3-(4-fluorophenyl)-tetrahydropyran-4-ylmethyl}-2-oxa-8-aza-spiro[4.5]dec-4-yl ester Palladium hydroxide (20% on carbon, 20 mg) was added as a slurry in ethanol to a solution of isomer A of the product of Description 9 (120 mg, 0.25 mmol) in ethanol (5 ml). The mixture was hydrogenated in a Parr apparatus (45 psi) for 30 minutes then filtered through Celite™ and washed with ethanol. The filtrate was concentrated in vacuo. The residue and 2-[1-{(2R,3R,4R)-2-[(1R)-1-(3,5-bis(trifluoromethyl)phenyl)ethoxy]-3-(4-fluorophenyl)-tetrahydropyran-4-carbaldehyde (Description 11; 232 mg, 0.5 mmol) were suspended in 1,2-dichloroethane (10 ml) and stirred at room temperature for 30 minutes. Sodium triacetoxyborohydride (105 mg, 0.5 mmol) was added and the reaction stirred overnight at room temperature. The mixture was partitioned between dichloromethane and brine. The organic layer was dried (MgSO$_4$) and concentrated in vacuo. The residue was purified by preparative thin layer chromatography, eluting with 7.5% methanol/dichloromethane, to give the title compound (138 mg, 70%).

m/z (ES+) 786 (M+H)$^+$.

DESCRIPTION 13

(1S,4R)-4,7,7-Trimethyl-3-oxo-2-oxa-bicyclo[2.2.1] heptane-1-carboxylic acid (4R)-8-{(2R,3R,4R)-2-[(1R)-1-(3,5-bis(trifluoromethyl)phenyl)ethoxy]-3-(4-fluorophenyl)-tetrahydropyran-4-ylmethyl}-2-oxa-8-aza-spiro[4.5]dec-4-yl ester Solid sodium triacetoxyborohydride (107 mg, 0.504 mmol) was added to a stirred mixture of 2-[1-{(2R,3R,4R)-2-[(1R)-1-(3,5-bis(trifluoromethyl)phenyl)ethoxy]-3-(4-fluorophenyl)-tetrahydropyran-4-carbaldehyde (Description 11; 121 mg, 0.36 mmol), (1S,4R)-4,7,7-trimethyl-3-oxo-2-oxa-bicyclo[2.2.1]heptane-1-carboxylic acid (4R)-2-oxa-8-aza-spiro[4.5]dec-4-yl ester trifluoroacetate (Description 10; 130 mg), triethylamine (0.1 ml, 0.72 mmol) and dichloromethane (3 ml) at room temperature. The mixture was stirred for 45 minutes, quenched with saturated aqueous NaHCO$_3$ and extracted into dichloromethane. The organic extract was dried (Na$_2$SO$_4$) and concentrated. The residue was purified by preparative TLC (dichloromethane:methanol) to give the title compound (100 mg). The HCl salt was prepared and recrystallised from ethyl acetate:methanol.

$^1$H NMR (400 MHz, CDCl$_3$): δ 7.67 (1H, s), 7.17 (2H, s), 7.02-6.89 (4H, m), 4.98 (1H, m), 4.95 (1H, q, J 6.3 Hz), 4.23-4.08 (3H, m), 3.68 (1H, d, J 8.6 Hz), 3.66 (1H, dd, J 1.6, 9.4 Hz), 3.58-3.45 (2H, m), 2.50-2.33 (3H, m), 2.25-1.83 (8H, m), 1.81-1.65 (2H, m), 1.57-1.40 (3H, m), 1.36 (3H, d, J 6.6 Hz), 1.11 (3H, s), 1.02 (3H, s), 0.94 (3H, s); m/z (ES+) 786 (M+H)$^+$.

DESCRIPTION 14

(1S,4R)-4,7,7-Trimethyl-3-oxo-2-oxa-bicyclo[2.2.1] heptane-1-carboxylic acid (4R)-8-{(2R,3R,4R)-2-[(1R)-1-(3,5-bis(trifluoromethyl)phenyl)ethoxy]-3-(3-bromo-4-fluorophenyl)-tetrahydropyran-4-ylmethyl}-2-oxa-8-aza-spiro[4.5]dec-4-yl ester (i) (2R,3R,4R)-2-[(1R)-1-(3,5-Bis(trifluoromethyl)phenyl)ethoxy]-3-(3-bromo-4-fluorophenyl)tetrahydropyran-4-carbaldehyde a) (3-Bromo-4-fluorophenyl)acetic acid 3-bromopropyl ester (3-Bromofluorophenyl)acetyl chloride (30.2 g, 0.12 mol) was dissolved in dichloromethane (70 mL) and the solution was cooled to 0° C. 3-Bromopropanol (24.7 g, 0.177 mol) in dichloromethane (30 mL) was added dropwise and the mixture was stirred at room temperature overnight. The mixture was washed with water, brine, dried MgSO$_4$) and the solvent was removed in vacuo. The resulting oil was purified on silica using 5-10% ethyl acetate in hexane to give the product (36 g, 82%).

$^1$H NMR (400 MHz, CDCl$_3$): δ 7.48 (1H, dd, J 2.3, 6.5 Hz), 7.19 (1H, ddd, J 2.3, 4.6, 8.5 Hz), 7.10 (1H, t, J 8.4 Hz), 4.25 (2H, t, J 6.1 Hz), 3.58 (2H, s), 3.41 (2H, t, J 6.6 Hz), 2.17 (2H, quintet, J 6.2 Hz).

b) (3-Bromo-4-fluorophenyl)-3,4,5,6-tetrahydrohydropyran-2-one

Sodium hydride (4.62 g, 0.11 mol) was suspended in dimethylformamide (200 mL) and the suspension was warmed to 60° C. To this was added dropwise (3-bromo-4-fluoro)phenylacetic acid 3-bromopropyl ester (from step a) above; 35.3 g) in dimethylformamide (20 mL) and the mixture was stirred for 30 min until all gas evolution ceased. The mixture was cooled and quenched with water (10 mL) cautiously, and then diluted with water (1500 mL) and extracted with ethyl acetate (3×100 mL). The pooled organic extracts were washed with brine, dried (MgSO$_4$) and evaporated. The crude residue was purified by chromatography on silica using 10-30% ethyl acetate in hexane as eluant to give the lactone (17.1 g, 63%).

$^1$H NMR (400 MHz, CDCl$_3$): δ 7.44 (1H, dd, J 2.3, 6.2 Hz), 7.17 (1H, ddd, J 2.2, 4.6, 8.5 Hz), 7.07 (1H, t, J 8.4 Hz), 4.45 (2H, m), 3.72 (1H, dd, J 6.8, 10.2 Hz), 2.30 (1H, m), 2.03 (3H, m).

c) (±) 3-Bromo-(3-bromo-4-fluorophenyl)-3,4,5,6-tetrahydrohydropyran-2-one (3-Bromo-4-fluorophenyl)-3,4,5,6-tetrahydrohydropyran-2-one (from step b) above; 14.82 g, 0.054 mol) was dissolved in carbon tetrachloride (200 mL) and benzoyl peroxide (100 mg) and N-bromosuccinimide (11.63 g, 0.065 mol) were added. The mixture was heated cautiously to reflux and maintained at reflux for 3 h. The mixture was cooled, filtered and concentrated. The crude residue was purified by chromatography on silica using 10-100% ethyl acetate in hexane as eluant to give the bromide (17.9 g, 95%).

$^1$H NMR (400 MD, CDCl$_3$): δ 7.84 (1H, dd, J 2.6, 6.3 Hz), 7.57 (1H, ddd, J 2.6, 4.4, 8.8 Hz), 7.13 (1H, t, J 8.6 Hz), 4.62 (1H, m), 4.42 (1H, m), 2.80-2.60 (2H, m), 2.38 (1H, m), 2.30 (1H, m), 1.88 (1H, m).

d) 3-(Bromo-4-fluorophenyl)-5,6-dihydropyran-2-one (±) 3-Bromo-(3-bromo-4-fluorophenyl)-3,4,5,6-tetrahydrohydropyran-2-one (from step c) above; 17.9 g, 0.051 mol) was dissolved in tetrahydrofuran (200 mL) and lithium bromide (6.6 g, 0.076 mol) and lithium carbonate (5.6 g, 0.076 mol) were added. The mixture was heated at reflux for 3 h, then cooled. The mixture was filtered to remove inorganic material. The solvent was removed in vacuo and the crude residue was purified by chromatography on silica using 10-50% ethyl acetate in hexane as eluant to give the enone (11.36 g, 82%).

$^1$H NMR (400 MHz, CDCl$_3$): δ 7.68 (1H, dd, J 2.8, 6.6 Hz), 7.41 (1H, ddd, J 2.2, 4.6, 8.6 Hz), 7.11 (1H, t, J 8.4 Hz), 7.00 (1H, t, J 4.6 Hz), 4.49 (2H, t, J 6.3 Hz), 2.64 (2H, dt, J 4.6, 6.2 Hz).

e) (±) 3-(3-Bromo-4-fluorophenyl)-4-vinyl-3,4,5,6-tetrahydrohydropyran-2-one

Copper iodide (375 mg, 5 mol %) was suspended in tetrahydrofuran (300 mL) and the mixture was cooled to –78° C. To this mixture was added vinylmagnesium chloride (25 mL, 1.7M) followed by dropwise addition of 3-(3-bromo-4-fluorophenyl)-5,6-dihydropyran-2-one (from step d) above; 10.64 g, 0.039 mol) and trimethylsilyl chloride (4.97 mL, 0.039 mol). The reaction progress was monitored by thin layer chromatography. The reaction mixture was quenched by pouring, via double-ended needle, onto ammonium chloride (saturated aqueous solution). The mixture was concentrated in vacuo to remove tetrahydrofuran and the residue was extracted with ethyl acetate (3×200 mL). The pooled organic extracts were washed with brine, dried (MgSO$_4$) and evaporated. The crude residue re-dissolved in tetrahydrofuran and 1,8-diazabicyclo[5.4.0]undec-7-ene (0.3 mL) was added. This solution was stirred for 4 h. Tetrahydrofuran was removed in vacuo and the residue was purified by chromatography on silica using 30-50% ethyl acetate in hexane as eluant to give the vinyl lactone (11.5 g, 80%).

$^1$H NMR (400 MHz, CDCl$_3$): δ 7.37 (1H, d, J 6.6 Hz), 7.09 (2H, d, J 7.5 Hz), 5.61 (1H, d, J 10.3 Hz), 4.92 (1H, d, 17.1 Hz), 4.57-4.43 (2H, m), 3.44 (1H, d, J 10.9 Hz), 2.78 (1H, m), 2.16 (1H, m), 1.96 (1H, m).

f) (±) 3-(3-Bromo-4-fluorophenyl)-4-vinyltetrahydropyran-2-ol (±) 3-(3-Bromofluorophenyl)-4-vinyl-3,4,5,6-tetrahydrohydropyran-2-one (from step e) above; 9.5 g, 0.032 mol) was dissolved in ethanol (90 mL) and cerium(M) chloride was added. The resulting solution was cooled to –30° C. and sodium borohydride (1.2 g, 0.032 mol) was added portionwise. The mixture was stirred for 30 min and was then quenched with acetone (188 mL). The solvent was removed in vacuo and the residue was dispersed between ethyl acetate and water. The mixture was filtered through Celite™ to remove inorganic material. The combined organic extracts were washed with brine and dried (MgSO$_4$). The solvent was removed in vacuo to give the lactol as a yellow solid (9.07 g, 94%).

$^1$H NMR (400 MHz, CDCl$_3$) 3:2 mixture: δ 7.48 (0.4H, m), 7.37 (0.6H, m), 7.20-7.16 (0.4H, m), 7.12-7.00 (1.6H, m), 5.51-5.40 (1H, m), 5.16 (0.4H, s), 4.96-4.82 (2H, m), 4.73 (0.6H, dd, J 2.6, 8.1 Hz), 4.22-4.10 (1H, m), 3.75-3.67 (1H, m), 2.97 (0.4H, m), 2.84 (0.6H, m), 2.71 (0.4H, dd, J 2.8, 11.8 Hz), 2.54-2.45 (0.6H, m), 2.40-2.32 (1H, m), 1.80-1.60 (2H, m).

g) (2R,3R,4S)-2-[(1R)-1-(3,5-Bis(trifluoromethyl)phenyl)ethoxy]-3-(3-bromo-4-fluorophenyl)-4-vinyltetrahydropyran (±) 3-(3-Bromo-4-fluorophenyl)-4-vinyltetrahydropyran-2-ol (from step f) above; 10.32 g, 0.034 mol), (1R)-3,5-bis(trifluoromethyl)phenylethanol (11 g, 0.042 mol), Amberlyst™ (5 g) and molecular sieves (8 g) were suspended in dichloromethane (20 mL) and the mixture was shaken at 40° C. for 3 days. The resulting yellow solution was filtered, concentrated in vacuo and was purified by chromatography on silica using 1-5% ethyl acetate in hexane as eluant to give a mixture of isomers 1-3 (which were retained) and the desired isomer 4 (3.6 g, 20%) as a colourless oil.

$^1$H NMR (400 MHz, CDCl$_3$): δ 7.69 (1H, s), 7.26-7.21 (3H, m), 6.98 (1H, t J 8.4 Hz), 6.91 (1H, m), 5.43 (1H, ddd, J 7.1, 10.5, 17.4 Hz), 4.95 (1H, q, J 6.6 Hz), 4.83 (1H, d, J 10.6 Hz), 4.80 (1H, d, J 17.4 Hz), 4.16 (1H, d, J 8.3 Hz), 4.14 (1H, m), 3.56 (1H, m), 2.49 (1H, dd, J 8.3, 11.6 Hz), 2.38 (1H, m), 1.75-1.60 (2H, m), 1.40 (3H, d, J 6.6 Hz).

h) (2R,3R,4R)-2-[(1R)-1-(3,5-Bis(trifluoromethyl)phenyl)ethoxy]-3-(3-bromo-4-fluorophenyl)tetrahydropyran-4-carbaldehyde (2R,3R,4S)-2-[(1R)-1-(3,5-Bis(trifluoromethyl)phenyl)ethoxy]-3-(3-bromo-4-fluoro-phenyl)-4-vinyltetrahydropyran (from step g); 0.5 g, 0.924 mol) was dissolved in dichloromethane (10 mL) and methanol (7 mL) and ozone was bubbled through the solution at –78° C. until a blue coloration persisted. The solution was purged with nitrogen and dimethyl sulfide (0.6 mL) was added dropwise. The mixture was allowed to stir overnight. The solvent was removed in vacuo and the residue was partitioned between ethyl acetate and water. The combined organic phase was dried (MgSO$_4$) and the solvent was evaporated. The residue was purified by chromatography on silica using 10-20% ethyl acetate in hexane as eluant to afford the product aldehyde as a colourless oil (170 mg, 34%).

$^1$H NMR (CDCl$_3$): δ 1.42 (3H, d, J 6.6 Hz), 1.78-1.89 (2H, m), 2.68-2.74 (1H, m), 3.01 (1H, dd, J 7.1, 10.3 Hz), 3.59-3.64 (1H, m), 4.10-4.19 (1H, m), 4.28 (1H, d, J 7.1 Hz), 4.97 (1H, q, J 6.6 Hz), 7.03 (1H, t, J 8.3 Hz), 7.08-7.11 (1H, m), 7.31 (2H, s), 7.39 (1H, dd, J 2.2, 6.6 Hz), 7.72 (1H, s), 9.51 (1H, d, J 1.5 Hz).

(ii) (1S,4R)-4,7,7-Trimethyl-3-oxo-2-oxa-bicyclo[2.2.1]heptane-1-carboxylic acid (4R)-8-{(2R,3R,4R)-2-[(1R)-1-(3,5-bis(trifluoromethyl)phenyl)ethoxy]-3-(3-bromo-4-fluorophenyl)-tetrahydropyran-4-ylmethyl}-2-oxa-8-aza-spiro[4.5]dec-4-yl ester (1S,4R)-4,7,7-Trimethyl-3-oxo-2-oxa-bicyclo[2.2.1]heptane-1-carboxylic acid (4R)-8-aza-8-benzyloxycarbonyl-2-oxa-spiro[4.5]dec-4-yl ester (Description 9, isomer B; 100 mg, 0.21 mmol) was dissolved in methanol (20 ml) and trifluoroacetic acid (0.1 ml) and Pd (10% on carbon, 20 mg) were added under nitrogen. The mixture was purged with hydrogen gas and stirred for 30 min under a balloon of hydrogen. The mixture was purged with nitrogen and filtered to remove catalyst; solvents were removed in vacuo to give the amine as a colourless oil.

m/z 338 (M⁺+1, 100%).

The amine salt was dissolved in dichloroethane (3 ml) and triethylamine (0.056 ml, 0.4 mmol) followed by (2R,3R,4R)-2-[(1R)-1-(3,5-bis(trifluoromethyl)phenyl)ethoxy]-3-(3-bromo-4-fluorophenyl)tetrahydropyran-4-carbaldehyde (Description 14(i); 130 mg, 0.25 mmol) and sodium triacetoxyborohydride (63 mg, 0.318 mmol) and the resulting mixture was stirred for 30 min. The mixture was then diluted with dichloromethane and washed with sodium bicarbonate (saturated aqueous solution). The organic extracts were pooled, washed with brine, dried ($MgSO_4$) and concentrated in vacuo. The residue was purified by chromatography on silica gel using 1-5% methanol in dichloromethane as eluant. This afforded the product as a white solid (150 mg, 83%).

This was further purified by recrystallisation of the HCl salt from ether-ethyl acetate to give the product as white crystals (140 mg).

$^1$H NMR (500 MHz, $CDCl_3$): δ 7.69 (1H, s), 7.22 (1H, dd overlapped, J 2.0 Hz), 7.21 (3H, s), 6.98 (1H, t, J 8.3 Hz), 6.92-6.89 (1H, m), 5.00 (1H, dd, J 1.3, 4.5 Hz), 4.95 (1H, q, J 6.6 Hz), 4.18 (1H, dd, J 11.5, 4.7 Hz), 4.17-4.13 (1H, m), 4.10 (1H, d, J 8.3 Hz), 3.72 (1H, d, J 8.3 Hz), 3.66 (1H, d, J 11.0 Hz), 3.54 (1H, d, J 8.5 Hz), 3.50 (1H, br d), 2.43-2.33 (3H, m), 2.17-2.11 (1H, m), 2.07-1.83 (9H, m), 1.72-1.62 (2H, m), 1.50-1.38 (3H, m), 1.38 (3H, d, J 6.6 Hz), 1.11 (3H, s), 1.02 (3H, s), 0.94 (3H, s); m/z (ES+) 864 (M⁺+1, 100%), 866 (M⁺+1, 95%).

DESCRIPTION 15

[(2R,3R,4R)-2-[(1R)-1-(3,5-Bis(trifluoromethyl)phenyl)ethoxy]-3-(3,4-difluorophenyl)-tetrahydropyran-4-yl]methanol Sodium borohydride (24 mg, 0.63 mmol) was added to solution of 2-[1-{(2R,3R,4R)-2-[(1R)-1-(3,5-bis(trifluoromethyl)phenyl)ethoxy]-3-(3,4-difluorophenyl)-tetrahydropyran-4-carbaldehyde (see Example 2 in WO 02/16344; 107 mg, 0.23 mmol) in methanol (3 ml). The mixture was stirred for 30 minutes then quenched with saturated aqueous $NaHCO_3$ and extracted into ethyl acetate. The combined organic extracts were dried and concentrated to give the title compound (104 mg).

$^1$H NMR (360 MHz, $CDCl_3$): δ 7.70 (1H, s), 7.21 (2H, s), 7.05 (1H, m), 6.97 (1H, ddd, J 1.8, 7.4, 10.9 Hz), 6.79 (1H, m), 4.97 (1H, q, J 6.7 Hz), 4.22-4.11 (2H, m), 3.55 (1H, dt, J 2.5, 12.3 Hz), 3.39 (1H, m), 3.24 (1H, m), 2.57 (1H, dd, J 8.4, 11.2 Hz), 1.94-1.78 (2H, m), 1.68 (1H, m), 1.39 (3H, d, J 6.7 Hz), 1.18 (1H, m).

DESCRIPTION 16

Methanesulfonic acid [(2R,3R,4R)-2-[(1R)-1-(3,5-Bis(trifluoromethyl)-phenyl)ethoxy]-3-(3,4-difluorophenyl)-tetrahydropyran-4-yl]methyl ester Methanesulfonyl chloride (50 μl, 0.63 mmol) was added to a mixture of [(2R,3R,4R)-2-[(1R)-1-(3,5-bis(trifluoromethyl)phenyl)ethoxy]-3-(3,4-difluorophenyl)-tetrahydropyran-4-yl]methanol (Description 15; 235 mg, 0.49 mmol), triethylamine (133 ml, 0.97 mmol), 4-N,N-dimethylaminopyridine (3 mg, 0.02 mmol) and dichloromethane (5 ml) at 0° C. The mixture was stirred for 30 minutes, then quenched with saturated aqueous $NaHCO_3$ and extracted into dichloromethane. The combined organic extracts were dried and concentrated. The product was used in the next step without further purification.

$^1$H NMR (400 MHz, $CDCl_3$): δ 7.70 (1H, s), 7.20 (2H, s), 7.09 (1H, dt, J 8.6, 9.8 Hz), 6.88 (1H, ddd, J 2.0, 7.4, 11.0 Hz), 6.81 (1H, m), 4.97 (1H, q, J 6.7 Hz), 4.21-4.12 (2H, m), 3.95 (1H, dd, J 3.1, 9.8 Hz), 3.80 (1H, dd, J 7.4, 10.2 Hz), 3.55 (2H, dt, J 2.4, 12.1 Hz), 2.90 (3H, s), 2.58 (1H, dd, J 8.2, 11.7 Hz), 2.12 (1H, m), 1.86 (1H, m), 1.78-1.66 (1H, m), 1.39 (3H, d, J 6.7 Hz).

DESCRIPTION 17

1-Oxa-8-azaspiro[4.5]decane Hydrochloride (i) 1,1-Dimethylethyl 4-hydroxy-4-(3-trimethylsilyloxypropynyl)-1-piperidinecarboxylate Trimethyl(2-propynyloxy)silane (11.54 ml, 9.62 g, 75 mmol) was added dropwise to a stirred, cooled (−5° C.) solution of ethyl magnesium bromide (1M in tetrahydrofuran, 75 ml, 75 mmol) in tetrahydrofuran (150 ml), maintaining the internal temperature below 0° C. The mixture was stirred at 0° C. for 30 minutes, then at room temperature for 90 minutes. The mixture was cooled to −5° C. and 1,1-dimethylethyl 4-oxo-1-piperidinecarboxylate (15.0 g, 75 mmol) was added slowly, maintaining the internal temperature below 0° C. The mixture was stirred at 0° C. for 3 hours then at room temperature for 96 hours. Saturated aqueous ammonium chloride (300 ml), water (100 ml) and ethyl acetate (300 ml) were added and the layers were separated. The aqueous layer was extracted with ethyl acetate (200 ml) and the combined organic fractions were dried ($MgSO_4$) and the solvent was evaporated under reduced pressure to give the title compound (24.4 g, 100%).

$^1$H NMR (400 MHz, $CDCl_3$): δ 4.36 (2H, s), 3.80-3.70 (2H, m), 3.35-3.25 (2H, m), 1.95-1.85 (2H, m), 1.78-1.60 (3H, m), 1.48 (9H, s), 0.2 (9H, s).

(ii) 1,1-Dimethylethyl 4-hydroxy-4-(3-hydroxypropynyl)-1-piperidinecarboxylate

Tetrabutylammonium fluoride (1M in tetrahydrofuran, 80 ml, 80 mmol) was added to a solution of 1,1-dimethylethyl 4-hydroxy-4-(3-trimethylsilyloxypropynyl)-1-piperidinecarboxylate (from step (i) above; 24.4 g, 75 mmol) in tetrahydrofuran (300 ml) and the mixture was stirred at room temperature for 18 hours. The solvent was evaporated under reduced pressure and water (200 ml) was added. The mixture was extracted with ethyl acetate (2×200 ml) and the combined organic fractions were washed with water (2×200 ml) and brine (200 ml), dried ($MgSO_4$) and the solvent was evaporated under reduced pressure to give the title compound as an orange oil (16.8 g, 88%).

$^1$H NMR (400 MHz, $CDCl_3$): δ 4.32 (2H, s), 3.80-3.68 (2H, m), 3.32-3.22 (2H, m), 1.93-1.83 (2H, m), 1.75-1.65 (2H, m), 1.62 (1H, br s), 1.46 (9H, s).

(iii) 1,1-Dimethylethyl 4-hydroxy-4-(3-hydroxypropyl)-1-piperidinecarboxylate

Palladium on carbon (5%, 800 mg) was added to a solution of 1,1-dimethylethyl 4-hydroxy-4-(3-hydroxypropynyl)-1-piperidinecarboxylate (from step (ii) above; 8.37 g, 32.8 mmol) in ethanol (400 ml), acetic acid (40 ml) and water (5 ml) and the mixture was shaken under an atmosphere of hydrogen (40 psi) for 20 hours. The mixture was filtered through Hyflo™ and the solvent was evaporated under reduced pressure. The residue was purified by flash column chromatography on silica gel, eluting with isohexane/EtOAc (50:50 increasing to 0:100), to give the title compound (4.84 g, 57%).

¹H NMR (400 MHz, CDCl₃): δ 3.85-3.75 (2H, m), 3.70 (2H, t, J 6 Hz), 3.18 (2H, br t, J 14 Hz), 2.00 (2H, br s), 1.73-1.65 (2H, m), 1.63-1.48 (6H, m), 1.46 (9H, s).

(iv) 1,1-Dimethylethyl 1-oxa-3-azaspiro[4.5]decane-8-carboxylate

A solution of diethyl azodicarboxylate (3.35 ml, 21.3 mmol) in tetrahydrofuran (50 ml) was added over 15 minutes to a stirred, cooled (0° C.) solution of 1,1-dimethylethyl 4-hydroxy-4-(3-hydroxypropyl)-1-piperidinecarboxylate (from step (iii) above; 4.6 g, 17.8 mmol) and triphenylphosphine (5.58 g, 21.3 mmol) in tetrahydrofuran (150 ml) and the mixture was stirred at 0° C. for 1 hour, then at room temperature for 24 hours. The solvent was evaporated under reduced pressure and the residue was purified by flash column chromatography on silica gel, eluting with isohexane/EtOAc (75: 25 increasing to 50:50), to give the title compound (3.18 g, 70%).

¹H NMR (400 MHz, CDCl₃): δ 3.83 (2H, t, J 7 Hz), 3.63-3.53 (2H, m), 3.38-3.28 (2H, m), 1.93 (2H, quin., J 7 Hz), 1.69 (2H, t, J 7 Hz), 1.63-1.48 (4H, m), 1.46 (9H, s); m/z (ES⁺) 242 (M+1).

(v) 1-Oxa-8-azaspiro[4.5]decane Hydrochloride

Methanolic hydrogen chloride (3M, 20 ml) was added over 10 minutes to a stirred, cooled (0° C.) solution of 1,1-dimethylethyl 1-oxa-8-azaspiro[4.5]decane-8-carboxylate (from step (iv) above, 3.18 g, 13.2 mmol) in methanol (10 ml) and the mixture was stirred at room temperature for 3 hours. The solvent was evaporated under reduced pressure to give the title compound (2.29 g, 98%).

¹H NMR (400 MHz, CDCl₃): δ 3.85 (2H, t, J 7 Hz), 3.27-3.15 (4H, m), 1.98 (2H, quin., J 7 Hz), 1.86-1.75 (6H, m); m/z (ES⁺) 142 (M+1).

DESCRIPTION 18

2,2-Dimethyl-1-oxa-8-azaspiro[4.5]decane (i) 1,1-Dimethylethyl 4-(3-ethoxy-3-oxo-1-propynyl)-4-hydroxy-1-piperidinecarboxylate n-Butyllithium (175 ml, 0.28 mol) was added dropwise over 45 minutes to a stirred, cooled (−70° C.) solution of ethyl propiolate (32 ml, 0.32 mol) in tetrahydrofuran (250 ml). The mixture was stirred at −70° C. for 10 minutes, then a solution of 1,1-dimethylethyl 4-oxo-1-piperidinecarboxylate (18.6 g, 0.093 mol) in tetrahydrofuran (250 ml) was added dropwise over 1 hour maintaining the internal temperature below −70° C. The mixture was stirred at −70° C. for 1 hour and then acetic acid (21 ml) in tetrahydrofuran (50 ml) was added. The mixture was warmed to room temperature and the solvent was evaporated under reduced pressure. Saturated aqueous sodium hydrogen carbonate (300 ml) and ethyl acetate (650 ml) were added and the layers were separated. The aqueous fraction was extracted with ethyl acetate (2×650 ml) and the combined organic fractions were washed with brine, dried (Na₂SO₄) and the solvent was evaporated under reduced pressure. The residue was purified by chromatography on a short silica gel column, eluting with 1:1 isohexane:ethyl acetate, to give the title compound (29.2 g, contains trace impurity).

¹H NMR (400 MHz, CDCl₃): δ 4.24 (2H, q, J 7 Hz), 3.73-3.68 (2H, m), 3.38-3.31 (2H, m), 1.98-1.91 (2H, m), 1.80-1.72 (2H, m), 1.46 (9H, s), 1.31 (3H, t, J 7 Hz); m/z (ES⁺) 298 (M+1).

(ii) 1,1-Dimethylethyl 4-(3-ethoxy-3-oxoprop-1-yl)-4-hydroxy-1-piperidinecarboxylate Palladium on carbon (5%, 1 g) in water (10 ml) was added to a solution of 1,1-dimethylethyl 4-(3-ethoxy-3-oxo-1-propynyl)-4-hydroxy-1-piperidinecarboxylate (from step (i) above; 14.6 g, 0.046 mol) in ethanol (200 ml) and the mixture was shaken under hydrogen (45 psi) for 90 minutes. The mixture was filtered through a glass fibre pad and the solvent was evaporated under reduced pressure to give the title compound.

¹H NMR (400 MHz, CDCl₃) δ 4.14 (2H, q, J 7 Hz), 3.80 (2H, br s), 3.20-3.11 (2H, m), 2.45 (2H, t, J 7 Hz), 1.81 (2H, t, J 7 Hz), 1.58-1.42 (4H, m), 1.45 (9H, s), 1.26 (3H, t, J 7 Hz); m/z (ES⁺) 302 (M+1).

(iii) 1,1-Dimethylethyl 1-oxa-2-oxo-8-azaspiro[4.5]decane-8-carboxylate p-Toluenesulfonic acid (1.75 g, 9.2 mmol) was added to a solution of 1,1-dimethylethyl 4-(3-ethoxy-3-oxoprop-1-yl)-4-hydroxy-1-piperidinecarboxylate (from step (ii) above; 27.63 g, 0.092 mol) in toluene (250 ml) and the mixture was heated under reflux for 3 hours. The mixture was cooled and the solvent was evaporated under reduced pressure. Water (400 ml) and ethyl acetate (400 ml) were added and the layers were separated. The aqueous fraction was extracted with ethyl acetate (200 ml). The combined organic fractions were washed with brine, dried (MgSO₄) and the solvent was evaporated under reduced pressure to give the title compound (20.86 g, 88%).

¹H NMR (400 MHz, CDCl₃): δ 3.84-3.79 (2H, m), 3.26 (2H, br t), 2.62 (2H, t, J 7 Hz), 2.05 (2H, t, J 7 Hz), 1.83-1.79 (2H, m), 1.68-1.62 (2H, m), 1.46 (9H, s); m/z (ES⁺) 256 (M+1).

(iv) 1,1-Dimethylethyl 4-hydroxy-4-(3-hydroxy-3-methylbut-1-yl)-1-piperidinecarboxylate 1,1-Dimethylethyl 1-oxa-2-oxo-8-azaspiro[4.5]decane-8-carboxylate (from step (iii) above; 5.0 g, 19.58 mmol) in tetrahydrofuran (150 ml) was added dropwise over 45 min. to a stirred, cooled (0° C.) solution of methyl magnesium chloride (3M in tetrahydrofuran, 19.58 ml, 58.75 mmol) in tetrahydrofuran (150 ml). The mixture was allowed to warm to room temperature and stirred overnight. The mixture was poured into saturated aqueous ammonium chloride (200 ml) and extracted with ethyl acetate (200 ml). The organic fraction was washed with brine, dried (Na₂SO₄) and the solvent was evaporated under reduced pressure. The residue was purified by flash column chromatography on silica gel, eluting with ethyl acetate, to give the title compound (3.9 g, 69%).

¹H NMR (400 MHz, CDCl₃): δ 3.85-3.75 (2H, m), 3.20-3.10 (2H, m), 2.55-2.25 (2H, m), 1.58-1.45 (6H, m), 1.46 (9H, s), 1.24 (6H, s); m/z (ES⁺) 214 (M+1-C₄H₈—H₂O).

(v) 2,2-Dimethyl-1-oxa-8-azaspiro[4.5]decane

Trifluoroacetic acid (10 ml) was added to a solution of 1,1-dimethylethyl 4-hydroxy-4-(3-hydroxy-3-methylbut-1-yl)-1-piperidinecarboxylate (from step (iv) above; 3.9 g, 13.57 mmol) in dichloromethane (10 ml) and the mixture was stirred at room temperature overnight. The solvent was evaporated under reduced pressure and the residue was purified by flash column chromatography on silica gel, eluting with CH₂Cl₂/MeOH/NH₃(Aq.) (90:10:1) to give the title compound (2.04 g, 89%).

¹H NMR (400 MHz, CDCl₃): δ 3.27-3.17 (4H, m), 1.95-1.82 (6H, m), 1.70 (2H, d, J 13.4 Hz), 1.22 (6H, s); m/z (ES⁺) 170 (M+1).

DESCRIPTION 19

6-Oxa-2-azaspiro[3.4]octan-8-ol (i) 1-Benzyloxycarbonyl-3-azetidinecarboxylic acid 3-Azetidinecarboxylic acid (4.0 g, 39.6 mmol) was dissolved in 1N sodium hydroxide solution (40 mL) and cooled to 0° C. Benzyl chloroformate (5.9 mL, 41 mmol) was added followed by further 1N sodium hydroxide solution (41 mL) dropwise. The mixture was stirred vigorously for 16 hrs then made acidic with 2N hydrochloric acid. This suspension was extracted with dichloromethane (2×100 mL) and the extracts dried over $MgSO_4$. Concentration yielded the title compound (9.3 g, 39.6 mmol, 100%).

$^1$H NMR (400 MHz, $CDCl_3$): δ 7.37-7.29 (5H, m), 5.10 (2H, s), 4.21 (4H, d, J 7.5 Hz), 3.43 (1H, quintet, J 7.5 Hz).

(ii) Methyl 1-benzyloxycarbonyl-3-azetidinecarboxylate

1-Benzyloxycarbonyl-3-azetidinecarboxylic acid (from step (i); 9.3 g, 39.6 mmol) was dissolved in methanol (100 mL) and toluene (100 mL), and cooled to 0° C. A solution of 2M trimethylsilyldiazomethane in hexanes was then added dropwise until bubbling had ceased and the yellow colour persisted. Acetic acid was then added dropwise until the yellow colour disappeared. Concentration of the solution yielded the title compound as an oil (9.48 g, 38 mmol, 96%).

$^1$H NMR (400 MHz, $CDCl_3$): δ 7.36-7.31 (5H, m), 5.10 (2H, s), 4.19 (4H, d, J 7.8 Hz), 3.75 (3H, s), 3.39 (1H, quintet, J 7.8 Hz).

(iii) Benzyl 3-(1,2-dihydroxyethyl)-3-(hydroxymethyl)azetidine-1-carboxylate

Methyl 1-benzyloxycarbonyl-3-azetidinecarboxylate (from step (ii); 10.1 g, 40 mmol) was dissolved in tetrahydrofuran (120 mL) and cooled to −78° C. A solution of lithium hexamethyldisilazide in tetrahydrofuran (1M, 58 mL, 58 mmol) was slowly added and the solution warmed to 0° C. After 15 mins. at this temperature, the resulting solution was cooled back to −78° C. and tert-butyldimethylsilyloxy acetaldehyde was added and stirred to room temperature over 2 hrs and quenched with water (200 mL). This suspension was extracted with ethyl acetate (2×200 mL). The extracts were dried ($MgSO_4$) and concentrated. The residue was flushed through silica with 25% ethyl acetate in hexanes to give a 1:2 mixture of 1-benzyl 3-methyl 3-(2-{[tert-butyl(dimethyl)silyl]oxy}-1-hydroxyethyl)azetidine-1,3-dicarboxylate: starting material (4.24 g).

This mixture was dissolved in tetrahydrofuran (30 mL) and treated with lithium borohydride (395 mg, 18 mmol). After 2 hrs at room temperature, the mixture was quenched with 1N sodium hydroxide solution (100 mL) and extracted with ethyl acetate (2×100 mL). The extracts were dried ($MgSO_4$) and concentrated to give crude benzyl 3-(2-{[tert-butyl(dimethyl)silyl]oxy}-1-hydroxyethyl)-3-(hydroxylmethyl)azetidine-1-carboxylate. This was dissolved in tetrahydrofuran (100 mL) and treated with 1M tetra-n-butylammonium fluoride in tetrahydrofuran (10 mL, 10 mmol). After stirring for 1 hr at room temperature, water (200 mL) was added and the mixture extracted with ethyl acetate (2×200 mL). The combined extracts were dried ($MgSO_4$) and concentrated. The residue was purified by silica chromatography to give the title compound as an oil (956 mg, 3.4 mmol).

$^1$H NMR (400 MHz, $CDCl_3$): δ 7.37-7.29 (5H, m), 5.09 (2H, s), 3.96-3.64 (9H, m), 3.13 (2H, br m), 1.69 (1H, br m).

(iv) Benzyl 8-hydroxy-6-oxa-2-azaspiro[3.4]octane-2-carboxylate

Benzyl 3-(1,2-dihydroxyethyl)-3-(hydroxymethyl)azetidine-1-carboxylate (from step (iii); 956 mg, 3.4 mmol) was dissolved in dichloromethane (150 mL) and dibutyltin oxide (17 mg) was added. p-Toluenesulfonyl chloride (686 mg, 3.6 mmol) was added and the solution was cooled to 0° C. Triethylamine (520 μL, 3.75 mmol) was added dropwise and the solution was then allowed to stir at ambient temperature for 16 hrs. Further triethylamine (260 μL, 1.9 mmol) was added and after stirring for 2 hrs, water (250 mL) was added. The mixture was extracted with dichloromethane (2×250 mL), and the extracts dried ($MgSO_4$) then concentrated. The residue was purified by silica chromatography to give the title compound as an oil (456 mg, 1.7 mmol, 51%).

$^1$H NMR (400 MHz, $CDCl_3$): δ 7.37-7.29 (5H, m), 5.10 (2H, s), 4.31-4.27 (2H, m), 3.97 (2H, dd, J 9.1, 24 Hz), 3.94-3.91 (1H, m), 3.86 (1H, d, J 9.5 Hz), 3.85 (2H, dd, J 9.1, 20 Hz), 3.74 (1H, dd, J 1.9, 10.2 Hz), 1.95 (1H, d, J 4.4 Hz).

(v) 6-Oxa-2-azaspiro[3.4]octan-3-ol

Benzyl 8-hydroxy-6-oxa-2-azaspiro[3.4]octane-2-carboxylate (from step (iv); 456 mg, 1.7 mmol) was dissolved in methanol (20 mL) and 10% palladium on carbon (50 mg) added. This suspension was hydrogenated at 20 psi hydrogen for 2 hrs then filtered. The filtrate was concentrated to give the title compound as a gum (214 mg, 1.66 mmol, 98% yield).

m/z ($ES^+$) 130 (M+H).

DESCRIPTION 20

4-Hydroxy-1-oxa-8-azaspiro[4.5]decane (i) tert-Butyl 4-(3-{[tert-butyl(dimethyl)silyl]oxy}propylidene)piperidine-1-carboxylate 3-{[tert-Butyl(dimethyl)silyl]oxy}propyl)(triphenyl)phosphonium bromide (J. Med Chem 1990, 33, 1958) (5.15 g, 0.01 mol) was suspended in toluene and azeotroped to remove any moisture. It was then suspended in 1,2-dimethoxyethane (20 mL) and n-butyllithium (7.0 mL, 1.6M. 0.011 mol) was added dropwise until a yellow coloration persisted. tert-Butyl 4-oxopiperidine-1-carboxylate (2 g, 0.01 mol) was added and the mixture was heated at reflux overnight. The cooled mixture was diluted with water and extracted with ethyl acetate (2×50 mL), dried ($MgSO_4$) and concentrated in vacuo. The crude yellow oil was purified on silica using 10-30% ethyl acetate in iso-hexane as eluant.

$^1$H NMR (500 MHz, $CDCl_3$): δ 0.01 (6H, s), 0.84 (9H, s), 2.06-2.18 (4H, m), 2.20 (2H, t, J 7.0 Hz), 3.33 (4H, multiplet centre (mc)), 3.53 (2H, t, J 7.0 Hz), 5.24 (1H, t, J 7.2 Hz); m/z ($ES^+$) 256 ($M^+$+1-100, 100%).

(ii) tert-Butyl 4-(1,3-dihydroxypropyl)-4-hydroxypiperidine-1-carboxylate tert-Butyl 4-(3-{[tert-butyl(dimethyl)silyl]oxy}propylidene)piperidine-1-carboxylate (from step (i) above; 0.9 g) was dissolved in tetrahydrofuran (1 mL); tetra-n-butylammonium fluoride (2.5 mL, 1M in THF) was added and the mixture was stirred for 30 min until tlc analysis (50:50 ethyl acetate:hexane) showed that all starting material had reacted. This mixture was concentrated in vacuo. The crude product was re-dissolved in tert-butanol (5 mL) and water (1 mL) and N-methylmorpholine N-oxide (322 mg) was added and stirred until dissolved. Osmium tetroxide (0.15 mL, 2.5% in t-butanol) was added and the mixture was stirred for 12 h. This mixture was concentrated in vacuo. The crude product was purified by chromatography on silica using 1-6% methanol in dichloromethane as eluant to afford the product (480 mg).

¹H NMR (500 MHz, CDCl₃): δ 1.45 (9H, s), 1.40-1.85 (6H, m), 3.02-3.15 (2H, m), 3.60 (1H, dd, J 12, 4 Hz), 3.85-4.00 (4H, m); m/z (ES⁺) 176 (M⁺+1-100, 100%).

(iii) tert-Butyl 4-hydroxy-1-oxa-8-azaspiro[4.5]decane-8-carboxylate tert-Butyl 4-(1,3-dihydroxypropyl)-4-hydroxypiperidine-1-carboxylate (from step (ii) above; 480 mg) was dissolved in dichloromethane and p-toluenesulfonyl chloride was added followed by triethylamine (0.49 mL) and the mixture was stirred for 12 h. An additional aliquot of triethylamine was added (0.49 mL) and the mixture stirred for 48 h. This mixture was concentrated in vacuo. The crude product was purified by chromatography on silica using 50-95% ethyl acetate in iso-hexane as eluant to afford the product (300 mg).

¹H NMR (500 MHz, CDCl₃): δ 1.45 (9H, s), 1.48-1.67 (2H, br m), 1.95 (1H, mc), 2.32 (1H, mc), 3.18 (2H, mc), 3.72-3.83 (1H, br m), 3.85 (2H, mc), 3.99 (2H, mc); m/z (ES⁺) 158 (M⁺+1-100, 100%).

(iv) 4-Hydroxy-1-oxa-8-azaspiro[4.5]decane trifluoroacetate tert-Butyl 4-hydroxy-1-oxa-8-azaspiro[4.5]decane-8-carboxylate (from step (iii) above; 300 mg) was dissolved in dichloromethane and trifluoroacetic acid (2 mL) was added. The solution was stirred for 2 h and was concentrated in vacuo to afford the product as a colorless oil.

¹H NMR (500 MHz, CDCl₃): δ 1.61-1.66 (1H, m), 1.89-2.06 (3H, m), 2.27-2.31 (2H, m), 3.20-3.33 (3H, m), 3.35-3.42 (1H, m), 3.85 (1H, mc), 3.99 (1H, q, J 8.5 Hz), 4.07 (1H, dd, J 6.5, 4.0 Hz); m/z (s⁺) 158 (M⁺+1, 100%).

DESCRIPTION 21

4-Hydroxy-3,3-dimethyl-2-oxa-8-azaspiro[4.5]decane (i) Benzyl 4-(acetyloxy)-3,3-dimethyl-1-oxo-2-oxa-8-azaspiro[4.5]decane-8-carboxylate A solution of 1-benzyl 4-ethyl piperidine-1,4-dicarboxylate (2.35 g) was dissolved in tetrahydrofuran (30 mL) and was cooled to −78° C. Lithium bis(trimethylsilyl)amide (9 mL, 1M) was added dropwise under nitrogen and the solution was stirred for 30 min at −20° C. The solution was re-cooled to −78° C. and 1,1-dimethyl-2-oxoethyl acetate (1.17 g) in tetrahydrofuran (5 mL) was added and the mixture was stirred for 30 min. The mixture was quenched (NaHCO₃, 30 mL) and the mixture was extracted with ethyl acetate (2×50 mL). The extracts were combined, washed with brine, dried (MgSO₄) and were concentrated in vacuo. The crude product was purified by chromatography on silica using 25-75% ethyl acetate in iso-hexane as eluant to afford the product (1.4 g).

m/z (ES⁺) 376 (M⁺+1, 100%).

(ii) Benzyl 4-(1,2-dihydroxy-2-methylpropyl)-4-(hydroxymethyl)piperidine-1-carboxylate Benzyl 4-(acetyloxy)-3,3-dimethyl-1-oxo-2-oxa-8-azaspiro[4.5]decane-8-carboxylate (from step (i) above; 1.4 g) was dissolved in tetrahydrofuran and lithium borohydride (81 mg) was added. The mixture was heated under reflux for 2 h, cooled and quenched carefully with water and HCl (30 mL, 5N). The mixture was extracted with ethyl acetate and dried (MgSO₄), and concentrated in vacuo. The crude product was purified by chromatography on silica using 2-5% methanol in dichloromethane as eluant to afford the product (340 mg).

m/z (ES⁺) 338 (M⁺+1, 80%) 320 (M⁺+1-18, 100%).

(iii) Benzyl 4-hydroxy-3,3-dimethyl-2-oxa-8-azaspiro[4.5]decane-8-carboxylate

Benzyl 4-(1,2-dihydroxy-2-methylpropyl)-4-(hydroxymethyl)piperidine-1-carboxylate (from step (iii) above; 340 mg) was dissolved in dichloromethane and p-toluenesulfonyl chloride (190 mg) was added, followed by triethylamine (0.14 mL). This mixture was stirred for 2 h and a second aliquot of triethylamine was added and the mixture was stirred for 12 h. The mixture was concentrated in vacuo. The crude product was purified by chromatography on silica using 50-100% ethyl acetate in iso-hexane as eluant to afford the product (190 mg).

¹H NMR (500 MHz, CDCl₃): δ 1.18 (3H, s), 1.29 (3H, s), 1.46-1.59 (2H, m), 1.62-1.78 (2H, m), 3.00-3.13 (2H, m), 3.55 (1H, d, J 9.3 Hz), 3.73 (1H, d, J 9.3 Hz), 3.84-3.95 (2H, m), 5.12 (2H, s), 7.29-7.36 (5H, m); m/z (ES⁺) 320 (M⁺+1, 100%).

(iv) 4-Hydroxy-3,3-dimethyl-2-oxa-8-azaspiro[4.5]decane

Benzyl 4-hydroxy-3,3-dimethyl-2-oxa-8-azaspiro[4.5]decane-8-carboxylate (from step (iii) above; 180 mg) was dissolved in methanol and palladium on carbon (5%) was added. The mixture was hydrogenated at atmospheric pressure for 30 min. The catalyst was removed by filtration through Hyflo™ and the solvent was evaporated in vacuo to afford the product as a white solid.

¹H NMR (500 MHz, CDCl₃): δ 1.13 (3H, s), 1.24 (3H, s), 1.45-1.50 (2H, m), 1.67-1.79 (2H, m), 2.64-2.71 (2H, m), 2.89-3.00 (2H, m), 3.47 (1H, s), 3.59 (1H, d, J 9.2 Hz), 3.72 (1H, d, J 9.2 Hz); m/z (ES⁺) 186 (M⁺+1, 100%).

DESCRIPTION 22

1-Oxa-8-aza[4.5]decan-3-ol (i) tert-Butyl 4-hydroxy-4-{3-[(trimethylsilyl)oxy]prop-1-yn-1-yl}piperidine-1-carboxylate Ethyl magnesium bromide in tetrahydrofuran (55 mL, 1M, 55 mmol) was slowly added to a solution of trimethyl(prop-2-yn-1-yloxy)silane in tetrahydrofuran (40 mL) maintaining a temperature of 0° C. After the complete addition the mixture was stirred at ambient temperature for 45 min before a solution of tert-butyl piperidin-4-one-1-carboxylate (10 g, 50 mmol) in tetrahydrofuran (40 mL) was slowly added at 0° C. Subsequently the reaction mixture was stirred for 18 h at ambient temperature. Then saturated ammonium chloride solution was added and the mixture was stirred vigorously until the dissolution of all solids. The phases were separated and the aqueous was extracted with ethyl acetate. The combined organic phases were washed with brine, dried over magnesium sulfate, filtered and concentrated under reduced pressure to give 16.42 g of desired product (96%) as a yellow oil.

¹H NMR (360 MHz, CDCl₃): δ 4.16 (2H, s), 3.55 (2H, br m), 3.12 (2H, ddd, J 3.8, 9.3, 12.8 Hz), 1.74-1.66 (2H, m), 1.53 (2H, ddd, J 4, 9, 12.8 Hz), 1.28 (9H, s).

(ii) tert-Butyl 4-hydroxy-4-(3-hydroxyprop-1-yn-1-yl)piperidine-1-carboxylate tert-Butyl 4-hydroxy-4-{3-[(trimethylsilyl)oxy]prop-1-yn1-1-yl}piperidine-1-carboxylate (crude from step (i); 16.42 g, ca. 50 mmol) was stirred with tetrabutylammonium fluoride (90 mmol) in tetrahydrofuran (170 mL) at ambient temperature for 18 h. Then the solvent was removed in vacuo and the residue partitioned between water and ethyl acetate. The organic phase was separated and the aqueous was extracted with ethyl acetate. The combined organic phases were washed with brine, dried over magnesium sulfate, filtered and concentrated under reduced pressure to give the crude product as an amber oil, which was purified by flash chromatography on silica gel, eluting with 5% methanol in dichloromethane to yield the desired diol (10.87 g, 85%).

$^1$H NMR (360 MHz, CDCl$_3$): δ 4.32 (2H, br s), 3.80-3.69 (2H, br m), 3.28 (2H, ddd, J 3.5, 9.2, 13.2 Hz), 1.92-1.84 (2H, br m), 1.74 (2H, ddd, J 3.8, 8.9, 12.7 Hz), 1.46 (9H, s).

(iii) tert-Butyl 4-hydroxy-4-(3-hydroxyprop-1-ene-1-yl}piperidine-1-carboxylate tert-Butyl 4-hydroxy-4-(3-hydroxyprop-1-yn-1-yl)piperidine-1-carboxylate (from step (ii); 10 g, 39.2 mmol) was stirred at ambient temperature with Lindlar's catalyst (5% Pd on CaCO$_3$ poisoned with Pb) (4.15 g, 2 mmol of Pd) in ethanol under hydrogen (p≧1 atm) for 18 h. Then the catalyst was filtered off and the filtrate concentrated under reduced pressure to give 10.2 g of the desired cis-olefin as a pale yellow oil.

$^1$H NMR (360 MHz, CDCl$_3$): δ 5.66-5.56 (2H, m), 4.33 (2H, d, J 5.2 Hz), 3.77-3.67 (2H, m), 3.30-3.24 (2H, m), 1.73-1.63 (4H, m), 1.46 (9H, s).

(iv) tert-Butyl 1-oxa-8-azaspiro[4.5]dec-3-ene-8-carboxylate

To a solution of tert-butyl 4-hydroxy-4-(3-hydroxyprop-1-ene-1-yl)piperidine-1-carboxylate (from step (iii); 8.79 g, 34.2 mmol) and triethylamine (7.6 g, 75.2 mmol) in tetrahydrofuran (170 mL), methanesulfonyl chloride (4.31, 37.6 mmol) was slowly added so that the internal temperature stayed between −10 and −5° C. After the complete addition the temperature was allowed to rise to 12° C. and was kept at that temperature until all starting diol was turned over (monitored by TLC (silica gel, 1:1 hexane/ethyl acetate)). Subsequently the reaction mixture was stirred for 2 days to complete the cyclisation before it was concentrated under reduced pressure. The residue was treated with water under ice-cooling, followed by extraction with ethyl acetate. The combined organic layers were washed with brine, dried over magnesium sulfate, filtered and concentrated under reduced pressure to give 9 g of crude product as yellow oil. This was purified by flash chromatography on silica gel, eluting with a gradient solvent system of 10-20% ethyl acetate in hexane to give 5.79 g of the desired spirocyclic product (64%).

$^1$H NMR (360 MHz, CDCl$_3$): δ 5.88 (1H, ddd, J 1.7, 1.7, 6.1 Hz), 5.74 (1H, ddd, J 2.2, 2.2, 6.3 Hz), 4.64 (2H, dd, J 1.6, 2.2 Hz), 3.79-3.69 (2H, br m), 3.28 (2H, ddd, J 3.64, 10.5, 13.8 Hz), 1.68-1.54 (4H, m), 1.46 (9H, s).

(v) tert-Butyl 1-oxa-8-aza[4.5]decan-3-ol-8-carboxylate

Borane-tetrahydrofuran-complex solution in tetrahydrofuran (16.7 mL, 1M. 16.7 mmol) was added to a solution of tert-butyl 1-oxa-8-azaspiro[4.5]dec-3-ene-8-carboxylate (from step (iv) above; 2 g, 8.37 mmol) in tetrahydrofuran (25 mL) at 0° C. After 1 h at room temperature, a mixture of 35% w/w hydrogen peroxide solution (6 mL, ca. 67 mmol) and 4 M sodium hydroxide solution (17 mL) was slowly added at 0° C. Then the reaction mixture was stirred at room temperature for 18 h before it was partitioned between water and ethyl acetate. The aqueous phase was extracted with ethyl acetate. The combined organic phases were washed with saturated sodium sulfite solution, then brine and finally dried over magnesium sulfate, filtered and concentrated to give the crude mixture of products as a colourless oil. The mixture was separated by flash chromatography on silica gel, eluting with a gradient solvent system of 50-100% ethyl acetate in hexane, then 1-2% methanol in ethyl acetate to furnish 1.03 g of the title compound (48%).

$^1$H NMR (360 MB, CDCl$_3$): δ 4.51-4.49 (1H, m), 3.92 (1H, dd, J 4.4, 10.1 Hz), 3.84-3.79 (1H, m), 3.59 (1H, br s), 3.38-3.30 (1H, m), 1.96 (1H, dd, J 6.3, 13.6 Hz), 1.85-1.79 (2H, m), 1.73-1.63 (2H, m), 1.58-1.50 (2H, m), 1.45 (9H, s).

(vi) 1-Oxa-8-aza[4.5]decan-3-ol trifluoroacetate tert-Butyl 1-oxa-8-aza[4.5]decan-3-ol-8-carboxylate (from step (v) above; 1 g, 3.89 mmol) was stirred in a 1:1 v/v mixture of trifluoroacetic acid and dichloromethane (8 mL) at ambient temperature for 0.5 h. The reaction mixture was concentrated in vacuo to give 1.55 g of a pale amber oil.

$^1$H NMR (360 MD, CDCl$_3$): δ 4.58-4.61 (1H, m), 3.87-4.02 (2H, m), 3.37-3.47 (2H, m), 2.26-1.75 (6H, m); m/z (ES$^+$) 158.

DESCRIPTION 23

(2R,3R,4R,αRS)-α-(3-Buten-1-yl)-2-{(1R)-1-[3,5-bis(trifluoromethyl)phenyl]ethoxy}tetrahydro-3-phenyl-2H-pyran-4-methanol 3-Butenylmagnesium bromide (0.5M in tetrahydrofuran, 75 mL, 37.5 mmol) was added slowly to a stirred, cooled −78° C. solution of (2R,3R,4R)-2-{(1R)-1-[3,5-bis(trifluoromethyl)phenyl]ethoxy}tetrahydro-3-phenyl-2H-pyran-4-carboxaldehyde (WO 00/56727A1; 11.1 g, 24.9 mmol) in tetrahydrofuran (125 mL). The mixture was stirred at −78° C. for 3 hours, then at room temperature for 1.5 hour. Saturated aqueous ammonium chloride (20 mL) was added slowly, followed by ethyl acetate (300 mL). The layers were separated and the organic layer was washed with brine (100 mL). The combined aqueous layers were extracted with ethyl acetate (100 mL), the combined organic layers were dried (Na$_2$SO$_4$), and the solvent was evaporated under reduced pressure. The residue was purified by column chromatography on silica gel, eluting with hexane/EtOAc (97:3 increasing to 80:20), to give the title compound (8:1 mixture of alcohol diastereoisomers) as a colorless oil (10 g, 80%).

$^1$H NMR (500 MHz, CDCl$_3$) (major isomer described): δ 7.66 (1H, s), 7.28-7.15 (5H, m), 7.04 (2H, m), 5.67 (1H, m), 4.94 (2H, m), 4.87 (1H, m), 4.25 (1H, d, J 8.6 Hz), 4.17 (1H, m), 3.53 (1H, m), 3.22 (1H, m), 2.85 (1H, m), 2.01 (1H, m), 1.90 (1H, m), 1.78 (2H, m), 1.53 (2H, m), 1.36 (3H, d, J 6.6 Hz), 1.31 (1H, m).

DESCRIPTION 24

(2R,3R,4R,αR or S)-α-(3-Buten-1-yl)-2-{(1R)-1-[3,5-bis(trifluoromethyl)phenyl]ethoxy}tetrahydro-3-phenyl-2H-pyran-4-methyl Methanesulfonate Methanesulfonyl chloride (1.61 mL, 2.3 g, 21 mmol) was added dropwise to a stirred, cooled (−78° C.) solution of (2R,3R,4R,αRS)-α-(3-buten-1-yl)-2-{(1R)-1-[3,5-bis(trifluoromethyl)phenyl]ethoxy}tetrahydro-3-phenyl-2H-pyran-4-methanol (Description 23, 8:1 mixture of diastereoisomers; 3.5 g, 6.97 mmol) and triethylamine (5 mL, 3.5 g, 35 mmol) in dichloromethane (70 mL). The mixture was allowed to warm to room temperature over 1.5 hours, then water (20 mL) and ethyl acetate (100 mL) were added. The layers were separated and the organic layer was washed with brine (100 mL). The combined aqueous layers were extracted with ethyl acetate (100 mL), the combined organic layers were dried (Na$_2$SO$_4$), and the solvent was evaporated under reduced pressure. The residue was purified by column chromatography on silica gel, eluting with hexane/EtOAc (95:5 increasing to 80:20), to give the title compound (single diastereoisomer) as a colorless oil (2.76 g, 68%).

¹H NMR (500 MHz, CDCl₃): δ 7.65 (1H, s), 7.25 (3H, m), 7.14 (2H, s), 7.07 (2H, m), 5.62 (1H, m), 4.92 (3H, m), 4.39 (1H, t, J 6.6 Hz), 4.19 (1H, m), 4.17 (1H, d, J 8.6 Hz), 3.54 (1H, dt, J 2.3, 11.0 Hz), 2.91 (3H, s), 2.80 (1H, dd, J 8.3, 11.6 Hz), 2.15 (1H, m), 1.90 (3H, m), 1.80 (1H, m), 1.68 (2H, m), 1.36 (3H, d, J 6.6 Hz).

DESCRIPTION 25

(2RS,5R or S)-5-((2R,3R,4R)-{(1R)-1-[3,5-Bis(trifluoromethyl)phenyl]-ethoxy}tetrahydro-3-phenyl-2H-pyran-4-yl)-1,2,5-pentanetriol 5-Methanesulfonate 2-Methyl-2-propanol (2 mL) was added to a solution of AD-mix-α (0.5 g) in water (2 mL) and the mixture was stirred vigorously at room temperature for 10 minutes. The yellow solution was then added to (2R,3R,4R,αR or S)-α-(3-buten-1-yl)-2-{(1R)-1-[3,5-bis(trifluoromethyl)phenyl]ethoxy}tetrahydro-3-phenyl-2H-pyran-4-methyl methanesulfonate (Description 24; 0.24 g, 0.41 mmol) and the resulting mixture was stirred vigorously at room temperature overnight. Sodium sulfite (2 g) was added and the mixture was stirred for 30 minutes. Water (10 mL) and ethyl acetate (10 mL) were added, the layers were separated and the organic layer was washed with brine (100 mL). The combined aqueous layers were extracted with ethyl acetate (100 mL), the combined organic layers were dried (Na₂SO₄), and the solvent was evaporated under reduced pressure. The residue was purified by column chromatography on silica gel, eluting with hexane/EtOAc (50:50 increasing to 10:90), to give the title compound (3:1 mixture of alcohol diastereoisomers) as a colorless oil (0.20 g, 79%).

¹H NMR (500 MHz, CD₃OD): δ 7.70 (1H, s), 7.30 (2H, s), 7.21 (3H, m), 7.17 (2H, m), 5.00 (1H, q, J 6.5 Hz), 4.33 (2H, m), 4.10 (1H, m), 3.65 (1H, m), 3.35 (3H, m), 3.03, 3.02 (3H, each s), 2.78 (1H, dd, J 8.3, 11.6 Hz), 2.27 (1H, m), 1.90-1.40 (6H, m), 1.33 (3H, d, J 6.6 Hz).

DESCRIPTION 26

(2RS,5R or S)-5-((2R,3R,4R)-{(1R)-1-[3,5-Bis(trifluoromethyl)phenyl]-ethoxy}tetrahydro-3-phenyl-2H-pyran-4-yl)-1,2,5-pentanetriol 5-Methanesulfonate The title compound (1:3 mixture of alcohol diastereoisomers) was prepared from (2R,3R,4R,αR or S)-α-(3-buten-1-yl)-2-{(1R)-1-[3,5-bis(trifluoromethyl)phenyl]-ethoxy}tetrahydro-3-phenyl-2H-pyran-4-methyl methanesulfonate (Description 24) according to the method of Description 25, using AD-mix-β instead of AD-mix-α.

¹H NMR (500 MHz, CD₃OD): δ 7.70 (1H, s), 7.30 (2H, s), 7.21 (3H, m), 7.17 (2H, m), 5.00 (1H, q, J 6.5 Hz), 4.33 (2H, m), 4.10 (1H, m), 3.65 (1H, m), 3.35 (3H, m), 3.03, 3.02 (3H, each s), 2.78 (1H, dd, J 8.3, 11.6 Hz), 2.27 (1H, m), 1.90-1.40 (6H, m), 1.33 (3H, d, J 6.6 Hz).

DESCRIPTION 27

(2RS,5R or S)-5-((2R,3R,4R)-{(1R)-1-[3,5-Bis(trifluoromethyl)phenyl]-ethoxy}tetrahydro-3-phenyl-2H-pyran-4-yl)-1,2,5-pentanetriol 1-(4-Methylbenzenesulfonate) 5-Methanesulfonate 4-Methylbenzenesulfonyl chloride (53 mg, 0.28 mmol) was added to a mixture of (2RS,5R or S)-5-((2R,3R,4R)-{(1R)-1-[3,5-bis(trifluoromethyl)phenyl]ethoxy}-tetrahydro-3-phenyl-2H-pyran-4-yl)-1,2,5-pentanetriol 5-methanesulfonate (3:1 mixture of alcohol diastereoisomers; Description 25; 0.17 g, 0.28 mmol), dibutyltin oxide (1.4 mg, 5.6 μmol) and triethylamine (39 μL, 0.28 mmol) in dichloromethane (1.4 mL) and the mixture was stirred vigorously at room temperature for 3 hours. The solvent was evaporated under reduced pressure and the residue was purified by column chromatography on silica gel, eluting with hexane/EtOAc (80:20 increasing to 50:50), to give the title compound (3:1 mixture of alcohol diastereoisomers) as a colorless oil (0.142 g, 67%).

¹H NMR (500 MHz, CD₃OD): δ 7.75 (2H, d, J 8.2 Hz), 7.71 (1H, s), 7.40 (2H, d, J 8.2 Hz), 7.30 (2H, s), 7.20 (3H, m), 7.13 (2H, m), 5.00 (1H, q, J 6.5 Hz), 4.32 (1H, d, J 8.5 Hz), 4.26 (1H, t, J 6.4 Hz), 4.11 (1H, m), 3.85-3.75 (2H, m), 3.62 (2H, m), 3.47 (1H, m), 3.01, 3.00 (3H, each s), 2.74 (1H, dd, J 8.3, 11.6 Hz), 2.43 (3H, s), 2.20 (1H, m), 1.90-1.40 (6H, m), 1.33 (3H, d, J 6.6 Hz).

DESCRIPTION 28

(2RS,5R or S)-5-((2R,3R,4R)-{(1R)-1-[3,5-Bis(trifluoromethyl)phenyl]-ethoxy}tetrahydro-3-phenyl-2H-pyran-4-yl)-1,2,5-pentanetriol 1-(4-Methylbenzenesulfonate) 5-Methanesulfonate The title compound (1:3 mixture of alcohol diastereoisomers) was prepared from (2RS,5R or S)-5-((2R,3R,4R)-{(1R)-1-[3,5-bis(trifluoromethyl)phenyl]ethoxy}-tetrahydro-3-phenyl-2H-pyran-4-yl)-1,2,5-pentanetriol 5-methanesulfonate (1:3 mixture of alcohol diastereoisomers; Description 26) according to the method of Description 27.

¹H NMR (500 MHz, CD₃OD): δ 7.75 (2H, d, J 8.2 Hz), 7.71 (1H, s), 7.40 (2H, d, J 8.2 Hz), 7.30 (2H, s), 7.20 (3H, m), 7.13 (2H, m), 5.00 (1H, q, J 6.5 Hz), 4.32 (1H, d, J 8.5 Hz), 4.26 (1H, t, J 6.4 Hz), 4.11 (1H, m), 3.85-3.75 (2H, m), 3.62 (2H, m), 3.47 (1H, m), 3.01, 3.00 (3H, each s), 2.74 (1H, dd, J 8.3, 11.6 Hz), 2.43 (3H, s), 2.20 (1H, m), 1.90-1.40 (6H, m), 1.33 (3H, d, J 6.6 Hz).

DESCRIPTION 29

(2R,3R,4R)-2-{(1R)-1-[3,5-Bis(trifluoromethyl)phenyl]ethoxy}tetrahydro-4-[(2R or S)-oxiranyl]-3-phenyl-2H-pyran; and (2R,3R,4R)-2-{(1R)-1-[3,5-Bis(trifluoromethyl)phenyl]ethoxy}tetrahydro-4-[(2S or R)-oxiranyl]-3-phenyl-2H-pyran (Isomers A and B)

Dimethylsulfoxide (10 mL) was added to sodium hydride (60% dispersion in mineral oil, 385 mg, 9.6 mmol) and the mixture was stirred at room temperature for 30 minutes. Tetrahydrofuran (20 mL) was added and the mixture was cooled to −10° C. Trimethylsulfonium iodide (2.13 g, 10.4 mmol) in dimethylsulfoxide (10 mL) was added and the mixture was stirred at 0° C. for 10 minutes. (2R,3R,4R)-2-{(1R)-1-[3,5-Bis(trifluoromethyl)phenyl]ethoxy}tetrahydro-3-phenyl-2H-pyran-4-carboxaldehyde (WO 00/56727A1; 3.58 g, 8.0 mmol) in tetrahydrofuran (10 mL) was added and the mixture was stirred at 0° C. for 30 minutes, then at room temperature for 30 minutes. Water (100 mL) was added and the mixture was extracted with ethyl acetate (3×100 mL). The combined organic fractions were washed with water (4×100 mL) and brine (100 mL), dried (MgSO₄) and the solvent was evaporated under reduced pressure. The residue was purified by column chromatography on silica gel, eluting with hexane/

EtOAc (85:15 increasing to 80:20), to give (2R,3R,4R)-2-{(1R)-1-[3,5-bis(trifluoromethyl)phenyl]ethoxy}tetrahydro-4-[(2R or S)-oxiranyl]-3-phenyl-2H-pyran (Isomer A; single diastereoisomer; epoxide stereochemistry unassigned) as a colorless oil (1.37 g, 37%); $^1$H NMR (500 MHz, CDCl$_3$): δ 7.67 (1H, s), 7.23 (5H, m), 7.01 (2H, m), 4.97 (1H, q, J 6.6 Hz), 4.28 (1H, d, J 8.4 Hz), 4.16 (1H, br d, J 11 Hz), 3.53 (1H, br t, J 11 Hz), 2.65 (1H, dd, J 8.4 Hz), 2.60 (1H, m), 2.34 (1H, t, J 4.5 Hz), 1.95 (1H, dd, J 4.5, 2.7 Hz), 1.84 (1H, br d, J 11 Hz), 1.68 (1H, m), 1.57 (1H, m), 1.37 (3H, d, J 6.6 Hz); and (2R,3R,4R)-2-{(1R)-1-[3,5-bis(trifluoromethyl)phenyl]ethoxy}tetrahydro-4-[(2S or R)-oxiranyl]-3-phenyl-2H-pyran (Isomer B; single diastereoisomer; epoxide stereochemistry unassigned) as a colorless oil (0.51 g, 14%); $^1$H NMR (500 MHz, CDCl$_3$): δ 7.67 (1H, s), 7.27-7.20 (5H, m), 7.08 (2H, m), 4.96 (1H, q, J 6.6 Hz), 4.25 (1H, d, J 8.3 Hz), 4.13 (1H, br d, J 12 Hz), 3.54 (1H, br t, J 12 Hz), 2.68 (1H, m), 2.61 (1H, dd, J 11.5, 8.3 Hz), 2.50 (1H, t, J 4.6 Hz), 2.46 (1H, dd, J 4.6, 2.8 Hz), 2.03 (1H, m), 1.60 (1H, br d, J 12 Hz), 1.49 (1H, m), 1.37 (3H, d, J 6.6 Hz); and a 1:1 mixture of Isomer A and Isomer B (1.16 g, 31%).

DESCRIPTION 30

(2R,3R,4R,αR or S)-α-{[(2-Hydroxyethyl)thio]methyl}-2-{(1R)-1-[3,5-bio(trifluoromethyl)phenyl]ethoxy}tetrahydro-3-phenyl-2H-pyran-4-methanol; and (2R,3R,4R,αS or R)-α-{[(2-hydroxyethyl)thio]methyl}-2-{(1R)-1-[3,5-bis(trifluoromethyl)phenyl]ethoxy}tetrahydro-3-phenyl-2H-pyran-4-methanol 2-Mercaptoethanol (0.70 mL, 0.78 g, 10 mmol) was added to a degassed mixture of (2R,3R,4R)-2-{(1R)-1-[3,5-bis(trifluoromethyl)phenyl]ethoxy}tetrahydro-4-[(2R or S)-oxiranyl]-3-phenyl-2H-pyran and (2R,3R,4R)-2-{(1R)-1-[3,5-bis(trifluoromethyl)-phenyl]ethoxy}tetrahydro-4[(2S or R)-oxiranyl]-3-phenyl-2H-pyran (Description 29, 1:1 mixture of diastereoisomers; 0.46 g, 1 mmol) and potassium hydroxide (0.56 g, 10 mmol) in propan-2-ol (10 mL) and the mixture was heated under reflux for 4 hours. The mixture was cooled and the solvent was evaporated under reduced pressure. Aqueous sodium hydroxide (1M, 20 mL) was added and the mixture was extracted with diethyl ether (3×20 mL). The combined organic fractions were washed with aqueous sodium hydroxide (1M, 2×20 mL) and brine (20 mL), dried (MgSO$_4$) and the solvent was evaporated under reduced pressure to give the title compound (1:1 mixture of alcohol epimers) as a yellow oil (0.54 g, 100%).

$^1$H NMR (500 MHz, CDCl$_3$): δ 7.66 (1H, s), 7.26-7.23 (3H, m), 7.18 and 7.15 (2H, each s), 7.05 (2H, m), 4.95 (1H, m), 4.25, 4.23 (1H, each d, J 8.3 Hz), 4.18 (1H, m), 3.62-3.53 (3H, m), 3.30 (1H, m), 2.90-1.51 (10H, m), 1.36 (3H, d, J 6.6 Hz).

DESCRIPTION 31

(2R,3R,4R,αR)-α-2-Propenyl-2-{(1R)-1-[3,5-bis(trifluoromethyl)phenyl]-ethoxy}tetrahydro-3-phenyl-2H-pyran-4-methanol Allylmagnesium bromide (15.4 mL, 15.4 mmol) was slowly added to a stirred, cooled –40° C. solution of chlorobis[(1S,2R,3S,5S)-2,6,6-trimethylbicyclo[3.1.1]hept-3-yl]borane (5.91 g, 18 mmol) in diethyl ether (20 mL). The mixture was warmed to room temperature and stirred for 1 hour before cooling to –78° C. (2R,3R,4R)-2-{(1R)-1-[3,5-Bis(trifluoromethyl)phenyl]-ethoxy}tetrahydro-3-phenyl-2H-pyran-4-carboxaldehyde (WO 00/56727A1; 5.5 g, 12.3 mmol) in diethyl ether (10 mL) was slowly added and the mixture was stirred at –78° C. for 1.5 hours. The mixture was warmed to room temperature and stirred for a further 1.5 hours. The mixture was cooled to –78° C. and aqueous sodium acetate (3M, 20 mL) then aqueous hydrogen peroxide (31% wt, 10 mL) were added. The mixture was allowed to warm to room temperature and stirred overnight. The layers were separated and the aqueous layer was extracted with ethyl acetate (2×150 mL). The combined organic fractions were dried (MgSO$_4$) and the solvent was evaporated under reduced pressure. The residue was purified by column chromatography on silica gel, eluting with EtOAc/hexane (90:10), to give the title compound as a yellow oil (4.7 g, 78%).

$^1$H NMR (360 MHz, CDCl$_3$): δ 1.25 (3H, d, J 7 Hz), 1.34 (1H, d, J 6.6 Hz), 1.54 (1H, d, J 9 Hz), 1.80 (1H, m), 2.05 (1H, m), 2.14 (1H, m), 2.88 (1H, m), 3.27 (1H, m), 3.53 (1H, m), 4.17 (1H, m), 4.25 (1H, d, J 8.6 Hz), 4.94-4.98 (2H, m), 5.03 (1H, m), 5.60 (1H, m), 7.03-7.05 (2H, m), 7.18-7.24 (5H, m), 7.65 (1H, s).

DESCRIPTION 32

(2R,3R,4R,αS)-α-2-Propenyl-2-{(1R)-1-[3,5-bis(trifluoromethyl)phenyl]-ethoxy}tetrahydro-3-phenyl-2H-pyran-4-methanol Prepared from (2R,3R,4R)-2-{(1R)-1-[3,5-bis(trifluoromethyl)phenyl]ethoxy}-tetrahydro-3-phenyl-2H-pyran-4-carboxaldehyde (WO 00/56727A1), allylmagnesium bromide and chlorobis[(1R,2S,3R,5R)-2,6,6-trimethylbicyclo[3.1.1]hept-3-yl]borane according to the method of Description 31.

$^1$H NMR (360 MHz, CDCl$_3$): δ 1.36 (3H, d, J 6.6 Hz), 1.58 (1H, m), 1.80 (1H, m), 1.95 (1H, m), 2.17 (1H, m), 2.23 (1H, m), 2.55 (1H, m), 3.30 (1H, m), 3.55 (1H, m), 4.17 (1H, m), 4.23 (1H, d, J 8.2 Hz), 4.94 (1H, m), 5.03-5.06 (2H, m), 5.59 (1H, m), 7.03-7.04 (2H, m), 7.05 (2H, m), 7.16-7.24 (3H, m), 7.69 (1H, s), 7.85 (1H, s).

DESCRIPTION 33

(1R)-1-((2R,3R,4R)-{(1R)-1-[3,5-Bis(trifluoromethyl)phenyl]ethoxy}-tetrahydro-3-phenyl-2H-pyran-4-yl)-1,3-propanediol (2R,3R,4R,αR)-α-2-Propenyl-2-{(1R)-1-[3,5-bis(trifluoromethyl)phenyl]ethoxy}-tetrahydro-3-phenyl-2H-pyran-4-methanol (Description 31; 1.0 g, 2 mmol) was dissolved in dichloromethane/methanol (1:1, 30 mL), cooled to –78° C. and purged with nitrogen and then oxygen. Ozone was bubbled through the mixture for 15-20 minutes, until a blue coloration persisted. The mixture was purged with oxygen, then nitrogen, warmed to 0° C. and sodium borohydride (0.3 g, 8 mmol) was added in portions. The mixture was stirred at 0° C. for 30 minutes, aqueous ammonium chloride (10%, 40 mL) was added and the mixture was extracted with dichloromethane (2×75 mL). The combined organic fractions were dried (MgSO$_4$) and the solvent was evaporated under reduced pressure. The residue was purified by column chromatography on silica gel, eluting with EtOAc/hexane (50:50) to give the title compound as a colorless oil (0.5 g, 50%).

$^1$H NMR (500 MHz, CD$_3$OD): δ 1.32 (3H, d, J 6.6 Hz), 1.41 (1H, m), 1.55 (1H, m), 1.62 (1H, m), 1.75 (1H, m), 1.86 (1H, m), 2.81 (1H, dd, J 8.6, 11.5 Hz), 3.45-3.51 (2H, m), 3.62 (1H, dt, J$_d$ 2.3, J$_t$ 12.0 Hz), 4.1 (1H, m), 4.36 (1H, d, J 8.7 Hz), 4.99 (1H, q, J 6.5 Hz), 7.09-7.11 (2H, m), 7.16-7.21 (3H, m), 7.31 (2H, s), 7.70 (1H, s).

DESCRIPTION 34

(1S)-1-((2R,3R,4R)-{(1R)-1-[3,5-Bis(trifluoromethyl)phenyl]ethoxy}-tetrahydro-3-phenyl-2H-pyran-4-yl)-1,3-propanediol Prepared from (2R,3R,4R,αS)-α-2-propenyl-2-{(1R)-1-[3,5-bis(trifluoromethyl)phenyl]ethoxy}tetrahydro-3-phenyl-2H-pyran-4-methanol (description 32) according to the method of Description 33.

$^1$H NMR (360 MHz, CDCl$_3$): δ 1.35 (3H, d, J 6.6 Hz), 1.57-1.60 (3H, m), 1.80 (1H, m), 1.95 (1H, m), 2.06 (1H, m), 2.43 (1H, m), 2.50 (1H, m), 3.54-3.57 (3H, m), 3.80 (1H, m), 4.23 (1H, m), 4.24 (1H, d, J 8.1 Hz), 4.93 (1H, m), 7.02-7.04 (2H, m), 7.16-7.23 (5H, m), 7.65 (1H, s).

DESCRIPTION 35

(1R)-1-((2R,3R,4R)-{(1R)-1-[3,5-Bis(trifluoromethyl)phenyl]ethoxy}-tetrahydro-3-phenyl-2H-pyran-4-yl)-1,3-propanediol Dimethylsulfonate (1R)-1-((2R,3R,4R)-{(1R)-1-[3,5-bis(trifluoromethyl)phenyl]ethoxy}tetrahydro-3-phenyl-2H-pyran-4-yl)-1,3-propanediol (Description 33; 0.5 g, 1 mmol) was dissolved in dichloromethane (5 mL) and cooled to −10° C. Triethylamine (0.56 mL, 4 mmol) was added followed by methanesulfonyl chloride (0.23 mL, 3 mmol) dropwise. The mixture was stirred at −20° C. for 30 minutes, then at room temperature for 15 minutes. Water (75 mL) was added and the mixture was extracted with dichloromethane (3×75 mL). The combined organic fractions were dried (MgSO$_4$) and the solvent was evaporated under reduced pressure to give the title compound as a colorless foam (0.65 g, 100%).

$^1$H NMR (500 MHz, CDCl$_3$): δ 1.35 (3H, d, J 6.7 Hz), 1.65 (1H, m), 1.77 (1H, m), 2.05 (1H, m), 2.15-2.20 (2H, m), 2.75 (1H, m), 2.84 (3H, s), 2.92 (3H, s), 3.55 (1H, t, J 12 Hz), 4.15-4.22 (4H, m), 4.55 (1H, m), 4.92 (1H, q, J 6.5 Hz), 7.09-7.13 (4H, m), 7.24-7.26 (3H, m), 7.65 (1H, s).

DESCRIPTION 36

(1S)-1-((2R,3R,4R)-1-{(1R)-1-[3,5-Bis(trifluoromethyl)phenyl]ethoxy}-tetrahydro-3-phenyl-2H-pyran-4-yl)-1,3-propanediol Dimethylsulfonate Prepared from (1S)-1-((2R,3R,4R)-{(1R)-1-[3,5-bis(trifluoromethyl)phenyl]-ethoxy}tetrahydro-3-phenyl-2H-pyran-4-yl)-1,3-propanediol (Description 34) according to the method of Description 35.

$^1$H NMR (400 MHz, CDCl$_3$): δ 1.35 (3H, d, J 6.6 Hz), 1.60 (1H, m), 1.80-1.90 (2H, m), 1.99 (1H, m), 2.48 (1H, m), 2.55 (1H, m), 2.72 (3H, s), 2.92 (3H, s), 3.60 (1H, m), 4.1 (1H, m), 4.20-4.22 (3H, m), 4.45 (1H, m), 4.48 (1H, m), 7.08-7.14 (4H, m), 7.26-7.29 (3H, m), 7.66 (1H, s).

DESCRIPTION 37

Methyl (2R,3R,4R)-2-{(1R)-1-[3,5-Bis(trifluoromethyl)phenyl]ethoxy}-tetrahydro-3-phenyl-2H-pyran-4-carboxylate Trimethylsilyldiazomethane (2.0M in hexanes, 3.5 mL, 7 mmol) was added in portions over 1 hour to a solution of (2R,3R,4R)-2-{(1R)-1-[3,5-bis(trifluoromethyl)phenyl]ethoxy}tetrahydro-3-phenyl-2H-pyran-4-carboxylic acid (WO 00/56727A1; 3.2 g, 6.9 mmol) in a mixture of methanol (10 mL) and toluene (7 mL). The solvent was evaporated under reduced pressure and the residue was purified by column chromatography on silica gel, eluting with EtOAc/hexane (80:20), to give the title compound as a colorless solid (2.4 g, 73%).

$^1$H NMR (500 MHz, CDCl$_3$): δ 7.67 (1H, s), 7.22 (5H, m), 7.07 (2H, m), 4.96 (1H, q, J 6.6 Hz), 4.28 (1H, d, J 8.2 Hz), 4.17 (1H, br d, J 11 Hz), 3.58 (1H, br t, J 11 Hz), 3.45 (3H, s), 3.04 (1H, dd, J 8.2, 11.4 Hz), 2.81 (1H, br t, J 11 Hz), 1.94 (1H, br q, J 11 Hz), 1.86 (1H, br d, J 11 Hz), 1.38 (3H, d, J 6.6 Hz).

DESCRIPTION 38

(2R,3R,4R)-α,α-Di-(2-propenyl)-2-{(1R)-1-[3,5-bis(trifluoromethyl)phenyl]-ethoxy}tetrahydro-3-phenyl-2H-pyran-4-methanol Allylmagnesium bromide (1.0M in hexanes, 8.8 mL, 8.8 mmol) was added slowly to a stirred, cooled (0° C.) solution of methyl(2R,3R,4R)-2-{(1R)-1-[3,5-bis(trifluoromethyl)phenyl]ethoxy}tetrahydro-3-phenyl-2H-pyran-4-carboxylate (Description 37; 1.4 g, 2.9 mmol) in tetrahydrofuran (10 mL). The mixture was warmed to room temperature and stirred for 30 minutes. Saturated aqueous ammonium chloride (50 mL) was added and the mixture was extracted with ethyl acetate (3×30 mL). The combined organic fractions were dried (MgSO$_4$) and the solvent was evaporated under reduced-pressure. The residue was purified by column chromatography on silica gel, eluting with EtOAc/hexane (80:20), to give the title compound as a colorless oil (1.48 g, 95%).

$^1$H NMR (400 MHz, CDCl$_3$): δ 7.66 (1H, s), 7.22 (3H, m), 7.16 (2H, s), 7.11 (2H, m), 5.88-5.70 (2H, m), 5.08-4.97 (4H, m), 4.89 (1H, q, J 6.6 Hz), 4.22 (1H, d, J 7.7 Hz), 4.15-4.09 (1H, m), 3.50 (1H, br t, J 12 Hz), 2.84 (1H, dd, J 10.9, 7.7 Hz), 2.21-2.11 (5H, m), 1.78 (1H, br d, J 12 Hz), 1.64 (1H, br q, J 12 Hz), and 1.35 (3H, d, J 6.6 Hz).

DESCRIPTION 39

3-((2R,3R,4R)-{(1R)-1-[3,5-Bis(trifluoromethyl)phenyl]ethoxy}tetrahydro-3-phenyl-2H-pyran-4-yl)-1,3,5-propanetriol (2R,3R,4R)-α,α-Di-(2-propenyl)-2-{(1R)-1-[3,5-bis(trifluoromethyl)phenyl]ethoxy}-tetrahydro-3-phenyl-2H-pyran-4-methanol (Description 39; 1.48 g, 2.8 mmol) was dissolved in dichloromethane/methanol (1:1, 30 mL), cooled to −78° C. and purged with nitrogen and then oxygen. Ozone was bubbled through the mixture for 15-20 minutes, until a blue coloration persisted. The mixture was purged with oxygen, then nitrogen, warmed to 0° C. and sodium borohydride (0.21 g, 5.6 mmol) was added in portions. The mixture was stirred at 0° C. for 30 minutes, aqueous ammonium chloride (10%, 50 mL) was added and the mixture was extracted with dichloromethane (2×50 mL). The combined organic fractions were dried (MgSO$_4$) and the solvent was evaporated under reduced pressure. The residue was purified by column chromatography on silica gel, eluting with EtOAc/hexane (50:50), to give the title compound as a colorless oil (0.80 g, 55%).

$^1$H NMR (400 MHz, CDCl$_3$): δ 7.66 (1H, s), 7.19 (3H, m), 7.14 (2H, s), 7.04 (2H, m), 4.89 (1H, q, J 6.6 Hz), 4.25 (1H, d, J 8.0 Hz), 4.17 (1H, br d, J 11 Hz), 3.80 (2H, br s), 3.70 (1H, br m), 3.56 (2H, m), 3.40 (1H, s), 3.24 (1H, br s), 2.84 (1H, br s), 2.72 (1H, dd, J 11.3, 8.0 Hz), 2.37 (1H, br t, J 11 Hz), 1.89-1.80 (2H, m), 1.70-1.56 (3H, m), 1.34 (3H, d, J 6.6 Hz), 1.19-1.13 (1H, m).

DESCRIPTION 40

3-((2R,3R,4R)-{(1R)-1-[3,5-Bis(trifluoromethyl)
phenyl]ethoxy}tetrahydro-3-phenyl-2H-pyran-4-yl)-
1,3,5-propanetriol 1,5-Dimethylsulfonate Methanesulfonyl chloride (0.24 mL, 0.36 g, 3.2 mmol) was added slowly to a stirred, cooled (−10° C.) solution of 3-((2R,3R,4R)-{(1R)-1-[3,5-bis(trifluoromethyl)phenyl]ethoxy}tetrahydro-3-phenyl-2H-pyran-4-yl)-1,3,5-propanetriol (Description 39; 0.80 g, 1.5 mmol) and triethylamine (0.48 mL, 0.35 g, 3.5 mmol) in dichloromethane (8 mL). The mixture was stirred at −10° C. for 20 minutes, then water (25 mL) was added and the mixture was extracted with dichloromethane (3×30 mL). The combined organic fractions were washed with aqueous citric acid (10%, 30 mL) and saturated aqueous sodium carbonate (30 mL), dried ($MgSO_4$) and the solvent was evaporated under reduced pressure to give the title compound as a colorless foam (1.0 g, 100%).

$^1$H NMR (500 MHz, $CDCl_3$): δ 7.67 (1H, s), 7.28 (3H, m), 7.13 (4H, m), 4.90 (1H, q, J 6.6 Hz), 4.34-4.15 (6H, m), 3.68 (1H, s), 3.58 (1H, br t, J 11 Hz), 2.97 (3H, s), 2.95 (3H, s), 2.78 (1H, m), 2.22 (1H, br t, J 11 Hz), 1.97-1.94 (3H, m), 1.83-1.76 (2H, m), 1.61 (1H, m), 1.35 (3H, d, J 6.6 Hz).

DESCRIPTION 41

(2R,3R,4R)-2-{(1R)-1-[3,5-Bis(trifluoromethyl)phe-
nyl]ethoxy}tetrahydro-4-[(2R or S)-oxiranyl]-3-phe-
nyl-2H-pyran; and (2R,3R,4R)-2-{(1R)-1-[3,5-Bis
(trifluoromethyl)phenyl]ethoxy}tetrahydro-4-[(2S or
R)-oxiranyl]-3-phenyl-2H-pyran (Isomers A and B)

Dimethylsulfoxide (10 mL) was added to sodium hydride (60% dispersion in mineral oil, 385 mg, 9.6 mmol) and the mixture was stirred at room temperature for 30 minutes. Tetrahydrofuran (20 mL) was added and the mixture was cooled to −10° C. Trimethylsulfonium iodide (2.13 g, 10.4 mmol) in dimethylsulfoxide (10 mL) was added and the mixture was stirred at 0° C. for 10 minutes. (2R,3R,4R)-2-{(1R)-1-[3,5-Bis(trifluoromethyl)phenyl]ethoxy}tetrahydro-3-phenyl-2H-pyran-4-carboxaldehyde (WO 00/56727A1; 3.58 g, 8.0 mmol) in tetrahydrofuran (10 mL) was added and the mixture was stirred at 0° C. for 30 minutes, then at room temperature for 30 minutes. Water (100 mL) was added and the mixture was extracted with ethyl acetate (3×100 mL). The combined organic fractions were washed with water (4×100 mL) and brine (100 mL), dried ($MgSO_4$) and the solvent was evaporated under reduced pressure. The residue was purified by column chromatography on silica gel, eluting with hexane/EtOAc (85:15 increasing to 80:20), to give: (2R,3R,4R)-2-{(1R)-1-[3,5-bis(trifluoromethyl)phenyl]ethoxy}tetrahydro-4-[(2R or S)-oxiranyl]-3-phenyl-2H-pyran (Isomer A; single diastereoisomer; epoxide stereochemistry unassigned) as a colorless oil (1.37 g, 37%); $^1$H NMR (500 MHz, $CDCl_3$): δ 7.67 (1H, s), 7.23 (5H, m), 7.01 (2H, m), 4.97 (1H, q, J 6.6 Hz), 4.28 (1H, d, J 8.4 Hz), 4.16 (1H, br d, J 11 Hz), 3.53 (1H, br t, J 11 Hz), 2.65 (1H, dd, J 8.4 Hz), 2.60 (1H, m), 2.34 (1H, t, J 4.5 Hz), 1.95 (1H, dd, J 4.5, 2.7 Hz), 1.84 (1H, br d, J 11 Hz), 1.68 (1H, m), 1.57 (1H, m), 1.37 (3H, d, J 6.6 Hz); and (2R,3R,4R)-2-{(1R)-1-[3,5-bis(trifluoromethyl)phenyl]ethoxy}tetrahydro-4-[(2S or R)-oxiranyl]-3-phenyl-2H-pyran (Isomer B; single diastereoisomer; epoxide stereochemistry unassigned) as a colorless oil (0.51 g, 14%); $^1$H NMR (500 MHz, $CDCl_3$): δ 7.67 (1H, s), 7.27-7.20 (5H, m), 7.08 (2H, m), 4.96 (1H, q, J 6.6 Hz), 4.25 (1H, d, J 8.3 Hz), 4.13 (1H, br d, J 12 Hz), 3.54 (1H, br t, J 12 Hz), 2.68 (1H, m), 2.61 (1H, dd, J 11.5, 8.3 Hz), 2.50 (1H, t, J 4.6 Hz), 2.46 (1H, dd, J 4.6, 2.8 Hz), 2.03 (1H, m), 1.60 (1H, br d, J 12 Hz), 1.49 (1H, m), 1.37 (3H, d, J 6.6 Hz); and a 1:1 mixture of Isomer A and Isomer B (1.16 g, 31%).

EXAMPLE 1

(4R)-8-[(2R,3R,4R)-2-[(1R)-1-(3,5-Bis(trifluorom-
ethyl)phenyl)ethoxy]-3-(3-bromo-4-fluorophenyl)
tetrahydropyran-4-yl]methyl-2-oxa-3-aza-spiro[4.5]
decan-4-ol (1S,4R)-4,7,7-Trimethyl-3-oxo-2-oxa-bicyclo[2.2.1]heptane-1-carboxylic acid (4R)-8-{(2R,3R,4R)-2-[(1R)-1-(3,5-bis(trifluoromethyl)phenyl)ethoxy]-3-(3-bromo-4-fluorophenyl)-tetrahydropyran-4-ylmethyl}-2-oxa-8-aza-spiro [4.5]dec-4-yl ester (Description 14; 130 mg, 0.15 mmol) was dissolved in dichloromethane (3 ml) and the solution was cooled to −78° C. under nitrogen. A solution of diisobutylaluminium hydride (0.9 ml, 1M in toluene) was added dropwise and the solution was stirred for 30 min. Methanol (0.1 ml) was added dropwise and the resulting quenched solution was poured carefully onto sodium hydroxide (10 ml, 4M. This was stirred for 30 min. The organic extracts were pooled, washed with brine, dried ($MgSO_4$) and concentrated in vacuo. The residue was purified by chromatography on silica gel using 1-5% methanol in dichloromethane as eluant. This afforded the product as a white foam (96 mg, 93%).

This was further purified by recrystallisation of the HCl salt from ether-dichloromethane to give the product as white crystals (86 mg).

$^1$H NMR (500 MHz, $CDCl_3$): δ 7.69 (1H, s), 7.23 (1H, dd, J 2.1, 6.5 Hz), 7.21 (2H, s), 6.98 (1H, t, J 8.3 Hz), 6.89-6.92 (1H, m), 4.95 (1H, q, J 6.5 Hz), 4.10-4.14 (2H, m), 4.03 (1H, dd, J 4.6, 10.0 Hz), 3.90 (1H, dd, J 1.7, 4.4 Hz), 3.65 (1H, dd, J 2.2, 10.0 Hz), 3.59 (1H, d, J 8.5 Hz), 3.54 (1H, d, J 8.5 Hz), 3.51 (1H, dd, J 12.1, 2.0 Hz), 2.39-2.37 (1H, m), 2.37 (1H, dd, J 8.3, 11.0 Hz), 2.28-2.20 (1H, m), 2.12-1.84 (6H, m), 1.73-1.68 (1H, m), 1.49-1.43 (2H, m), 1.39 (3H, d, J 6.6 Hz); m/z ($ES^+$) 684 ($M^+$+1, 95%), 686 ($M^+$+1, 100%).

EXAMPLE 2

(4RS)-8-[(2R,3R,4R)-2-[(1R)-1-(3,5-Bis(trifluorom-
ethyl)phenyl)ethoxy]-3-phenyl-tetrahydropyran-4-yl]
methyl-2-oxa-8-aza-spiro[4.5]decan-4-ol Triethylamine (140 μL, 1.0 mmol) was added to a suspension of 2-oxa-8-aza-spiro[4.5]decan-4-ol hydrochloride (Description 8; 0.1 g, 0.54 mmol) in 1,2-dichloroethane (2 ml). After 10 minutes, (2R,3R,4R)-2-[(1R)-1-(3,5-bis(trifluoromethyl)phenyl)ethoxy]-3-phenyl-tetrahydropyran-4-carbaldehyde (see Example 43 in WO 00/56727; 0.24 g, 0.54 mmol) was added as a solution in 1,2-dichloroethane (3 ml). The mixture was stirred at room temperature for 30 minutes then sodium triacetoxyborohydride (0.2 g, 0.94 mmol) was added. The reaction was stirred at room temperature overnight. The mixture was partitioned between dichloromethane and brine. The organic layer was dried ($MgSO_4$) and concentrated in vacuo. The residue was purified by preparative thin layer chromatography, eluting with 5% methanol/dichloromethane, to give the title compound (72 mg, 23%).

$^1$H NMR (400 MHz, $CDCl_3$): δ 7.58 (1H, s), 7.16-7.15 (3H, m), 7.09 (2H, s), 6.95-6.92 (2H, m), 4.87 (1H, q, J 6.6 Hz), 4.12 (1H, d, J 8.3 Hz), 4.07 (1H, dd, J 3.5, 11.7 Hz), 3.96-3.93 (1H, m), 3.83-3.81 (1H, m), 3.59-3.43 (4H, m), 2.41-2.38 (1H, m), 2.34-2.29 (1H, m), 2.21-2.15 (1H, m), 2.05-1.85 (5H, m), 1.74-1.66 (2H, m), 1.45-1.34 (4H, m), 1.29 (3H, d, J 6.6 Hz).

EXAMPLE 3

(4S)-8-[(2R,3R,4R)-2-[(1R)-1-(3,5-Bis(trifluoromethyl)phenyl)ethoxy]-3-(4-fluorophenyl)-tetrahydropyran-4-yl]methyl-2-oxa-8-aza-spiro[4.5]decan-4-ol A solution of (1S,4R)-4,7,7-trimethyl-3-oxo-2-oxa-bicyclo[2.2.1]heptane-1-carboxylic acid (4RS)-8-{(2R,3R,4R)-2-[(1R)-1-(3,5-bis(trifluoromethyl)phenyl)ethoxy]-3-(4-fluorophenyl)-tetrahydropyran-4-ylmethyl}-2-oxa-8-azaspiro[4.5]dec-4-yl ester (Description 12; 138 mg, 0.175 mmol) in dichloromethane (5 ml) was cooled to −78° C. and diisobutylaluminium hydride (1.5M in toluene, 0.5 ml, 0.75 mmol) added. The reaction was stirred for 30 minutes then quenched by the addition of 2M aqueous sodium hydroxide solution. The mixture was allowed to warm to room temperature then dried over Na$_2$SO$_4$ and filtered through Celite™. The filtrate was concentrated in vacuo and the residue purified by preparative thin layer chromatography, eluting with 7% methanol/dichloromethane to give the title compound (27 mg, 26%).

$^1$H NMR (360 MHz, CDCl$_3$): δ 7.67 (1H, s), 7.17 (2H, s), 7.00-6.92 (4H, m), 4.95 (1H, q, J 6.5 Hz), 4.15-4.11 (2H, m), 4.04-4.00 (1H, m), 3.90-3.89 (1H, m), 3.67-3.60 (2H, m), 3.54-3.48 (2H, m), 2.52-2.42 (1H, m), 2.41-2.36 (1H, m), 2.34-2.14 (2H, m), 2.10-1.87 (4H, m), 1.86-1.76 (1H, m), 1.75-1.67 (1H, m), 1.55-1.40 (4H, m), 1.36 (3H, d, J 6.5 Hz); m/z (ES+) 606 (M+H)$^+$.

EXAMPLE 4

(4R)-8-[(2R,3R,4R)-2-[(1R)-1-(3,5-Bis(trifluoromethyl)phenyl)ethoxy]-3-(4-fluorophenyl)-tetrahydropyran-4-yl]methyl-2-oxa-8-aza-spiro[4.5]decan-4-ol The title compound was prepared from (1S,4R)-4,7,7-trimethyl-3-oxo-2-oxa-bicyclo[2.2.1]heptane-1-carboxylic acid (4R)-8-{(2R,3R,4R)-2-[(1R)-1-(3,5-bis(trifluoromethyl)phenyl)ethoxy]-3-(4-fluorophenyl)-tetrahydropyran-4-ylmethyl}-2-oxa-8-aza-spiro[4.5]decyl ester (Description 13) according to the method of Example 3.

$^1$H NMR (360 MHz, CDCl$_3$): δ 7.67 (1H, s), 7.17 (2H, s), 7.03-6.89 (4H, m), 4.95 (1H, q, J 6.5 Hz), 4.13 (2H, m), 4.02 (1H, dd, J 4.7, 9.8 Hz), 3.90 (1H, m), 3.65 (1H, dd, J 2.0, 10.2 Hz), 3.59 (1H, d, J 8.2 Hz), 3.53 (1H, dd, J 8.6 Hz), 3.50 (1H, dd, J 1.6, 12.1 Hz), 2.57-1.52 (11H, m), 1.60-1.40 (4H, m), 1.36 (3H, d, J 6.5 Hz); m/z (ES+) 606 (M+H)$^+$.

EXAMPLE 5

(4RS)-8-[(2R,3R,4R)-2-[(1R)-1-(3,5-Bis(trifluoromethyl)phenyl)ethoxy]-3-(3,4-difluorophenyl)-tetrahydropyran-4-yl]methyl-2-oxa-8-aza-spiro[4.5]decan-4-ol A mixture of methanesulfonic acid [(2R,3R,4R)-2-[(1R)-1-(3,5-bis(trifluoromethyl)-phenyl)ethoxy]-3-(3,4-difluorophenyl)-tetrahydropyran-4-yl]methyl ester (Description 16; 0.275 g, 0.49 mmol), 2-oxa-8-aza-spiro[4.5]decan-4-ol hydrochloride (Description 8; 0.1 g, 0.37 mmol), potassium carbonate (237 g, 1.7 mmol) and acetonitrile (3 ml) was stirred at 55° C. overnight and then at 65° C. for 18 hours. The mixture was treated with water and extracted into dichloromethane. The combined organic extracts were dried (Na$_2$SO$_4$) and concentrated. The residue was purified by preparative TLC (dichloromethane:methanol) to give the title compound.

m/z (ES+) 624 (M+H)$^+$.

EXAMPLE 6

8-[(2R,3R,4R)-2-[(1R)-1-(3,5-Bis(trifluoromethyl)phenyl)ethoxy]-3-(4-fluorophenyl)tetrahydropyran-4-yl]methyl-2-oxa-3-aza-spiro[4.5]decane A mixture of 2-[1-{(2R,3R,4R)-2-[(1R)-1-(3,5-bis(trifluoromethyl)phenyl)ethoxy]-3-(4-fluorophenyl)-tetrahydropyran-4-carbaldehyde (Description 11; 0.15 g, 0.32 mmol), 2-oxa-8-azaspiro[4.5]decane hydrochloride (0.85 g, 0.48 mmol), triethylamine (50 µL, 0.49 mmol), sodium triacetoxyborohydride (0.136 g, 0.64 mmol) and dichloroethane (3 ml) was stirred at room temperature for 2 hours. The mixture was treated with sodium bicarbonate and extracted into dichloromethane. The combined organic extracts were dried (Na$_2$SO$_4$) and concentrated. The residue was purified by chromatography on alumina (grade III) using ethyl acetate in hexane (10-50%) to give the title compound.

$^1$H NMR (360 MHz, CDCl$_3$): δ 1.36 (3H, d, J 6.6 Hz), 1.38-1.55 (5H, m), 1.61 (2H, t, J 7.1 Hz), 1.82-2.05 (6H, m), 2.18-2.31 (2H, m), 2.37 (1H, dd, J 10.5, 8.4 Hz), 3.43 (2H, s), 3.51 (1H, br t), 3.77 (2H, t, J 7.1 Hz), 4.10-4.14 (2H, m), 4.95 (1H, q, J 6.6 Hz), 6.91-7.01 (4H, m), 7.17 (2H, s), 7.67 (1H, s); m/z (ES+) 591 (M$^+$+H, 100%).

EXAMPLE 7

8-[(2R,3S,4S)-2-[(1R)-1-(3,5-Bis(trifluoromethyl)phenyl)ethoxy]-3-phenyl(tetrahydropyran-4-yl)]methyl-1,1-dimethyl-2-oxa-8-aza-spiro[4.5]decane A mixture of (2R,3S,4S)-2-[(1R)-1-(3,5-bis(trifluoromethyl)phenyl)ethoxy]-3-phenyl(tetrahydropyran)-4-aldehyde (see Example 43 in WO 00/56727) and 1,1-dimethyl-2-oxa-8-azaspiro[4.5]decane (Bioorg. and Med. Chem. Lett. 2002, 12, 1759) was reacted and purified according to the procedure described in Example 6 to give the title compound.

$^1$H NMR (360 MHz, CDCl$_3$): δ 1.07 (3H, s), 1.08 (3H, s), 1.20-1.37 (3H, m), 1.46 (3H, d, J 6.6 Hz), 1.50-1.64 (3H, m), 1.78-1.91 (3H, m), 2.0-2.15 (3H, m), 2.57-2.71 (3H, m), 2.97-3.02 (1H, m), 3.72-3.79 (3H, m), 4.04-4.10 (1H, m), 4.41 (1H, d, 3.2 Hz), 4.95 (1H, q, J 6.6 Hz), 7.24-7.26 (5H, m), 7.36 (2H, s), 7.67 (1H, s); m/z (ES+) 600 (M$^+$+H, 100%)

EXAMPLE 8

8-[(2R,3S,4S)-2-[(1R)-1-(3,5-Bis(trifluoromethyl)phenyl)ethoxy]-3-phenyl(tetrahydropyran-4-yl)]methyl-2,2-dimethyl-1-oxa-8-aza-spiro[4.5]decane A mixture of (2R,3S,4S)-2-[(1R)-1-(3,5-bis(trifluoromethyl)phenyl)ethoxy]-3-phenyl(tetrahydropyran)-4-aldehyde (see Example 43 in WO 00/56727) and 2,2-dimethyl-1-oxa-8-aza-spiro[4.5]decane (Description 18) was reacted and purified according to the procedure described in Example 6 to give the title compound.

$^1$H NMR (360 MHz, CDCl$_3$): δ 1.20 (6H, s), 1.44 (3H, d, J 6.6 Hz), 1.46-1.55 (4H, m), 1.60-1.71 (1H, m), 1.72-1.82 (4H, m), 1.82-1.95 (1H, m), 1.95-2.18 (3H, m), 2.25-2.38 (2H, m), 2.50-2.65 (3H, m), 3.73-3.75 (1H, m), 3.97-4.04 (1H, m), 4.41 (1H, d, 2.3 Hz), 4.87 (1H, q, J 6.6 Hz), 7.18 (2H, s) 7.18-7.32 (5H, m), 7.58 (1H, s); m/z (ES+) 600 (M$^+$+H, 100%)

EXAMPLE 9

8-[(2R,3S,4S)-2-[(1R)-1-(3,5-Bis(trifluoromethyl)
phenyl)ethoxy]-3-phenyl-tetrahydropyran-4-yl]me-
thyl-1-oxa-8-aza-spiro[4.5]decane A mixture of (2R,3S,4S)-2-[(1R)-1-(3,5-bis(trifluoromethyl)phenyl)ethoxy]-3-phenyl(tetrahydropyran)-4-aldehyde (see Example 43 in WO 00/56727) and 1-oxa-8-aza-spiro[4.5]decane (Description 17) was reacted and purified according to the procedure described in Example 6 to give the title compound.

$^1$H NMR (360 MHz, CDCl$_3$): δ 1.45 (3H, d, J 6.6 Hz), 1.46-1.70 (7H, m), 1.86-2.32 (7H, m), 2.40-2.75 (4H, m), 3.73-3.78 (3H, m), 4.04-4.10 (1H, m), 4.41 (1H, d, 3.0 Hz), 4.95 (1H, q, J 6.6 Hz), 7.18-7.29 (5H, m) 7.35 (2H, s), 7.67 (1H, s); m/z (ES+) 572 (M$^+$+H, 100%).

EXAMPLE 10

8-[(2R,3S,4S)-2-[(1R)-1-(3,5-Bis(trifluoromethyl)
phenyl)ethoxy]-3-phenyl-tetrahydropyran-4-yl]me-
thyl-2-oxa-8-aza-spiro[4.5]decane A mixture of (2R,3S,4S)-2-[(1R)-3,5-bis(trifluoromethyl)phenyl)ethoxy]-3-phenyl(tetrahydropyran)-4-aldehyde (see Example 43 in WO 00/56727) and 2-oxa-8-aza-spiro[4.5]decane (*Bioorg. and Med. Chem. Lett.* 2002, 12, 1759) was reacted and purified according to the procedure described in Example 6 to give the title compound.

$^1$H NMR (360 MHz, CDCl$_3$): δ 1.45 (3H, d, J 6.6 Hz), 1.48-1.70 (5H, m), 1.66 (2H, t, J 7.1 Hz), 1.86-1.98 (1H, m), 2.01-2.20 (4H, m), 2.36-2.48 (2H, m), 2.56 (1H, dd, J 11.9, 3.0 Hz), 2.58-2.70 (1H, m), 3.48 (2H, s), 3.75 (1H, dd, J 11.1, 3.7 Hz), 3.81 (2H, t, J 7.1 Hz), 3.97-4.04 (1H, m), 4.42 (1H, d, J 3.0 Hz), 4.87 (1H, q, J 6.6 Hz), 7.18 (2H, s), 7.19-7.29 (5H, m), 7.59 (1H, s); m/z (ES+) 572 (M$^+$+H, 100%).

EXAMPLE 11

8-[(2R,3R,4R)-2-[(1R)-1-(3,5-Bis(trifluoromethyl)
phenyl)ethoxy]-3-phenyl-tetrahydropyran-4-yl]me-
thyl-2-oxa-8-aza-spiro[4.5]decane A mixture of (2R,3R,4R)-2-[(1R)-1-(3,5-bis(trifluoromethyl)phenyl)ethoxy]-3-phenyl(tetrahydropyran)-4-aldehyde (see Example 45 in WO 00/56727) and 2-oxa-8-aza-spiro[4.5]decane (*Bioorg. and Med. Chem. Lett.* 2002, 12, 1759) was reacted and purified according to the procedure described in Example 6 to give the title compound.

$^1$H NMR (360 MHz, CDCl$_3$): δ 1.35 (3H, d, J 6.6 Hz), 1.40-1.50 (3H, m), 1.60 (2H, t, J 7.1 Hz), 1.85-2.05 (6H, m), 2.20-2.42 (3H, m), 3.42 (2H, s), 3.52 (1H, multiplet centre (mc)), 3.77 (2H, t, J 7.1 Hz), 4.10-4.16 (1H, m), 4.18 (1H, d, J 8.0 Hz), 4.94 (1H, q, J 6.6 Hz), 6.99-7.01 (2H, s), 7.16 (2H, s), 7.21-7.25 (3H, m), 7.65 (1H, s); m/z (ES+) 572 (M$^+$+H, 100%).

EXAMPLE 12

8-[(2R,3R,4R)-2-[(1R)-1-(3,5-Bis(trifluoromethyl)
phenyl)ethoxy]-3-phenyl-tetrahydropyran-4-yl]me-
thyl-2,2-dimethyl-1-oxa-8-aza-spiro[4.5]decane A mixture of (2R,3R,4R)-2-[(1R)-1-(3,5-bis(trifluoromethyl)phenyl)ethoxy]-3-phenyl(tetrahydropyran)-4-aldehyde (see Example 45 in WO 00/56727) and 2,2-dimethyl-1-oxa-8-aza-spiro[4.5]decane (Description 18) was reacted and purified according to the procedure described in Example 6 to give the title compound.

$^1$H NMR (360 MHz, CDCl$_3$): δ 1.16 (6H, s), 1.35 (3H, d, J 6.6 Hz), 1.38-1.61 (5H, m), 1.71 (4H, br s), 1.86-2.02 (5H, m), 2.15-2.22 (2H, m), 2.31-2.48 (2H, m), 3.50 (1H, br t), 4.08-4.15 (1H, m), 4.17 (1H, d, J 8.3 Hz), 4.93 (1H, q, J 6.6 Hz), 6.98-7.00 (2H, m), 7.16 (2H, s) 7.20 (3H, br s), 7.65 (1H, s); m/z (ES+) 600 (M$^+$+H, 100%).

EXAMPLE 13

8-[(2R,3R,4R)-2-[(1R)-1-(3,5-Bis(trifluoromethyl)
phenyl)ethoxy]-3-phenyl-tetrahydropyran-4-yl]me-
thyl-1-oxa-3-aza-spiro[4.5]decane A mixture of (2R,3R,4R)-2-[(1R)-1-(3,5-bis(trifluoromethyl)phenyl)ethoxy]-3-phenyl(tetrahydropyran)-4-aldehyde (see Example 45 in WO 00/56727) and 1-oxa-8-aza-spiro[4.5]decane (Description 17) was reacted and purified according to the procedure described in Example 6 to give the title compound.

$^1$H NMR (360 MHz, CDCl$_3$): δ 1.35 (3H, d, J 6.6 Hz), 1.46-1.66 (8H, m), 1.84 (2H, qn), 1.90-2.32 (6H, m), 2.37 (2H, t, J 7.1 Hz), 3.53 (1H, br t), 3.73 (2H, t, J 7.1 Hz), 4.13 (1H, dd, J 11.7, 3.4 Hz), 4.18 (1H, d, 8.2 Hz), 4.94 (1H, q, J 6.6 Hz), 6.96-7.01 (2H, m), 7.16 (2H, s), 7.21 (3H, br s), 7.65 (1H, s); m/z (ES+) 572 (M$^+$+H, 100%)

EXAMPLE 14

8-[(2R,3R,4R)-2-[(1R)-1-(3,5-Bis(trifluoromethyl)
phenyl)ethoxy]-3-phenyl-tetrahydropyran-4-yl]me-
thyl-1,1-dimethyl-2-oxa-8-aza-spiro[4.5]decane A mixture of (2R,3R,4R)-2-[(1R)-1-(3,5-bis(trifluoromethyl)phenyl)ethoxy]-3-phenyl(tetrahydropyran)-4-aldehyde (see Example 45 in WO 00/56727) and 1,1-dimethyl-2-oxa-8-aza-spiro[4.5]decane (*Bioorg. and Med. Chem. Lett.* 2002, 12, 1759) was reacted and purified according to the procedure described in Example 6 to give the title product.

$^1$H NMR (360 MHz, CDCl$_3$): δ 1.03 (6H, s), 1.15-1.28 (2H, m), 1.35 (3H, d, J 6.6 Hz), 1.38-1.49 (2H, m), 1.50-1.59 (3H, m), 1.74 (2H, t, J 7.1 Hz), 1.86-2.05 (4H, m), 2.38 (1H, br t), 2.51-2.58 (1H, m), 2.61-2.68 (1H, m), 3.52 (1H, br t), 3.73 (2H, t, J 7.1 Hz), 4.13-4.19 (2H, m), 4.93 (1H, q, J 6.6 Hz), 6.98-7.01 (2H, m), 7.16 (2H, s) 7.22 (3H, br s), 7.65 (1H, s); m/z (ES+) 600 (M$^+$+H, 100%).

EXAMPLE 15

8-[(2R,3R,4R)-2-[(1R)-1-(3,5-Bis(trifluoromethyl)
phenyl)ethoxy]-3-(4-fluorophenyl)-tetrahydropyran-
4-yl]methyl-2-oxa-8-aza-spiro[4.5]decan-4-one Dess-Martin periodinane (0.6 g, 1.4 mmol) was added to a solution of (4S)-8-[(2R,3R,4R)-2-[(1R)-1-(3,5-bis(trifluoromethyl)phenyl)ethoxy]-3-(4-fluorophenyl)-tetrahydropyran-4-yl]methyl-2-oxa-8-aza-spiro[4.5]decan-4-ol (Example 3; 0.85 g, 1.4 mmol) in dichloromethane (20 ml). The mixture was stirred at room temperature for 4 hours then quenched by addition of saturated sodium hydrogen carbonate. After 30 minutes the mixture was partitioned between water and dichloromethane. The organic extracts were dried and concentrated. The residue was chromatographed on silica gel eluting with 2% methanol/dichloromethane to give the title compound (510 mg, 60%).

$^1$H NMR (400 MHz, CDCl$_3$): δ 7.67 (1H, s), 7.17 (2H, s), 6.99-6.91 (4H, m), 4.96 (1H, q, J 6.5 Hz), 4.15-4.10 (2H, m), 3.96-3.90 (4H, m), 3.50 (1H, dt, J 2, 12.1 Hz), 2.64-2.62 (1H, m), 2.52-2.49 (1H, m), 2.38 (1H, dd, J 8.4, 10.9 Hz), 2.02-1.87 (5H, m), 1.76-1.66 (3H, m), 1.45-1.39 (3H, m), 1.37 (3H, d, J 6.6 Hz).

EXAMPLE 16

(4RS)-8-[(2R,3R,4R)-2-[(1R)-1-(3,5-Bis(trifluoromethyl)phenyl)ethoxy]-3-(4-fluorophenyl)-tetrahydropyran-4-yl]methyl-2-oxa-4-methyl-8-aza-spiro[4.5]decan-4-ol Methyl magnesium chloride (3.0M solution in tetrahydrofuran, 90 μl) was added to a solution of 8-[(2R,3R,4R)-2-((1R)-1-(3,5-bis(trifluoromethyl)phenyl)ethoxy]-3-(4-fluorophenyl)tetrahydropyran-4-yl]methyl-2-oxa-8-aza-spiro[4.5]decan-4-one (Example 15; 100 mg, 0.16 mmol) stirring in tetrahydrofuran (2 ml) at room temperature. After 2 hours the reaction was quenched by addition of saturated ammonium chloride. The mixture was partitioned between ethyl acetate and water. The organic extracts were separated, dried and concentrated. The residue was chromatographed on silica gel eluting with dichloromethane/methanol/ammonia mixtures to give the title compound (66 mg, 65%).

$^1$H NMR (400 MHz, CDCl$_3$): δ 7.67 (1H, s), 7.17 (2H, s), 7.03-6.89 (4H, m), 4.95 (1H, q, J 6.6 Hz), 4.13 (2H, m), 3.82 (1H, dd, J 5.9, 8.5 Hz), 3.68-3.61 (3H, m), 3.54-3.51 (1H, m), 2.69-2.53 (2H, m), 2.39 (1H, td, J 2.9, 10.9 Hz), 2.01-1.88 (5H, m), 1.62-1.41 (5H, m), 1.37 (3H, d, J 6.6 Hz), 1.36-1.35 (1H, m), 1.15 (3H, s); m/z (ES+) 620 (M+H)$^+$.

EXAMPLE 17

(4RS)-8-[(2R,3R,4R)-2-[(1R)-1-(3,5-Bis(trifluoromethyl)phenyl)ethoxy]-(4-fluorophenyl)tetrahydropyran-4-yl]methyl-2-oxa-4-ethynyl-8-aza-spiro[4.5]decan-4-ol Ethynyl magnesium bromide (0.5M solution in tetrahydrofuran, 0.5 mL) was added to a solution of 8-[(2R,3R,4R)-2-[(1R)-1-(3,5-bis(trifluoromethyl)phenyl)ethoxy]-3-(4-fluorophenyl)-tetrahydropyran-4-yl]methyl-2-oxa-8-aza-spiro[4.5]decan-4-one (Example 15) (100 mg, 0.16 mmol) stirring in tetrahydrofuran (2 ml) at room temp. After 2 hours the reaction was quenched by addition of saturated ammonium chloride. The mixture was partitioned between ethyl acetate and water. The organic extracts were separated, dried, and concentrated. The residue was purified by chromatography on silica gel eluting with dichloromethane/methanol/ammonia mixtures to give the title compound (51 mg, 49%).

$^1$H NMR (400 MHz, CDCl$_3$): δ 7.67 (1H, s), 7.26 (2H, s), 7.17-6.90 (4H, m), 4.95 (1H, q, J 6.6 Hz), 4.15-4.10 (2H, m), 3.97-3.95 (1H, m), 3.90-3.84 (2H, m), 3.62-3.48 (2H, m), 2.69-2.57 (3H, m), 2.45-2.36 (1H, m), 2.08-1.39 (11H, m), 1.37 (3H, d, J 6.6 Hz); m/z (ES+) 630 (M+H)$^+$.

EXAMPLE 18

(8S)-2-[((2R,3R,4R)-2-[(1R)-1-[3,5-Bis(trifluoromethyl)phenyl]ethoxy]-3-phenyl)-tetrahydro-2H-pyran-4-yl)methyl]-6-oxa-2-azaspiro[3.4]octan-8-ol (2R,3R,4R)-2-[(1R)-1-[3,5-Bis(trifluoromethyl)phenyl]ethoxy]-3-phenyltetrahydro-2H-pyran-4-carbaldehyde (WO 00/56727) (760 mg, 1.7 mmol) and 6-oxa-2-azaspiro[3.4]octan-8-ol (Description 19) (214 mg, 1.7 mmol) were dissolved in 1,2-dichloroethane (20 mL) and sodium triacetoxyborohydride (636 mg, 3 mmol) was added. The suspension formed was stirred at ambient temperature for 16 hrs then quenched with 1N sodium hydroxide solution (50 mL). The biphasic mixture formed was extracted with dichloromethane (2×50 mL), and the extracts were dried (MgSO$_4$) then concentrated to give a gum. The residue was purified by silica chromatography to give a mixture of the two diastereomers, which could be separated by chiral HPLC (Cyclobond II, 7.5% EtOH/hexane) to give isomer A (for isomer B, see Example 19): Isomer A: $^1$H NMR (400 MHz, CDCl$_3$): δ 7.65 (1H, s), 7.24-7.21 (3H, m), 7.15 (2H, s), 7.03-6.99 (2H, m), 4.93 (1H, q, J 6.6 Hz), 4.21 (1H, dd, J 2.9, 4.6 Hz), 4.17 (1H, d, J 8.4 Hz), 4.12 (1H, ddd, J 1.7, 4.6, 11.7 Hz) 3.84 (1H, dd, J 4.6, 9.9 Hz), 3.76 (2H, s), 3.62 (1H, dd, J 2.8, 9.0 Hz), 3.50 (1H, dt, J 2.4, 12.3 Hz), 3.37 (1H, d, J 7.4 Hz), 3.03 (1H, d, J 6.9 Hz), 2.80 (2H, dd, J 7.4, 14.8 Hz), 2.41 (1H, dd J 8.0, 11.3 Hz), 2.16 (1H, dd, J 9.5, 12.3 Hz), 2.07 (1H, dd, J 3.3, 11.8 Hz) 1.85-1.75 (2H, m), 1.63 (1H, br m), 1.52-1.41 (1H, m), 1.35 (3H, d, J 6.6 Hz); m/z (ES$^+$) 560 (M+H).

EXAMPLE 19

(8R)-2-[((2R,3R,4R)-2-[(1R)-1-[3,5-bis(trifluoromethyl)phenyl]ethoxy]-3-phenyltetrahydro-2H-pyran-4-yl)methyl]-6-oxa-2-azaspiro[3.4]octan-8-ol This product was the second peak to elute from the prep HPLC run described in Example 18.

Isomer B: $^1$H NMR (360 MHz, CDCl$_3$): δ 7.65 (1H, s), 7.27-7.12 (5H, m), 7.01-6.99 (2H, m), 4.93 (1H q, J 6.6 Hz), 4.23 (1H, dd, J 3.2, 5.3 Hz), 4.17 (1H, dd, J 9.3 Hz), 4.12 (1H, ddd, J 2.0, 7.3, 11.8 Hz), 3.84 (1H, dd, J 4.6, 9.8 Hz), 3.75 (2H, s), 3.61 (1H, dd, J 3.1, 9.8 Hz), 3.50 (1H, dt, J 2.4, 12.3 Hz), 3.42 (1H, d, J 7.3 Hz), 3.04 (1H, d, J 6.8 Hz), 2.87 (1H, d, J 6.8 Hz), 2.72 (1H, d, J 6.8 Hz), 2.41 (1H, dd, J 8.5, 11 Hz), 2.17 (1H, dd, J 9.2, 12.0 Hz), 2.07 (1H, dd, J 3.6, 12.6 Hz), 1.86-1.76 (3H, m), 1.52-1.41 (1H, m), 1.35 (3H, d, J 6.6 Hz); m/z (ES$^+$) 560 (M+H).

EXAMPLE 20

(4RS)-8-[(2R,3R,4R)-2-[(1R)-1-(3,5-Bis(trifluoromethyl)phenyl)ethoxy]-3-phenyl-tetrahydropyran-4-yl]methyl-1-oxa-8-azaspiro[4.5]decan-4-ol This product was prepared according to the procedure described in Example 2 using (2R,3R,4R)-2-[(1R)-1-(3,5-bis(trifluoromethyl)phenyl)ethoxy]-3-phenyl-tetrahydropyran-4-carbaldehyde (WO 0056727) and 4-hydroxy-1-oxa-8-azaspiro[4.5]decane (Description 20).

$^1$H NMR (500 MHz, CDCl$_3$): δ 1.35 (3H, d, J 6.6 Hz), 1.38-1.55 (2H, m), 1.6-1.98 (4H, m), 2.00-2.25 (4H, m), 2.38 (1H, dd, J 11.2, 8.4 Hz), 2.39-2.7 (2H, m), 3.53 (1H, t, J 12.0 Hz), 3.72-3.76 (1H, m), 3.89 (1H, multiplet centre (mc)), 4.13 (1H, dd, J 11.8, 3.4 Hz), 4.20 (1H, d, J 8.3 Hz), 4.94 (1H, q, J 6.5 Hz), 6.99-7.00 (2H, m), 7.16 (2H, s), 7.21-7.22 (3H, m), 7.65 (1H, s); m/z (ES$^+$) 588 (M$^+$+1, 100%).

EXAMPLE 21

(4RS)-8-[(2R,3R,4R)-2-[(1R)-1-(3,5-Bis(trifluoromethyl)phenyl)ethoxy]-3-(4-fluorophenyl)-tetrahydropyran-4-yl]methyl-3,3-dimethyl-2-oxa-8-azaspiro[4.5]decan-4-ol This product was prepared according to the procedure described in Example 6 using (2R,3R,4R)-2-[(1R)-1-(3,5-bis (trifluoromethyl)phenyl)ethoxy]-3-(4-fluorophenyl)-tetrahydropyran-4-carbaldehyde (Description 11) and 4-hydroxy-3,3-dimethyl-2-oxa-8-azaspiro[4.5]decane (Description 21).

$^1$H NMR (400 MHz, MeOD): δ 1.12 (3H, s), 1.24 (3H, s), 1.36 (3H, d, J 6.6 Hz), 1.39-1.44 (2H, m), 1.56-1.78 (4H, m), 1.82-2.06 (4H, m), 2.37 (1H, t, J 9.1 Hz), 2.39-2.56 (2H, m), 3.44 (1H, s), 3.45-3.58 (3H, m), 4.10-4.14 (2H, m), 4.95 (1H, q, J 6.6 Hz), 6.91-6.99 (4H, m), 7.17 (1H, s), 7.67 (1H, s); m/z (ES$^+$) 634 (M$^+$+1, 100%).

EXAMPLE 22

(4R*)-8-[(2R,3R,4R)-2-[(1R)-1-(3,5-Bis(trifluoromethyl)phenyl)ethoxy]-3-(4-fluorophenyl)-tetrahydropyran-4-yl]methyl-1-oxa-3-spiro[4.5]decan-4-ol This compound was prepared from the reaction of the compounds of Description 11 and 20 following the procedure described in Example 6. The product was purified by chromatography on silica to give a mixture of two diastereomers, which were separated by chiral HPLC (Cyclobond II, 7.5% EtOH/hexane) to give isomer A:

$^1$H NMR (500 MHz, CDCl$_3$): δ 7.67 (1H, s), 7.17 (2H, s), 6.98-6.90 (4H, m), 4.95 (1H, q, J 6.4 Hz), 4.12 (2H, dd, J 2.1, 8.3 Hz), 3.93-3.89 (2H, m), 3.78-3.74 (1H, m), 3.52 (1H, dd, J 12.1, 12.1 Hz), 2.38 (2H, t, J 8.7 Hz), 2.29-2.19 (3H, m), 2.01 (2H, m), 1.93 (2H, m), 1.85 (1H, m), 1.71 (1H, m), 1.41 (3H, s), 1.36 (3H, d, J 6.6 Hz); m/z (ES+) 606.

EXAMPLE 23

(4S*)-8-[(2R,3R,4R)-2-[(1R)-1-(3,5-Bis(trifluoromethyl)phenyl)ethoxy]-3-(4-fluorophenyl)-tetrahydropyran-4-yl]methyl-1-oxa-8-azaspiro[4.5]decan-4-ol This compound was prepared from the reaction of the compounds of Description 11 and 20 following the procedure described in Example 6. The product was purified by chromatography on silica to give a mixture of two isomers, which were separated by chiral HPLC (Chiralpak AD, 2% EtOH in hexane) to give isomer A (see Example 22) and isomer B:

$^1$H NMR (500 MHz, CDCl$_3$): δ 7.67 (1H, s), 7.17 (2H, s), 6.98-6.90 (4H, m), 4.97-4.93 (1H, q, J 6.6 Hz), 4.12 (2H, dd, J 2.6, 8.4 Hz), 3.93-3.87 (2H, m), 3.79-3.73 (1H, m), 3.51 (1H, dd, J 10, 10 Hz), 2.47 (1H, m), 2.38 (1H, t, J 9.6 Hz), 2.26-2.19 (3H, m), 2.03-1.93 (5H, m), 1.88-1.82 (1H, m), 1.40-1.34 (6H, m); m/z (ES+) 606.

EXAMPLE 24

(4R)-8-[((2R,3R,4R)-2-{(1R)-1-[3,5-Bis(trifluoromethyl)phenyl]ethoxy}-3-phenyltetrahydro-2H-pyran-4-yl)methyl]-4-methoxy-2-oxa-3-azaspiro[4.5]decane To a solution of (4R)-8-[((2R,3R,4R)-2-{(1R)-1-[3,5-bis (trifluoromethyl)phenyl]ethoxy-3-phenyltetrahydro-2H-pyran-4-yl)methyl-2-oxa-8-azaspiro[4.5]decan-4-ol (Example 2) (100 mg, 0.17 mmol) in anhydrous DMF (1 mL) was added a 60% dispersion of sodium hydride in mineral oil (40 mg) under ice cooling. After 15 min of stirring at 0° C. methyl iodide (31 mg) was added and the mixture was stirred at r.t. for 18 h, before it was diluted with water and extracted with ethyl acetate. The combined organic phases were washed with brine, dried over magnesium sulfate, filtered and concentrated in vacuo to give the crude product as colourless oil, which was then purified by flash chromatography on silica using 3-5% methanol in dichloromethane as eluant. The desired product was obtained as colourless viscous oil (76%).

$^1$H NMR (360 MHz, CDCl$_3$): δ 7.65 (1H, s), 7.22 (3H, m), 7.16 (2H, s), 7.01 (2H, m), 4.94 (1H, q, J 6.6 Hz), 4.18 (1H, d, J 8.4 Hz), 4.13 (1H, dd, J 3.3, 15 Hz), 3.90 (1H, dd, J 4.4, 9.8 Hz), 3.77 (1H, dd, J 2.0, 9.9 Hz), 3.56-3.48 (3H, m), 3.38-3.34 (1H, m), 3.25 (3H, s), 2.41-2.35 (2H, m), 2.19-2.06 (2H, m), 2.06-1.87 (7H, m), 1.79-1.73 (1H, m), 1.47-1.39 (4H, m), 1.35 (3H, d, J 6.6 Hz); m/z (ES+) 602.

EXAMPLE 25

(4R)-8-[((2R,3R,4R)-2-{(1R)-1-[3,5-Bis(trifluoromethyl)phenyl]ethoxy}-3-(4-fluorophenyl)tetrahydro-2-H-pyran-4-yl)methyl]-4-methoxy-2-oxa-8-azaspiro[4.5]decane This compound was prepared from the compound of Example 4 following the procedure described in Example 24.

$^1$H NMR (360 MHz, CDCl$_3$): δ 7.67 (1H, s), 7.17 (2H, s), 7.00-6.92 (4H, m), 4.95 (1H, q, J 6.6 Hz), 4.16-4.09 (2H, m), 3.90 (1H, dd, J 4.4, 9.9 Hz), 3.77 (1H, dd, J 2.1, 9.9 Hz), 3.56-3.48 (3H, m), 3.37 (1H, dd, J 2.1, 4.3 Hz), 3.26 (3H, s), 2.41-2.33 (2H, m), 2.16-2.07 (2H, m), 2.02-1.84 (5H, m), 1.79-1.71 (1H, m), 1.49-1.39 (2H, m), 1.36 (3H, d, J 6.6 Hz); m/z (ES+) 620, 362.

EXAMPLE 26

8-[((2R,3R,4R)-2-{(1R)-1-[3,5-Bis(trifluoromethyl)phenyl]ethoxy}-3-phenyltetrahydro-2H-pyran-4-yl) methyl]-1-oxa-3-azaspiro[4.5]decan-3-ol To a solution of (2R,3R,4R)-2-{(1R)-1-[3,5-bis(trifluoromethyl)phenyl]ethoxy}-3-phenyltetrahydro-2H-pyran-4-carbaldehyde (WO 00/56727) (0.97 g, 2.71 mmol) and triethylamine (0.72 mL, 5.17 mmol) in 1,2-dichloroethane (15 mL) was added 1-oxa-8-aza[4.5]decan-3-ol trifluoroacetate (Description 22) (775 mg), followed by sodium triacetoxyborohydride (630 mg, 3 mmol). The reaction mixture was stirred for 2 h at room temperature, then treated with dilute sodium hydroxide solution and extracted with dichloromethane. The combined organic phases were washed with brine, dried over magnesium sulfate, filtered and concentrated to give the crude product as a light brown oil. Flash chromatography on a column of silica gel with a gradient solvent system of 5-10% methanol in dichloromethane afforded the title compound as a mixture of epimers (53%, 0.85 g).

¹H NMR (360 MHz, CDCl₃): δ 7.66 (1H, s), 7.22 (3H, s), 7.16 (2H, s), 7.00 (2H, m), 4.94 (1H, q, J 6.6 Hz), 4.43 (1H, br s), 4.20 (1H, d, J 8.2 Hz), 4.13 (1H, dd, J 3.3, 11.9 Hz), 3.82 (1H, dd, J 4.2, 9.9 Hz), 3.72 (1H, d, J 10.1 Hz), 3.54 (1H, dd, J 12, 12 Hz), 2.59-1.41 (ca. 20H, methylene envelope), 1.24 (3H, d, J 6.6 Hz); m/z (ES+) 588.

EXAMPLE 27

8-[((2R,3R,4R)-2-{(1R)-1-[3,5-Bis(trifluoromethyl) phenyl]ethoxy}-3-phenyltetrahydro-2H-pyran-4-yl) methyl]-1-oxa-8-azaspiro[4.5]decan-3-one This compound was prepared from the compound of Example 26 following the procedure described in Example 15.

¹H NMR (360 MHz, CDCl₃): δ 7.65 (1H, s), 7.23-7.19 (3H, m), 7.17 (2H, s), 7.09-6.97 (2H, m), 4.94 (1H, q, J 6.5 Hz), 4.18 (1H, d, J 8.3 Hz), 4.13 (1H, dd, J 4.2, 11.7 Hz), 3.92 (2H, s), 3.53 (1H, t, J 11.1 Hz), 2.49-2.42 (1H, m), 2.39 (1H, dd, J 8.4, 10.8 Hz), 2.31-2.17 (2H, m), 2.05 (2H, dd, J 10.2, 12.6 Hz), 2.00-1.93 (3H, m), 1.76-1.68 (2H, m), 1.67-1.58 (2H, m), 1.48-1.38 (1H, m), 1.36 (3H, d, J 6.6 Hz); m/z (ES+) 586.

EXAMPLE 28

(2R or S,5R or S)-5-((2R,3R,4R)-{(1R)-1-[3,5-Bis (trifluoromethyl)phenyl]-ethoxy}tetrahydro-3-phenyl-2H-pyran-4-yl)tetrahydro-N-(phenylmethyl)-2-furanmethanamine A solution of (2RS,5R or S)-5-((2R,3R,4R)-{(1R)-1-[3,5-bis(trifluoromethyl)phenyl]-ethoxy}tetrahydro-3-phenyl-2H-pyran-4-yl)-1,2,5-pentanetriol 1-(4-methylbenzenesulfonate) 5-methanesulfonate (3:1 mixture of alcohol diastereoisomers; Description 27; 0.48 g, 0.63 mmol) and benzenemethanamine (0.69 mL, 6.3 mmol) in methanol (10 mL) was placed in a sealed tube and heated in a microwave oven at 140° C. for 10 minutes. The mixture was cooled and the solvent was evaporated under reduced pressure. The residue was dissolved in ethyl acetate (20 mL), washed with saturated aqueous potassium carbonate (20 mL) and brine (20 mL), dried (Na₂SO₄), and the solvent was evaporated under reduced pressure. The residue was purified by preparative thin layer chromatography on silica gel, eluting with EtOAc/MeOH/NH₃(Aq.) (98:2:0.2), to give the title compound (single diastereoisomer) as a colorless oil (0.12 g, 31%).

¹H NMR (500 MHz, CD₃OD) δ 7.71 (1H, s), 7.31-7.06 (12H, m), 4.99 (1H, q, J 6.5 Hz), 4.34 (1H, d, J 8.5 Hz), 4.10 (1H, m), 3.94 (1H, m), 3.63 (3H, m), 3.53 (1H, m), 2.41 (3H, m), 2.29 (1H, m), 1.92 (1H, m), 1.71 (3H, m), 1.51 (1H, m), 1.36 (1H, m), 1.32 (3H, d, J 6.6 Hz); m/z (ES⁺) 608 (M+1).

EXAMPLE 29

(2S or R,5R or S)-5-((2R,3R,4R)-{(1R)-1-[3,5-Bis (trifluoromethyl)phenyl]-ethoxy}tetrahydro-3-phenyl-2H-pyran-4-yl)tetrahydro-N-(phenylmethyl)-2-furanmethanamine The title compound (single diastereoisomer) was prepared from (2RS,5R or S)-5-((2R,3R,4R)-{(1R)-1-[3,5-bis(trifluoromethyl)phenyl]ethoxy}tetrahydro-3-phenyl-2H-pyran-4-yl)-1,2,5-pentanetriol 1-(4-methylbenzenesulfonate) 5-methanesulfonate (1:3 mixture of alcohol diastereoisomers; Description 28) according to the method of Example 28.

¹H NMR (500 MHz, CD₃OD): δ 7.71 (1H, s), 7.31-7.06 (12H, m), 4.99 (1H, q, J 6.5 Hz), 4.34 (1H, d, J 8.5 Hz), 4.10 (1H, m), 3.78 (1H, m), 3.63 (2H, ABX), 3.60 (1H, dt, J 2.0, 11.8 Hz), 3.45 (1H, m), 2.53 (1H, dd, J 3.7, 12.0 Hz), 2.46 (1H, dd, J 8.4, 12.0 Hz), 2.39 (1H, dd, J 8.3, 11.8 Hz), 2.27 (1H, m), 1.80 (1H, m), 1.65 (3H, m), 1.42 (2H, m), 1.32 (3H, d, J 6.6 Hz); m/z (ES⁺) 608 (M+1).

EXAMPLE 30

(2R or S,5R or S)-5-((2R,3R,4R)-{(1R)-1-[3,5-Bis (trifluoromethyl)phenyl]-ethoxy}tetrahydro-3-phenyl-2-pyran-4-yl)tetrahydro-2-furanmethanamine Dried palladium hydroxide on carbon (20 mg) was added to a solution of (2R or S,5R or S)-5-((2R,3R,4R)-{(1R)-1-[3,5-bis(trifluoromethyl)phenyl]ethoxy}-tetrahydro-3-phenyl-2H-pyran-4-yl)tetrahydro-N-(phenylmethyl)-2-furanmethanamine (Example 28; 0.12 g, 0.20 mmol) in ethanol (3 mL) and the mixture was stirred under hydrogen (1 Atmosphere) for 12 hours. The mixture was filtered through Celite™ and the solvent was evaporated under reduced pressure. The residue was purified by preparative thin layer chromatography on silica gel, eluting with EtOAc/MeOH/NH₃(Aq.) (90:10:1) then by preparative HPLC (Supelsosil™ ABZ+PLUS 100× 21.2 mm i.d.; gradient 0.1% TFA-H₂O/45% MeCN to 0.1% TFA-H₂O/55% MeCN over 10 min; 20 mL/min; 210 nm; 400 μl injections of a 20 mg/mL solution in MeCN), to give the title compound (single diastereoisomer) as a colorless oil (0.30 mg, 29%).

¹H NMR (500 MHz, CD₃OD) δ 7.71 (1H, s), 7.31 (2H, m), 7.17 (3H, m), 7.09 (2H, m), 4.99 (1H, q, J 6.5 Hz), 4.36 (1H, d, J 8.1 Hz), 4.14 (1H, m), 3.83 (1H, m), 3.63 (1H, dt, J 2.3, 11.0 Hz), 3.57 (1H, m), 2.53 (1H, m), 2.43 (2H, m), 2.32 (1H, m), 1.92 (1H, m), 1.73 (3H, m), 1.53 (1H, m), 1.40 (1H, m), 1.32 (3H, d, J 6.6 Hz); m/z (S⁺) 518 (M+1), 260 (M+1-C₁₀H₈F₆O).

EXAMPLE 31

(2S or R,5R or S)-5-((2R,3R,4R)-{(1R)-1-[3,5-Bis (trifluoromethyl)phenyl]-ethoxy}tetrahydro-3-phenyl-2H-pyran-4-yl)-N,N-diethyltetrahydro-2-furanmethanamine The title compound was prepared from (2S or R,5R or S)-5-((2R,3R,4R)-{(1R)-1-[3,5-bis(trifluoromethyl)phenyl] ethoxy}tetrahydro-3-phenyl-2H-pyran-4-yl)tetrahydro-N-(phenylmethyl)-2-furanmethanamine (Example 29) according to the method of Example 30.

¹H NMR (500 MHz, CD₃OD) δ 7.71 (1H, s), 7.31 (2H, s), 7.17 (3H, m), 7.09 (2H, m), 4.99 (1H, q, J 6.5 Hz), 4.36 (1H, d, J 8.1 Hz), 4.14 (1H, m), 3.63 (1H, m), 3.45 (1H, dt, J 2.3, 11.0 Hz), 3.30 (1H, m), 2.70-2.53 (5H, m), 2.41 (1H, dd, J 8.1, 12.0 Hz), 2.33 (1H, m), 1.88 (1H, m), 1.70 (3H, m), 1.53 (1H, m), 1.40 (1H, m), 1.32 (3H, d, J 6.6 Hz), 1.02 (6H, t, J 7.1 Hz); m/z (ES⁺) 574 (M+1).

EXAMPLE 32

(3R or S)-3-((2R,3R,4R)-{(1R)-1-[3,5-Bis(trifluoromethyl)phenyl]ethoxy}-tetrahydro-3-phenyl-2H-pyran-4-yl)thiomorpholine; and (3S or R)-3-((2R,3R,4R)-{(1R)-1-[3,5-bis(trifluoromethyl)phenyl]ethoxy}-tetrahydro-3-phenyl-2H-pyran-4-yl)thiomorpholine Methanesulfonyl chloride (0.12 mL, 0.17 g, 1.5 mmol) was added dropwise to a stirred, cooled (−10° C.) solution of (2R,3R,4R,αR or S)-α-{[(2-hydroxyethyl)thio]methyl}-2-{(1R)-1-[3,5-bis(trifluoromethyl)phenyl]ethoxy}-tetrahydro-3-phenyl-2H-pyran-4-methanol and (2R,3R,4R,αS or R)-α-{[(2-hydroxyethyl)thio]methyl}-2-{(1R)-1-[3,5-bis(trifluoromethyl)phenyl]ethoxy}-tetrahydro-3-phenyl-2H-pyran-4-methanol (Description 30, 1:1 mixture of diastereoisomers; 269 mg, 0.5 mmol) and triethylamine (0.28 mL, 0.20 g, 2 mmol) in dichloromethane (5 mL) and the mixture was stirred at −10° C. for 10 minutes. Water (20 mL) was added and the mixture was extracted with dichloromethane (3×20 mL). The combined organic fractions were washed with aqueous citric acid (10%, 2×20 mL), saturated aqueous sodium hydrogen carbonate/water (1:1, 2×20 mL) and brine (20 mL), dried (MgSO$_4$) and the solvent was evaporated under reduced pressure. The residue was dissolved in methanolic ammonia (7M, 5 mL), placed in a sealed tube and heated in a microwave oven at 60° C. for 10 minutes. The mixture was cooled and the solvent was evaporated under reduced pressure. The residue was purified by column chromatography on silica gel, eluting with CH$_2$Cl$_2$/MeOH/NH$_3$(aq.) (99:1:0.1 increasing to 96:4:0.4), to give the title compound (1:1 mixture of thiomorpholine epimers) as a colorless foam (81 mg, 31%).

$^1$H NMR (500 MHz, CD$_3$OD) δ 7.71, 7.70 (1H, each s), 7.32-7.12 (7H, m), 4.99 (1H, m), 4.39, 4.32 (1H, each d, J 8.4 Hz), 4.08 (1H, m), 3.58 (1H, m), 3.13-2.36 (8H, m), 2.08 (1H, m), 1.82-1.55 (2H, m), and 1.32, 1.31 (3H, each d, J 6.6 Hz); m/z (ES$^+$) 520 (M+1) and 262 (M+1-C$_{10}$H$_8$F$_6$O).

EXAMPLE 33

(2S)-2-((2R,3R,4R)-{(1R)-1-[3,5-Bis(trifluoromethyl)phenyl]ethoxy}-tetrahydro-3-phenyl-2H-pyran-4-yl)-1-methylazetidine (1R)-1-((2R,3R,4R)-{(1R)-1-[3,5-Bis(trifluoromethyl)phenyl]ethoxy}tetrahydro-3-phenyl-2H-pyran-4-yl)-1,3-propanediol dimethylsulfonate (Description 35; 0.25 g, 0.39 mmol) was dissolved in methylamine (2.0M in methanol, 4 mL) and heated at 140° C. for 10 minutes in a sealed tube in a Smith microwave reactor. The mixture was cooled and the solvent was evaporated under reduced pressure. Saturated aqueous potassium carbonate (50 mL) was added and the mixture was extracted with ethyl acetate (3×50 mL). The combined organic fractions were dried (MgSO$_4$) and the solvent was evaporated under reduced pressure. The residue was purified by preparative thin layer chromatography on silica gel, eluting with CH$_2$Cl$_2$/MeOH/NH$_3$(Aq.) (100:10:1), to give the title compound as a pale yellow solid (20 mg, 10%).

$^1$H NMR (500 MHz, CD$_3$OD) δ 1.31 (3H, d, J 6.6 Hz), 1.58 (1H, app dq,), 1.75 (1H, m), 1.81 (1H, m), 2.00 (1H, m), 2.10 (1H, m), 2.30 (1H, dd, J 8.2, 11.6 Hz), 2.59 (1H, q, J 9.4 Hz), 2.80 (1H, m), 3.22 (1H, m), 3.64 (1H, dd, J 9.7, 12.0 Hz), 4.14 (1H, m), 4.34 (1H, d, J 8.2 Hz), 4.99 (1H, q, J 6.6 Hz), 7.07-7.09 (2H, m), 7.19-7.24 (3H, m), 7.31 (2H, s), 7.71 (1H, s); m/z (ES$^+$) 488 (M+1) and 230 (M+1-C$_{10}$H$_8$F$_6$O).

EXAMPLE 34

(2R)-2-((2R,3R,4R)-{(1R)-1-[3,5-Bis(trifluoromethyl)phenyl]ethoxy}-tetrahydro-3-phenyl-2H-pyran-4-yl)-1-methylazetidine Prepared from (1S)-1-((2R,3R,4R)-{(1R)-1-[3,5-bis(trifluoromethyl)phenyl]-ethoxy}tetrahydro-3-phenyl-2H-pyran-4-yl)-1,3-propanediol dimethylsulfonate (Description 36) according to the method of Example 33.

$^1$H NMR (500 MHz, CD$_3$OD) δ 1.05 (1H, m), 1.14 (1H, m), 1.31 (3H, d, J 6.6 Hz), 1.42 (1H, m), 1.80 (1H, dd, J 4, 2 Hz), 2.12 (1H, m), 2.33 (3H, s), 2.36 (1H, m), 2.62 (1H, m), 2.93 (1H, m), 3.14 (1H, m), 3.63 (1H, dd, J 12.1, 2.1 Hz), 4.12 (1H, m), 4.42 (1H, d, J 8.5 Hz), 4.99 (1H, m), 7.05-7.06 (2H, m), 7.15-7.18 (3H, m), 7.32 (2H, app. s), 7.71 (1H, s); m/z (ES$^+$) 488 (M+1) and 230 (M+1-C$_{10}$H$_8$F$_6$O).

EXAMPLE 35

4-((2R,3R,4R)-{(1R)-1-[3,5-Bis(trifluoromethyl)phenyl]ethoxy}tetrahydro-3-phenyl-2H-pyran-4-yl)piperidin-4-ol 3-((2R,3R,4R)-{(1R)-1-[3,5-Bis(trifluoromethyl)phenyl]ethoxy}tetrahydro-3-phenyl-2H-pyran-4-yl)-1,3,5-propanetriol 1,5-dimethylsulfonate Description 40; 0.13 g, 0.19 mmol) was dissolved in methanolic ammonia (7M, 2 mL) and heated at 130° C. for 20 minutes in a sealed tube in a Smith microwave reactor. The mixture was cooled and the solvent was evaporated under reduced pressure. The residue was dissolved in water (25 mL) and basified with saturated aqueous potassium carbonate. The mixture was extracted with dichloromethane (3×30 mL). The combined organic fractions were dried (MgSO$_4$) and the solvent was evaporated under reduced pressure. The residue was purified by column chromatography on silica gel, eluting with CH$_2$Cl$_2$/MeOH/NH$_3$ (Aq.) (90:10:1), to give the title compound as a colorless oil (25 mg, 25%).

$^1$H NMR (500 MHz, CDCl$_3$) δ 7.65 (1H, s), 7.24-7.18 (3H, m), 7.16 (2H, s), 7.12 (2H, m), 4.90 (1H, q, J 6.6 Hz), 4.25 (1H, d, J 7.4 Hz), 4.16 (1H, br d, J 11 Hz), 3.54 (1H, br t, J 11 Hz), 2.84-2.79 (4H, m), 2.72 (1H, s), 2.02 (1H, br t, J 11 Hz), 1.8 (1H, br s), 1.78 (1H, br d, J 11 Hz), 1.64 (1H, br q, J 11 Hz), 1.56-1.51 (3H, m), 1.36 (3H, d, J 6.6 Hz), 1.31 (1H, m), 1.2 (1H, br s); m/z (ES$^+$) 518 (M+1) and 260 (M+1-C$_{10}$H$_8$F$_6$O).

EXAMPLE 36

4-((2R,3R,4R)-{(1R)-1-[3,5-Bis(trifluoromethyl)phenyl]ethoxy}tetrahydro-3-phenyl-2H-pyran-4-yl)-1-cyclopropylpiperidin-4-ol Prepared from 3-((2R,3R,4R)-{(1R)-1-[3,5-bis(trifluoromethyl)phenyl]ethoxy}-tetrahydro-3-phenyl-2H-pyran-4-yl)-1,3,5-propanetriol 1,5-dimethylsulfonate (Description 40) and cyclopropylamine according to the method of Example 33.

$^1$H NMR (500 MHz, CD$_3$OD) δ 7.69 (1H, s), 7.27 (2H, s), 7.16-7.10 (5H, m), 4.92 (1H, q, J 6.6 Hz), 4.25 (1H, d, J 8.1 Hz), 4.10 (1H, br d, J 12 Hz), 3.60 (1H, br t, J 12 Hz), 2.80 (1H, dd, J 11.1, 8.1 Hz), 2.65 (1H, m), 2.52-2.44 (2H, m), 2.34 (1H, m), 2.08 (1H, br t, J 12 Hz), 1.78 (1H, br d, J 12 Hz), 1.69 (1H, br q, J 12 Hz), 1.56 (1H, m), 1.45 (1H, m), 1.34 (1H, m), 1.32 (3H, d, J 6.6 Hz), 1.12 (2H, m), 0.41 (2H, m), 0.30 (2H, m); m/z (ES$^+$) 558 (M+1) and 300 (M+1-C$_{10}$H$_8$F$_6$O).

EXAMPLE 37

4-((2R,3R,4R)-{(1R)-1-[3,5-Bis(trifluoromethyl)phenyl]ethoxy}tetrahydro-3-phenyl-2H-pyran-4-yl)-1-(1-methylethyl)piperidin-4-ol Prepared from 3-((2R,3R,4R)-{(1R)-1-[3,5-bis(trifluoromethyl)phenyl]ethoxy}-tetrahydro-3-phenyl-2H-pyran-4-yl)-1,3,5-propanetriol 1,5-dimethylsulfonate (Description 40) and isopropylamine according to the method of Example 33.

$^1$H NMR (500 MHz, CD$_3$OD) δ 7.70 (1H, s), 7.27 (2H, s), 7.18-7.11 (5H, m), 4.93 (1H, q, J 6.6 Hz), 4.27 (1H, d, J 8.1 Hz), 4.11 (1H, br d, J 12 Hz), 3.61 (1H, br t, J 12 Hz), 2.86 (1H, m), 2.80 (1H, dd, J 11.1, 8.1 Hz), 2.76-2.55 (4H, m), 2.12 (1H, br t, J 12 Hz), 1.79 (1H, br d, J 12 Hz), 1.70 (1H, br q, J 12 Hz), 1.60 (1H, m), 1.47 (1H, m), 1.32 (3H, d, J 6.6 Hz), 1.24 (2H, m), 1.09 (3H, d, J 6.5 Hz), 1.08 (3H, d, J 6.5 Hz); m/z (ES$^+$) 560 (M+1).

EXAMPLE 38

(αR or S)-α-((2R,3R,4R)-{(1R)-1-[3,5-Bis(trifluoromethyl)phenyl]ethoxy}-tetrahydro-3-phenyl-2H-pyran-4-yl)-1-piperidineethanol Hydrochloride A mixture of (2R,3R,4R)-2-{(1R)-1-[3,5-bis(trifluoromethyl)phenyl]ethoxy}-tetrahydro-4-[(2R or S)-oxiranyl]-3-phenyl-2H-pyran (Description 41, Isomer A; 70 mg, 0.15 mmol) and piperidine (45 μL, 39 mg, 0.46 mmol) in methanol (5 mL) was placed in a sealed tube and heated in a microwave oven at 130° C. for 20 minutes. The mixture was cooled and the solvent was evaporated under reduced pressure. The residue was purified by column chromatography on silica gel, eluting with EtOAc then CH$_2$Cl$_2$/MeOH/NH$_3$(Aq.) (95:5:0.5), then by column chromatography on silica gel, eluting with CH$_2$Cl$_2$/MeOH (90:10) to give (αR or S)-α-((2R,3R,4R)-((1R)-1-[3,5-bis(trifluoromethyl)phenyl]ethoxy}tetrahydro-3-phenyl-2H-pyran-4-yl)-1-piperidineethanol as a solid (28 mg, 34%). The solid was dissolved in diethyl ether and ethereal hydrogen chloride (1M, 0.2 mL) was added. The solid was collected and dried in vacuo to give the title compound as a colorless solid.

$^1$H NMR (500 MHz, CDCl$_3$) δ 11.0 (1H, s), 7.66 (1H, s), 7.24 (3H, m), 7.18 (2H, s), 7.03 (2H, m), 4.95 (1H, q, J 6.6 Hz), 4.24 (1H, d, J 8.5 Hz), 4.17 (1H, br d, J 11 Hz), 3.76 (1H, br d, J 11 Hz), 3.50 (1H, br t, J 11 Hz), 3.43 (1H, br d, J 11 Hz), 3.31 (1H, br d, J 11 Hz), 2.94 (1H, br t, J 11 Hz), 2.87 (1H, dd, J 11.2, 8.5 Hz), 2.55 (1H, br q, J 11 Hz), 2.40-2.10 (4H, m), 1.95-1.05 (6H, m), 1.35 (3H, d, J 6.6 Hz), 1.32 (1H, m); m/z (ES$^+$) 546 (M+1) and 288 (M+1-C$_{10}$H$_8$F$_6$O).

EXAMPLE 39

(αS or R)-α-((2R,3R,4R)-{(1R)-1-[3,5-Bis(trifluoromethyl)phenyl]ethoxy}-tetrahydro-3-phenyl-2H-pyran-4-yl)-1-piperidineethanol Hydrochloride Prepared from (2R,3R,4R)-2-{(1R)-1-[3,5-bis(trifluoromethyl)phenyl]ethoxy}-tetrahydro-4-[(2S or R)-oxiranyl]-3-phenyl-2H-pyran (Description 41, Isomer B) and piperidine according to the method of Example 38.

$^1$H NMR (400 MHz, CDCl$_3$) δ 11.18 (1H, s), 7.65 (1H, s), 7.25 (3H, m), 7.12 (2H, s), 7.05 (2H, m), 4.92 (1H, q, J 6.6 Hz), 4.20 (1H, d, J 8.1 Hz), 4.18 (1H, br d, J 11 Hz), 3.85 (1H, br d, J 11 Hz), 3.55 (1H, br t, J 11 Hz), 3.40 (1H, br d, J 11 Hz), 3.06 (1H, br d, J 11 Hz), 2.76-2.58 (3H, m), 2.48 (1H, dd, J 12.2, 8.1 Hz), 2.29-1.45 (11H, m), 1.35 (3H, d, J 6.6 Hz); m/z (ES$^+$) 546 (M+1) and 288 (M+1-C$_{10}$H$_8$F$_6$O).

EXAMPLE 40

(αR or S,2R,3R,4R)-2-{(1R)-1-[3,5-Bis(trifluoromethyl)phenyl]ethoxy}-tetrahydro-α-[(dimethylamino)methyl]-3-phenyl-2H-pyran-4-methanol Hydrochloride Prepared from (2R,3R,4R)-2-{(1R)-1-[3,5-bis(trifluoromethyl)phenyl]ethoxy}-tetrahydro-4-[(2R or S)-oxiranyl]-3-phenyl-2H-pyran (Description 41, Isomer A) and dimethylamine according to the method of Example 38.

$^1$H NMR (500 MHz, CDCl$_3$) δ 11.3 (1H, br s), 7.66 (1H, s), 7.24-7.26 (3H, m), 7.19 (2H, s), 7.04-7.05 (2H, m), 4.96 (1H, q, J 6.6 Hz), 4.26 (1H, d, J 8.4 Hz), 4.18 (1H, dd, J 11.7, 3.3 Hz), 3.70 (1H, br d, J 9.7 Hz), 3.52 (1H, br t, J 11.8 Hz), 3.09 (1H, br t, J 12.1 Hz), 2.86 (1H, dd, J 11.0, 8.6 Hz), 2.64 (6H, br s), 2.43 (1H, br d, J 12.3 Hz), 1.89 (1H, m), 1.77 (1H, m), 1.60 (1H, br d, J 12.8 Hz), 1.36 (3H, d, J 6.6 Hz); m/z (ES$^+$) 506 (M+1) and 248 (M+1-C$_{10}$H$_8$F$_6$O).

EXAMPLE 41

1,1-Dimethylethyl(2R or S)-2-[(R or S)-((2R,3R,4R)-{(1R)-1-[3,5-Bis(trifluoromethyl)phenyl]ethoxy}tetrahydro-3-phenyl-2H-pyran-4-yl)hydroxymethyl]-1-pyrrolidinecarboxylate (Isomers A and B)

sec-Butyllithium (1.4M in hexanes, 1.6 mL, 2.24 mmol) was added slowly to a stirred, cooled (−78° C.) solution of 1,1-dimethylethyl 1-pyrrolidinecarboxylate (0.4 mL, 2.24 mmol) and N,N,N',N'-tetramethyl-1,2-ethanediamine (0.3 mL, 2.02 mmol) in diethyl ether (4.5 mL). The mixture was stirred at −78° C. for 3 hours, then (2R,3R,4R)-2-{(1R)-1-[3,5-bis(trifluoromethyl)phenyl]ethoxy}tetrahydro-3-phenyl-2H-pyran-4-carboxaldehyde (WO 00/56727A1; 0.5 g, 1.12 mmol) in diethyl ether (1 mL) was added dropwise. The mixture was stirred at −78° C. for 30 minutes, then warmed to room temperature. Water (2 mL) was added slowly, then ethyl acetate (10 mL). The layers were separated and the organic layer was washed with brine (5 mL). The combined aqueous layers were extracted with ethyl acetate (10 mL). The combined organic layers were dried (Na$_2$SO$_4$) and the solvent was evaporated under reduced pressure. The residue was purified by column chromatography on silica gel, eluting with hexane/EtOAc (85:15 increasing to 75:25), to give:

1,1-dimethylethyl(2R or S)-2-[(R or S)-((2R,3R,4R)-{(1R)-1-[3,5-bis(trifluoromethyl)phenyl]ethoxy}tetrahydro-3-phenyl-2H-pyran-4-yl)hydroxymethyl]-1-pyrrolidinecarboxylate (Isomer A; Single diastereoisomer; Stereochemistry unassigned) as a colorless oil (0.25 g, 36%); $^1$H NMR (500 MHz, CDCl$_3$) δ 7.67 (1H, s), 7.21 (5H, m), 7.20 (2H, s), 7.03 (2H, m), 4.95 (1H, q, J 6.5 Hz), 4.28 (1H, d, J 8.3 Hz), 4.20 (1H, m), 3.87 (1H, m), 3.53 (1H, dt, J 1.6, 10.8 Hz), 3.33 (2H, m), 3.11 (1H, m), 2.98 (1H, dd, J 8.3, 11.3 Hz), 2.92 (1H, m), 2.04 (1H, m), 1.75 (3H, m), 1.60 (1H, m), 1.44 (11H, m), 1.35 (3H, d, J 6.6 Hz); and 1,1-dimethylethyl(2R or S)-2-[(R or S)-((2R,3R,4R)-[(1R)-1-[3,5-bis(trifluoromethyl)phenyl]ethoxy]tetrahydro-3-phenyl-2H-pyran-4-yl)hydroxymethyl]-1-pyrrolidinecarboxylate (Isomer B; Single diastereoisomer; Stereochemistry unassigned) as a colorless oil (0.26 g, 38%); $^1$H NMR (500 MHz, CDCl$_3$) δ 7.67 (1H, s), 7.21 (5H, m), 7.20 (2H, s), 7.03 (2H, m), 4.95 (1H, q, J 6.5 Hz), 4.28 (1H, d, J 8.3 Hz), 4.20

(1H, m), 4.00-2.81 (5H, m), 1.93 (2H, m), 1.70 (3H, m), 1.44 (11H, m), 1.35 (3H, d, J 6.6 Hz).

EXAMPLE 42

(1R or S, 7aR or S)-1-((2R,3R,4R)-{(1R)-1-[3,5-Bis (trifluoromethyl)phenyl]-ethoxy}tetrahydro-3-phenyl-2H-pyran-4-yl)tetrahydro-1H,3H-pyrrolo[1,2-c] oxazol-3-one (Isomer A)

Sodium hydride (60% dispersion in mineral oil, 15 mg, 0.36 mmol) was added to a solution of 1,1-dimethylethyl (2R or S)-2-[(R or S)-((2R,3R,4R)-{(1R)-1-[3,5-bis(trifluoromethyl)phenyl]ethoxy}tetrahydro-3-phenyl-2H-pyran-4-yl) hydroxymethyl]-1-pyrrolidinecarboxylate (Example 41, Isomer A; 75 mg, 0.12 mmol) in tetrahydrofuran (2 mL) and the mixture was stirred at room temperature for 15 hours. Water (2 mL) was added slowly, then ethyl acetate (10 mL). The layers were separated and the organic layer was washed with brine (5 mL). The combined aqueous layers were extracted with ethyl acetate (10 mL). The combined organic layers were dried ($Na_2SO_4$) and the solvent was evaporated under reduced pressure. The residue was purified by column chromatography on silica gel, eluting with hexane/EtOAc (80:20 increasing to 60:40), to give the title compound (Single diastereoisomer; Stereochemistry unassigned) as a colorless foam (54 mg, 82%).

$^1$H NMR (500 MHz, $CDCl_3$) δ 7.67 (1H, s), 7.26 (3H, m), 7.20 (2H, s), 7.06 (2H, m), 4.95 (1H, q, J 6.5 Hz), 4.28 (1H, d, J 8.3 Hz), 4.20 (1H, dt, J 11.4, 3.4 Hz), 3.96 (1H, t, J 3.5 Hz), 3.53 (2H, m), 3.34 (1H, m), 3.06 (1H, m), 2.82 (1H, dd, J 8.3, 11.3 Hz), 1.93 (2H, m), 1.78 (2H, m), 1.68 (2H, m), 1.35 (3H, d, J 6.6 Hz), 1.20 (1H, m).

EXAMPLE 43

(1R or S, 7aR or S)-1-((2R,3R,4R)-{(1R)-1-[3,5-Bis (trifluoromethyl)phenyl]-ethoxy}tetrahydro-3-phenyl-2H-pyran-4-yl)tetrahydro-1H,3H-pyrrolo[1,2-c] oxazol-3-one (Isomer B)

Prepared from (2R or S)-2-[(R or S)-((2R,3R,4R)-{(1R)-1-[3,5-bis(trifluoromethyl)phenyl]ethoxy}tetrahydro-3-phenyl-2H-pyran-4-yl)hydroxymethyl]-1-pyrrolidinecarboxylate (Example 41, Isomer B) according to the method of Example 42.

$^1$H NMR (500 MHz, $CDCl_3$) δ 7.67 (1H, s), 7.30 (2H, s), 7.24 (3H, m), 7.08 (2H, m), 4.98 (1H, q, J 6.5 Hz), 4.54 (1H, dd, J 6.5, 8.6 Hz), 4.42 (1H, d, J 7.2 Hz), 4.17 (1H, dt, J 11.9, 4.0 Hz), 3.60 (1H, dt, J 1.6, 10.8 Hz), 3.55 (1H, m), 2.95 (2H, m), 2.62 (1H, dd, J 7.3, 9.5 Hz), 2.14 (1H, m), 1.98 (1H, m), 1.86 (1H, m), 1.78 (1H, m), 1.52 (1H, m), 1.39 (3H, d, J 6.6 Hz), 1.18 (1H, m), 1.04 (1H, m).

EXAMPLE 44

(2R,3R,4R,αR or S)-α-[(2R or S)-2-Pyrrolidinyl]-2-{(1R)-1-[3,5-bis(trifluoromethyl)phenyl] ethoxy}tetrahydro-3-phenyl-2H-pyran-4-methanol (Isomer B)

Lithium hydroxide (30 mg, 0.70 mmol) was added to a solution of (1R or S, 7aR or S)-1-((2R,3R,4R)-{(1R)-1-[3,5-bis(trifluoromethyl)phenyl]ethoxy}-tetrahydro-3-phenyl-2H-pyran-4-yl)tetrahydro-1H,3H-pyrrolo[1,2-c]oxazol-3-one (Example 43, Isomer B; 76 mg, 0.14 mmol) in tetrahydrofuran (1 mL), methanol (1 mL) and water (1 mL) and the mixture was stirred at 50° C. for 3 days. The mixture was cooled and water (5 mL) and ethyl acetate (10 mL) were added. The layers were separated and the organic layer was washed with brine (5 mL). The combined aqueous layers were extracted with ethyl acetate (10 mL). The combined organic layers were dried ($Na_2SO_4$) and the solvent was evaporated under reduced pressure. The residue was purified by preparative thin layer chromatography on silica gel, eluting with EtOAc/MeOH/$NH_3$(Aq.) (85:15:1.5), to give the title compound (Single diastereoisomer; Stereochemistry unassigned) as a colorless oil (50 mg, 70%).

$^1$H NMR (500 MHz, $CD_3OD$) δ 7.71 (1H, s), 7.32 (2H, s), 7.22-7.12 (5H, m), 5.00 (1H, q, J 6.5 Hz), 4.39 (1H, d, J 8.6 Hz), 4.11 (1H, dt, J 11.4, 3.4 Hz), 3.64 (1H, dt, J 2.4, 12.0 Hz), 2.98 (1H, dd, J 2.0, 8.2 Hz), 2.90 (1H, q, J 7.8 Hz), 2.79 (2H, m), 2.70 (1H, m), 2.10 (1H, m), 1.83 (1H, m), 1.73 (1H, m), 1.63 (3H, m), 1.41 (1H, m), 1.33 (3H, d, J 6.6 Hz); m/z ($ES^+$) 518 (M+1), 260 (M+1-$C_{10}H_8F_6O$).

The invention claimed is:

1. A compound of the formula (Ia)

(Ia)

wherein
- $R^1$ is hydrogen, halogen, $C_{1-6}$alkyl, $C_{1-6}$alkoxy, fluoro$C_{1-6}$alkyl, fluoro$C_{1-6}$alkoxy, $C_{3-7}$cycloalkyl, $C_{3-7}$cycloalkyl$C_{1-4}$alkyl, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;
- $R^2$ is hydrogen, halogen, $C_{1-6}$alkyl, fluoro$C_{1-6}$alkyl or $C_{1-6}$alkoxy substituted by $C_{1-4}$alkoxy;
- $R^3$ is hydrogen, halogen or fluoro$C_{1-6}$alkyl;
- $R^4$ is hydrogen, halogen, $C_{1-6}$alkyl, $C_{1-6}$alkoxy, fluoro$C_{1-6}$alkyl, fluoro$C_{1-6}$alkoxy, hydroxy, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;
- $R^5$ is hydrogen, halogen, $C_{1-6}$alkyl, fluoro$C_{1-6}$alkyl or $C_{1-6}$alkoxy substituted by $C_{1-4}$alkoxy;
- $R^6$ represents hydrogen or a $C_{1-4}$alkyl group optionally substituted by a hydroxy group;
- $R^7$ represents hydrogen, $C_{1-6}$alkyl, fluoro$C_{1-6}$alkyl, hydroxy, $C_{1-6}$alkoxy or hydroxy$C_{1-6}$alkyl;
- $R^8$ and $R^9$ each independently represent hydrogen, halogen, $C_{1-6}$alkyl, $CH_2OR^c$, oxo, $CO_2R^a$ or $CONR^aR^b$ where $R^a$ and $R^b$ are as previously defined and $R^c$ represents hydrogen, $C_{1-6}$alkyl or phenyl;
- A represents an oxygen atom or a $CH_2$ group;
- B represents an oxygen atom or a $CH_2$ group, with the proviso that when A is an oxygen atom, B is a $CH_2$ group, and when A is a $CH_2$ group, B is an oxygen atom;

n is 1 or 2;

m is 1, 2 or 3, with the proviso that the sum total of m+n is 2, 3 or 4;

$R^{10}$ is hydrogen, halogen, hydroxy, $C_{1-4}$alkyl, $C_{3-7}$cycloalkyl, $C_{3-7}$cycloalkyl$C_{1-4}$alkyl, hydroxy$C_{1-4}$alkyl, $C_{1-4}$alkoxy$C_{1-4}$alkyl, $C_{2-6}$alkenyl or $C_{2-6}$alkynyl;

$R^{11}$ is hydrogen, halogen, hydroxy or $C_{1-4}$alkyl;

or $R^{10}$ and $R^{11}$ may together represent an oxo (=O) group, with the proviso that the oxo group is not adjacent to the oxygen atom represented by either A or B;

wherein one or both of $R^{10}$ and $R^{11}$ may replace one or both hydrogen atoms in the CH$_2$ group represented by A or B;

or a pharmaceutically acceptable salt thereof.

2. A compound as claimed in claim 1 of the formula (Iaa)

(Iaa)

wherein $R^1$ is fluorine or CF$_3$;

$R^2$ is fluorine or CF$_3$;

$R^4$ is hydrogen or fluorine;

$R^5$ is hydrogen, fluorine or bromine; and $R^6$ is methyl or hydroxymethyl or a pharmaceutically acceptable salt thereof.

3. A compound as claimed in claim 1 of the formula (Iab)

wherein

X represents CHOH or C=O;

$R^1$ is fluorine or trifluoromethyl;

$R^2$ is fluorine or trifluoromethyl;

$R^6$ is methyl or hydroxymethyl;

$R^4$ is hydrogen or fluorine; and $R^5$ is hydrogen or fluorine;

or a pharmaceutically acceptable salt thereof.

4. A compound as claimed in claim 3 of the formula (Iaba)

(Iaba)

wherein $R^5$ is hydrogen or fluorine; and $R^4$ is hydrogen or fluorine;

or a pharmaceutically acceptable salt thereof.

5. A compound as claimed in claim 1 selected from;

(4RS)-8-[(2R,3R,4R)-2-[(1R)-1-(3,5-bis(trifluoromethyl)phenyl)ethoxy]-3-phenyl-tetrahydropyran-4-yl]methyl-2-oxa-8-aza-spiro[4,5]decan-4-ol;

(4S)-8-[(2R,3R,4R)-2-[(1R)-1-(3,5-bis(trifluoromethyl)phenyl)ethoxy]-3-(4-fluorophenyl)tetrahydropyran-4-yl]methyl-2-oxa-8-aza-spiro[4,5]decan-4-ol;

(4R)-8-[(2R,3R,4R)-2-[(1R)-1-(3,5-bis(trifluoromethyl)phenyl)ethoxy]-3-(4-fluorophenyl)tetrahydropyran-4-yl]methyl-2-oxa-8-aza-spiro[4,5]decan-4-ol;

(4RS)-8-[(2R,3R,4R)-2-[(1R)-1-(3,5-bis(trifluoromethyl)phenyl)ethoxy]-3-(3,4-difluorophenyl)tetrahydropyran-4-yl]methyl-2-oxa-8-aza-spiro[4,5]decan-4-ol;

8-[(2R,3R,4R)-2-[(1R)-1-(3,5-bis(trifluoromethyl)phenyl)ethoxy]-3-(4-fluorophenyl)tetrahydropyran-4-yl]methyl-2-oxa-8-aza-spiro[4,5]decane;

8-[(2R,3S,4S)-2-[(1R)-1-(3,5-bis(trifluoromethyl)phenyl)ethoxy]-3-phenyl(tetrahydropyran-4-yl)]methyl-1,1-dimethyl-2-oxa-8-aza-spiro[4,5]decane;

8-[(2R,3S,4S)-2-[(1R)-1-(3,5-bis(trifluoromethyl)phenyl)ethoxy]-3-phenyl(tetrahydropyran-4-yl)]methyl-2,2-dimethyl-1-oxa-8-aza-spiro[4,5]decane;

8-[(2R,3S,4S)-2-[(1R)-1-(3,5-bis(trifluoromethyl)phenyl)ethoxy]-3-phenyl-tetrahydropyran-4-yl]methyl-1-oxa-8-aza-spiro[4,5]decane;

8-[(2R,3S,4S)-2-[(1R)-1-(3,5-bis(trifluoromethyl)phenyl)ethoxy]-3-phenyl-tetrahydropyran-4-yl]methyl-2-oxa-8-aza-spiro[4,5]decane;

8-[(2R,3R,4R)-2-[(1R)-1-(3,5-bis(trifluoromethyl)phenyl)ethoxy]-3-phenyl-tetrahydropyran-4-yl]methyl-2-oxa-8-aza-spiro[4,5]decane;

8-[(2R,3R,4R)-2-[(1R)-1-(3,5-bis(trifluoromethyl)phenyl)ethoxy]-3-phenyl-tetrahydropyran-4-yl]methyl-2,2-dimethyl-1-oxa-8-aza-spiro[4,5]decane;

8-[(2R,3R,4R)-2-[(1R)-1-(3,5-bis(trifluoromethyl)phenyl)ethoxy]-3-phenyl-tetrahydropyran-4-yl]methyl-1-oxa-8-aza-spiro[4,5]decane;

8-[(2R,3R,4R)-2-[(1R)-1-(3,5-bis(trifluoromethyl)phenyl)ethoxy]-3-phenyl-tetrahydropyran-4-yl]methyl-1,1-dimethyl-2-oxa-8-aza-spiro[4,5]decane;

8-[(2R,3R,4R)-2-[(1R)-1-(3,5-bis(trifluoromethyl)phenyl)ethoxy]-3-(4-fluorophenyl)tetrahydropyran-4-yl]methyl-2-oxa-8-aza-spiro[4,5]decan-4-one;

(4RS)-8-[(2R,3R,4R)-2-[(1R)-1-(3,5-bis(trifluoromethyl)phenyl)ethoxy]-3-(4-fluorophenyl)tetrahydropyran-4-yl]methyl-2-oxa-4-methyl-8-aza-spiro[4,5]decan-4-ol;

(4R)-8-[(2R,3R,4R)-2-[(1R)-1-(3,5-bis(trifluoromethyl)phenyl)ethoxy]-3-(3-bromo-4-fluorophenyl)tetrahydropyran-4-yl]methyl-2-oxa-8-aza-spiro[4,5]decan-4-ol;

(4RS)-8-[(2R,3R,4R)-2-[(1R)-1-(3,5-bis(trifluoromethyl)phenyl)ethoxy]-(4-fluorophenyl)tetrahydropyran-4-yl]methyl-2-oxa-4-ethynyl-8-aza-spiro[4,5]decan-4-ol;

(8S)-2-[((2R,3R,4R)-2-[(1R)-1-[3,5-bis(trifluoromethyl)phenyl]ethoxy]-3-phenyltetrahydro-2H-pyran-4-yl)methyl]-6-oxa-2-azaspiro[3,4]octan-8-ol;

(8R)-2-[((2R,3R,4R)-2-[(1R)-1-[3,5-bis(trifluoromethyl)phenyl]ethoxy]-3-phenyl)tetrahydro-2H-pyran-4-yl)methyl]-6-oxa-2-azaspiro[3,4]octan-8-ol;

(4RS)-8-[(2R,3R,4R)-2-[(1R)-1-(3,5-bis(trifluoromethyl)phenyl)ethoxy]-3-phenyltetrahydropyran-4-yl]methyl-1-oxa-8-azaspiro[4,5]decan-4-ol;

(4RS)-8-[(2R,3R,4R)-2-[(1R)-1-(3,5-bis(trifluoromethyl)phenyl)ethoxy]-3-(4-fluorophenyl)tetrahydropyran-4-yl]methyl-3,3-dimethyl-2-oxa-8-azaspiro[4,5]decan-4-ol;

(4R*)-8-[(2R,3R,4R)-2-[(1R)-1-(3,5-bis(trifluoromethyl)phenyl)ethoxy]-3-(4fluorophenyl)tetrahydropyran-4-yl]methyl-1-oxa-8-azaspiro[4,5]decan-4-ol;

(4S*)-8-[(2R,3R,4R)-2-[(1R)-1-(3,5-bis(trifluoromethyl)phenyl)ethoxy]-3-(4-fluorophenyl)tetrahydropyran-4-yl]methyl-1-oxa-8-azaspiro[4,5]decan-4-ol;

(4R)-8-[((2R,3R,4R)-2-{(1R)-1-[3,5-bis(trifluoromethyl)phenyl]ethoxy}-3-phenyltetrahydro-2H-pyran-4-yl)methyl]-4-methoxy-2-oxa-8-azaspiro[4,5]decane;

(4R)-8-[((2R,3R,4R)-2-{(1R)-1-[3,5-bis(trifluoromethyl)phenyl]ethoxy}-3-(4-fluorophenyl)tetrahydro-2H-pyran-4-yl)methyl]-4-methoxy-2-oxa-8-azaspiro[4,5]decane;

8-[((2R,3R,4R)-2-{(1R)-1-[3,5-bis(trifluoromethyl)phenyl]ethoxy}-3-phenyltetrahydro-2H-pyran-4-yl)methyl]-1-oxa-8-azaspiro[4,5]decan-3-ol;

8-[((2R,3R,4R)-2-{(1R)-1-[3,5-bis(trifluoromethyl)phenyl]ethoxy}-3-phenyltetrahydro-2H-pyran-4-yl)methyl]-1-oxa-8-azaspiro[4,5]decan-3-one;

or a pharmaceutically acceptable salt thereof.

6. A pharmaceutical composition comprising a compound according to claim 1 together with at least one pharmaceutically acceptable carrier or excipient.

7. A pharmaceutical composition comprising a compound according to claim 5 together with at least one pharmaceutically acceptable carrier or excipient.

8. A method for the treatment of emesis, which method comprises administration to a patient in need thereof of a therapeutically effective amount of a compound according to claim 1.

9. A method for the treatment of emesis, which method comprises administration to a patient in need thereof of a therapeutically effective amount of a compound according to claim 5.

* * * * *